(12) United States Patent
Gottesman et al.

(10) Patent No.: US 11,116,778 B2
(45) Date of Patent: Sep. 14, 2021

(54) PRODRUGS OF ALOX-15 INHIBITORS AND METHODS OF USING THE SAME

(71) Applicant: EMPIRICO INC., San Diego, CA (US)

(72) Inventors: Omri Gottesman, San Diego, CA (US); Shannon Bruse, San Diego, CA (US); Brian Cajes, San Diego, CA (US); David Lewis, Madison, WI (US); David Rozema, Cross Plains, WI (US)

(73) Assignee: EMPIRICO INC., San Diego, CA (US)

( * ) Notice: Subject to any disclaimer, the term of this patent is extended or adjusted under 35 U.S.C. 154(b) by 0 days.

(21) Appl. No.: 16/961,242

(22) PCT Filed: Jan. 14, 2020

(86) PCT No.: PCT/US2020/013546
§ 371 (c)(1),
(2) Date: Jul. 9, 2020

(87) PCT Pub. No.: WO2020/150265
PCT Pub. Date: Jul. 23, 2020

(65) Prior Publication Data
US 2021/0030772 A1  Feb. 4, 2021

Related U.S. Application Data

(60) Provisional application No. 62/883,442, filed on Aug. 6, 2019, provisional application No. 62/849,297, filed on May 17, 2019, provisional application No. 62/792,816, filed on Jan. 15, 2019.

(51) Int. Cl.
*A61K 31/675* (2006.01)
*A61K 31/415* (2006.01)
*C07D 231/10* (2006.01)
*C07D 231/14* (2006.01)

(52) U.S. Cl.
CPC .......... *A61K 31/675* (2013.01); *A61K 31/415* (2013.01); *C07D 231/10* (2013.01); *C07D 231/14* (2013.01)

(58) Field of Classification Search
CPC .. A61K 31/675; A61K 31/415; C07D 231/10; C07D 231/14
See application file for complete search history.

(56) References Cited

U.S. PATENT DOCUMENTS

| | | | |
|---|---|---|---|
| 4,476,116 A | 10/1984 | Anik | |
| 4,897,355 A | 1/1990 | Eppstein et al. | |
| 5,033,252 A | 7/1991 | Carter | |
| 5,052,558 A | 10/1991 | Carter | |
| 5,116,817 A | 5/1992 | Anik | |
| 5,171,678 A | 12/1992 | Behr et al. | |
| 5,283,185 A | 2/1994 | Epand et al. | |
| 5,323,907 A | 6/1994 | Kalvelage | |
| 5,328,470 A | 7/1994 | Nabel et al. | |
| 6,391,452 B1 | 5/2002 | Antonsen et al. | |
| 6,686,502 B1 | 2/2004 | Cai et al. | |
| 7,021,394 B2 | 4/2006 | Marchesan | |
| 7,626,014 B2 | 12/2009 | Manoharan et al. | |
| 7,745,608 B2 | 6/2010 | Manoharan et al. | |
| 8,034,921 B2 | 10/2011 | Manoharan et al. | |
| 2005/0164235 A1 | 7/2005 | Manoharan et al. | |
| 2009/0143455 A1* | 6/2009 | Pelcman | A61P 9/10 514/406 |
| 2011/0030072 A1 | 2/2011 | Weinstein et al. | |
| 2015/0020223 A1 | 1/2015 | Zhang et al. | |
| 2015/0355180 A1 | 12/2015 | Resnick et al. | |
| 2016/0168137 A1 | 6/2016 | Van Leyen et al. | |
| 2016/0177394 A1 | 6/2016 | Rothenberg et al. | |
| 2017/0067108 A1 | 3/2017 | Abbas et al. | |
| 2017/0286594 A1 | 10/2017 | Reid et al. | |

FOREIGN PATENT DOCUMENTS

| | | | |
|---|---|---|---|
| EP | 2959899 A1 | 12/2015 | |
| WO | WO-9116024 A1 | 10/1991 | |
| WO | WO-9324640 A2 | 12/1993 | |
| WO | WO-9400569 A1 | 1/1994 | |
| WO | WO-9637194 A1 | 11/1996 | |
| WO | WO-9839359 A1 | 9/1998 | |
| WO | WO-2011130707 A2 * | 10/2011 | ........... C07D 219/08 |
| WO | WO-2014059178 A1 | 4/2014 | |
| WO | WO-2019157304 A1 | 8/2019 | |
| WO | WO-2020117840 A2 | 6/2020 | |
| WO | WO-2020139830 A2 | 7/2020 | |
| WO | WO-2020150265 A1 | 7/2020 | |

OTHER PUBLICATIONS

Jornada et al. (Molecules, 2016, 21(1), 42). (Year: 2016).*
Ansel et al.: Pharmaceutical Dosage Forms and Drug Delivery Systems 213, 6th ed., (1995).
Archambault et al.: Comparison of eight 15-lipoxygenase (LO) inhibitors on the biosynthesis of 15-LO metabolites by human neutrophils and eosinophils. PLoS One, 13(8):1/15-15/15, e0202424 (2018).
Berge et al.: Pharmaceutical Salts. Journal of Pharmaceutical Science. 66:1-19 (1997).
Bundgaard. Design and Application of Prodrugs. Textbook of Drug Design and Development. Krosgaard-Larsen and Bundgaard. Chapter 5. pp. 113-191 (1991).
Bundgaard et al. Design of Prodrugs pp. 7-9, 21-24 (1985).
Bundgaard. Means to Enhance Penetration: Prodrugs as a Means to Improve the Delivery of Peptide Drugs. Advanced Drug Delivery Review 8:1-38 (1992).

(Continued)

Primary Examiner — Kara R McMillian
(74) Attorney, Agent, or Firm — Wilson Sonsini Goodrich & Rosati

(57) ABSTRACT

Described herein are compounds and pharmaceutical compositions containing such compounds which are prodrugs of ALOX-15 inhibitors. Also described herein are methods for using such compounds in the treatment of disease.

9 Claims, 11 Drawing Sheets

(56) References Cited

OTHER PUBLICATIONS

Han et al.: Human 15-lipoxygenase-1 is a regulator of dendritic-cell spreading and podosome formation. FASEB J, 31, 491-504 (2017).
Kristjansson et al.: A loss-of-function variants protects against nasal polyps and chronic rhinosinusitis. Nature Genetics, Nature Publishing Group. 51(2):267-276 (2019).
Kumpulainen et al.: Synthesis, in vitro and in vivo characterization of novel ethyl dioxy phosphate prodrug of propofol. Eur J Pharm Sci, 34, 110-7 (2008).
Leconet et al.: Nonviral Delivery of Small Interfering RNA Into Pancreas-associated Immune Cells Prevents Autoimmune Diabetes. Molecular Therapy. The Journal of the American Society of Gene Therapy. 20(12):2315-2325 (2012).
PCT/US2019/017244 International Search Report and Written Opinion dated Apr. 11, 2019.
PCT/US2019/064286 Invitation to Pay Additional Fees dated Mar. 17, 2020.
PCT/US2019/064286 International Search Report and Written Opinion dated Jun. 24, 2020.
PCT/US2020/013546 International Search Report and Written Opinion dated May 15, 2020.
Pelcman et al.: 3-Substituted pyrazoles and 4-substituted triazoles as inhibitors of human 15-lipoxygenase-1. Bioorg Med Chem Lett, 25, 3024-9 (2015).
Pelcman et al.: N-Substituted pyrazole-3-carboxamides asinhibitors of human 15-lipoxygenase. Bioorganic & Medicinal Chemistry Letters 25(15): 3017-3023 (2015).
Remington: The Science and Practice of Pharmacy, 21st Edition, Lippincott Williams & Wilkins, chapter 41, p. 802, 2005.
Samanta et al., Characterization of a human 12/15-lipoxygenase promoter variant associated with atherosclerosis identifies vimentin as a promoter binding protein. PLoS One 7(8):e42417 [1-10] doi: 10.1371/journal.pone.0042417 (2012).
Snodgrass et al.: A Novel Function for 15-Lipoxygenases in Cholesterol Homeostasis and CCL17 Production in Human Macrophages. Frontiers in Immunology. 9:16 pages (2018).
Widder et al. Section III: Prodrugs Kinetics. Method in Enzymology. 112:309-396 (1985).
Zhao et al.: Interleukin-13-induced MUC5AC Is Regulated by 15-Lipoxygenase 1 Pathway in Human Bronchial Epithelial Cells. American Journal of Respiratory and Critical Care Medicine. 179(9):782-790 (2009).
Allen et al.: R. & UK Biobank. UK biobank data: come and get it. Sci. Transl. Med. 6, 224ed4 (2014).
Allerson et al.: Fully 2'-Modified Oligonucleotide Duplexes with Improved in Vitro Potency and Stability Compared to Unmodified Small Interfering RNA. J. Med. Chem. 48:901-904 (2005).
Andersson et al.: Mice Lacking 12/15-Lipoxygenase Have Attenuated Airway Allergic Inflammation and Remodeling. American Journal of Respiratory Cell and Molecular Biology. 39(6):648-656 (2008).
Assimes et al.: A near null variant of 12/15-LOX encoded by a novel SNP in ALOX15 and the risk of coronary artery disease. Atherosclerosis. 198:136-144 (2008).
Atherton et al.: IL-13-induced changes in the goblet cell density of human bronchial epithelial cell cultures: MAP kinase and phosphatidylinositol 3-kinase regulation. Am. J. Physiol. Lung Cell. Mol. Physiol. 285:L730-739 (2003).
Awji et al.: Wood smoke enhances cigarette smoke-induced inflammation by inducing the aryl hydrocarbon receptor repressor in airway epithelial cells. Am. J. Respir. Cell Mol. Biol. 52:377-386 (2015).
Bangham et al.: Diffusion of univalent ions across the lamellae of swollen phospholipids. M. Mol. Biol. 23:238 (1965).
Brown et al.: Regulation of 15-lipoxygenase isozymes and mucin secretion by cytokines in cultured normal human bronchial epithelial cells. Inflamm. Res. 50:321-326 (2001).
Chand et al.: Blocking Bcl-2 resolves IL-13-mediated mucous cell hyperplasia in a Bik-dependent manner. J. Allergy Clin. Immunol. 140:1456-1459.e9 (2017).
Chand et al.: IL-13 in LPS-Induced Inflammation Causes Bcl-2 Expression to Sustain Hyperplastic Mucous cells. Sci. Rep. 8:436 (2018).
Chen et al.: 1,6-O,O-Diacetylbritannilactone Inhibits Eotaxin-1 and ALOX15 Expression Through Inactivation of STAT6 in A549 Cells Inflammation. 40(6):1967-1974 (2017).
Chen et al.: Gene therapy for brain tumors: regression of experimental gliomas by adenovirus-mediated gene transfer in vivo. Proc. Natl. Acad. Sci. USA 91:3054-3057 (1994).
Chiu et al.: siRNA function in RNAi: a chemical modification analysis. RNA 9:1034-1048 (2003).
Choung et al.: Chemical modification of siRNAs to improve serum stability without loss of efficacy. Biochemical and Biophysical Research Communications 342(3):919-927 (2006).
Chu et al.: Expression and activation of 15-lipoxygenase pathway in severe asthma: relationship to eosinophilic phenotype and collagen deposition, Clinical and Experimental Allergy. 32(11):1558-65 (2002).
Cingi et al.: Antileukotriene in upper airway inflammatory diseases, Curr. Allergy Asthma Rep. 15(1):64 (2015).
Claesson et al.: On the biosynthesis and biological role of eoxins and 15-lipoxygenase-1 in airway inflammation and Hodgkin lymphoma, Prostaglandins and other Lipid Mediators. 89(3-4):120-125 (2009).
Conrad et al.: Specific inflammatory cytokines regulate the expression of human monocyte 15-lipoxygenase. Proc. Natl. Acad. Sci. U. S. A. 89:217-221 (1992).
Cornejo-Garcia et al.: Genetic variants of the arachidonic acid pathway in non-steroidal anti-inflammatory drug-induced acute urticaria. Clin. & Exp. Allergy 42: 1772-81 (2012).
Czapski et al.: Evaluation of the antioxidative properties of lipoxygenase inhibitors. Pharmacological Reports. 64(5):1179-1188 (2014).
Czauderna et al.: Structural variations and stabilising modifications of synthetic siRNAs in mammalian cells. Nucl. Acids Res., 31:2705-2716 (2003).
Dahlen et al.: Benefits from Adding the 5-Lipoxygenase Inhibitor Zileuton to Conventional Therapy in Aspirin-intolerant Asthmatics. American Journal of Respiratory and Critical Care Medicine. 157(4): 1187-1194 (1998).
Elbashir et al.: RNA interference is mediated by 21- and 22-nucleotide RNAs. Genes Dev. 15, 188-200 (2001).
Elmen et al.: Locked nucleic acid (LNA) mediated improvements in siRNA stability and functionality. Nucl. Acids Res. 33:439-447 (2005).
Feigner et al.: Enhanced gene delivery and mechanism studies with a novel series of cationic lipid formulations. J. Biol. Chem. 269:2550-2561 (1994).
Feigner et al.: Lipofection: a highly efficient, lipid-mediated DNA-transfection procedure. Proc. Natl. Acad. Sci., USA 8:7413-7417 (1987).
Fire et al.: Potent and specific genetic interference by doublestranded RNA in Caenorhabditis elegans. Nature 391, 806-811 (1998).
Fong et al.: GWAS Analyzer: integrating genotype, phenotype and public annotation data for genome-wide association study analysis. Bioinformatics. 26(4):560-564 (2010).
Fukunaga et al.: Liposome entrapment enhances the hypocalcemic action of parenterally administered calcitonin. Endocrinol. 115:757-767 (1984).
Gao et al.: A novel cationic liposome reagent for efficient transfection of mammalian cells. Biochim. Biophys. Res. Commun. 179(1):280-285 (1991).
Gavett et al.: Interleukin-4 receptor blockade prevents airway responses induced by antigen challenge in mice. Am. J. Physiol. 272:L253-261 (1997).
Gershon: Mode of formation and structural features of DNA-cationic liposome complexes used for transfection. Biochem. 32:7143-7151 (1993).
Gottesman et al.: The CLIPMERGE PGx Program: Clinical Implementation of Personalized Medicine through Electronic Health Records and Genomics—Pharmacogenomics. Clin Pharmacol Ther. 94(2):214-217 (2013).
Gudbjartsson et al.: Sequence variants affecting eosinophil numbers associate with asthma and myocardial infarction. Nat. Genet. 41:342-347 (2009).

(56) References Cited

OTHER PUBLICATIONS

Heydeck et al.: Interleukin-4 and -13 induce upregulation of the murine macrophage 12/15-lipoxygenase activity: evidence for the involvement of transcription factor STAT6. Blood 92:2503-2510 (1998).
Horn et al.: Functional characterization of genetic enzyme variations in human lipoxygenases. Redox Biol. 1:566-577 (2013).
Itani et al.: A simple and efficient liposome method for transfection of DNA into mammalian cells grown in suspension. Gene 56:267-276 (1987).
Ivanov et al.: Structural and functional biology of arachidonic acid 15-lipoxygenase-1 (ALOX15). Gene. 573(1): 1-32 (2015).
Jayawickreme et al.: Regulation of 15-lipoxygenase expression and mucus secretion by IL-4 in human bronchial epithelial cells. vol. 276(4):L596-603 (1999).
Kim et al.: Expression of 15-lipoxygenase-1 in human nasal epithelium—Its implication in mucociliary differentiation. Prostaglandins, Leukotrienes, and Essential Fatty acids. 73:77-83 (2005).
Kim et al.: Preparation of multivesicular liposomes. Biochim. Biophys. Acta 728:339 (1983).
Kroegel et al.: Endobronchial secretion of interleukin-13 following local allergen challenge in atopic asthma: relationship to interleukin-4 and eosinophil counts. Eur. Respir. J. 9:899-904 (1996).
Kumar et al.: Role of interleukin-13 in eosinophil accumulation and airway remodelling in a mouse model of chronic asthma. Clin. Exp. Allergy J. Br. Soc. Allergy Clin. Immunol. 32:1104-1111 (2002).
Kumlin et al.: 15(S)-Hydroxyeicosatetraenoic Acid Is the Major Arachidonic Acid Metabolite in Human Bronchi—Association with Airway Epithelium Archives of Biochemistry and Biophysics. 282(2):254-262 (1990).
Lam et al.: A new type of synthetic peptide library for identifying ligand-binding activity. Nature, 354:82-84 (1991).
Laoukili et al.: IL-13 alters mucociliary differentiation and ciliary beating of human respiratory epithelial cells. J. Clin. Invest. 108:1817-1824 (2001).
Laprise et al.: Functional classes of bronchial mucosa genes that are differentially expressed in asthma. BMC Genomics. 5:21 (2004).
Layzer et al.: In vivo activity of nuclease-resistant siRNAs. RNA, 10:766-771 (2004).
Leuschner et al.: Cleavage of the siRNA passenger strand during RISC assembly in human cells. EMBO Rep. 7(3):314-320 (2006).
Mabalirajan et al.: Effects of vitamin E on mitochondrial dysfunction and asthma features in an experimental allergic murine model. J. of Applied Physiology, 107(4):1285-1292 (2009).
Mannino et al.: Liposome mediated gene transfer. Biotechniques 6:682-690 (1988).
Mattes et al.: IL-13 induces airways hyperreactivity independently of the IL-4R alpha chain in the allergic lung. J. Immunol. Baltim. Md. 1950(167):1683-1692 (2001).
Mayer et al.: Vesicles of variable sizes produced by a rapid extrusion procedure. Biochim. Biophys. Acta 858(1):161-168 (1986).
Mayhew et al.: Characterization of liposomes prepared using a microemulsifier. Biochim. Biophys. Acta 775: 169 (1984).
Modena et al.: Emerging concepts: mast cell involvement in allergic diseases, Translational Research. 174(24):98-121 (2016).
Morrissey et al.: Activity of stabilized short interfering RNA in a mouse model of hepatitis B virus replication. Hepatology 41(6):1349-56 (2005).
Muhonen et al.: RNA Interference Tolerates 2'-Fluoro Modifications at the Argonaute2 Cleavage Site. Chemistry & Biodiversity 4(5):858-873 (2007).
Munitz et al.: Distinct roles for IL-13 and IL-4 via IL-13 receptor alpha1 and the type II IL-4 receptor in asthma pathogenesis. Proc. Natl. Acad. Sci. U. S. A. 105:7240-7245 (2008).
Nabel et al.: Direct gene transfer with DNA-liposome complexes in melanoma: expression, biologic activity, and lack of toxicity in humans. Proc. Natl. Acad. Sci. 90(23):11307-11311 (1993).
Nabel et al.: Gene transfer in vivo with DNA-liposome complexes: lack of autoimmunity and gonadal localization. Human Gene Ther. 3(6):649-656 (1992).
Nassar et al.: Induction of 15-lipoxygenase by interleukin-13 in human blood monocytes. J. Biol. Chem. 269:27631-27634 (1994).
Nials et al.: Mouse models of allergic asthma: acute and chronic allergen challenge. Dis. Model. Mech. 1:213-220 (2008).
Nicolau et al.: Liposomes as carriers for in vivo gene transfer and expression. Meth. Enz. 149:157-176 (1987).
Olson et al.: Preparation of liposomes of defined size distribution by extrusion through polycarbonate membranes. Biochim. Biophys. Acta 557(1):9-23 (1979).
PCT/US2019/017244 International Preliminary Report on Patentability dated Aug. 11, 2020.
Pierce et al.: Loss of pro-apoptotic Bim promotes accumulation of pulmonary T lymphocytes and enhances allergen-induced goblet cell metaplasia. Am. J. Physiol. Lung Cell. Mol. Physiol. 291:L862-870 (2006).
Prakash et al.: Positional effect of chemical modifications on short interference RNA activity in mammalian cells. J. Med. Chem. 48(13):4247-4253 (2005).
Profita et al.: 15-Lipoxygenase expression and 15(S)-hydroxyeicoisatetraenoic acid release and reincorporation in induced sputum of asthmatic subjects. Journal of Allergy and Clinical Immunology. 105(4):711-716 (2000).
Rand et al.: Argonaute2 cleaves the anti-guide strand of siRNA during RISC activation. Cell 123(4):621-629 (2005).
Rossaint et al.: Eliminating for blocking 12/15-lipoxygenase reduces neutrophil recruitment in mouse models of acute lung injury. Critical Care 16(5):R166 (2012).
Rostkowska-Nadolska et al.: A microarray study of gene expression profiles in nasal polyps. Auris Nasus Larynx. 38(1):58-64 (2011).
Schurmann et al.: Molecular basis for the reduced catalytic activity of the naturally occurring T560M mutant of human 12/15-lipoxygenase that has been implicated in coronary artery disease. J. Biol. Chem. 286:23920-23927 (2011).
Schwarz et al.: The RNA-induced silencing complex is a Mg2+-dependent endonuclease. Curr. Biol. 4(9):787-91 (2004).
Shi et al.: IFN-gamma, but not Fas, mediates reduction of allergen-induced mucous cell metaplasia by inducing apoptosis. J. Immunol. Baltim. Md 1950(168):4764-4771 (2002).
Smith et al.: A rare IL33 loss-of-function mutation reduces blood eosinophil counts and protects from asthma. PLoS Genet. 13:e1006659 (2017).
Smith et al.: Comparison of arachidonic acid metabolism in nasal polyps and eosinophils. Int. Arch. Allergy Appl. Immunol. 82(1):83-88 (1987).
Steinke et al.: Leukotriene synthesis inhibitors versus antagonists: the pros and cons. Curr Allergy Asthma Rep. 7(2):126-133 (2007).
Straubinger et al.: Liposomes as carriers for intracellular delivery of nucleic acids. Meth. Enz. 101 :512-527 (1983).
Strauss et al.: Molecular complementation of a collagen mutation in mammalian cells using yeast artificial chromosomes. EMBO J. 11(2):417-22 (1992).
Sudlow et al.: UK biobank: an open access resource for identifying the causes of a wide range of complex diseases of middle and old age. PLoS Med. 12:e1001779 (2015).
Szoka et al.: Procedure for preparation of liposomes with large internal aqueous space and high capture by reverse-phase evaporation. Proc. Natl. Acad. Sci. 75(9):4194-4198 (1978).
Tesfaigzi et al.: Bax is crucial for IFN-gamma-induced resolution of allergen-induced mucus cell metaplasia. J. Immunol. Baltim. Md (1950)169:5919-5925 (2002).
Tesfaigzi: Regulation of mucous cell metaplasia in bronchial asthma. Curr. Mol. Med. 8:408-415 (2008).
Wang et al.: pH-sensitive immunoliposomes mediate target-cell-specific delivery and controlled expression of a foreign gene in mouse. Proc. Natl. Acad. Sci. USA 84(22):7851-7855 (1987).
Weiner et al.: Liposomes: a novel topical delivery system for pharmaceutical and cosmetic applications. Journal of Drug Targeting. 2(5):405-410 (1994).
Wenzel et al.: Dupilumab in persistent asthma with elevated eosinophil levels. N. Engl. J. Med. 368:2455-2466 (2013).

(56) References Cited

OTHER PUBLICATIONS

Woodruff et al.: Genome-wide profiling identifies epithelial cell genes associated with asthma and with treatment response to corticosteroids. Proc. Natl. Acad. Sci. U. S. A. 104:15858-15863 (2007).

Xiang et al.: IL-9 and IL-13 induce mucous cell metaplasia that is reduced by IFN-gamma in a Bax-mediated pathway. Am. J. Respir. Cell Mol. Biol. 38:310-317 (2008).

Zhou et al.: Lipophilic polylysines mediate efficient DNA transfection in mammalian cells. Biochim. Biophys. Acta 1065(1):8-14 (1991).

Zhou et al.: Targeted delivery of DNA by liposomes and polymers. Journal of Controlled Release. 19:269-274 (1992).

Zitzmann et al.: Arginine-glycine-aspartic acid (RGD)-peptide binds to both tumor and tumor-endothelial cells in vivo. Cancer Res. 62(18):5139-5143 (2002).

\* cited by examiner

PRODRUGS OF ALOX-15 INHIBITORS AND METHODS OF USING THE SAME

CROSS-REFERENCE

This application is a U.S. National Phase of International Application No. PCT/US20/13546 filed Jan. 14, 2020, which claims the benefit of U.S. Provisional Application No. 62/792,816, filed on Jan. 15, 2019, U.S. Provisional Application No. 62/849,297, filed on May 17, 2019, and U.S. Provisional Application No. 62/883,442, filed on Aug. 6, 2019, all of which are herein incorporated by reference in their entirety.

BACKGROUND OF THE INVENTION

Human ALOX-15 (15-lipoxygenase) protein is highly expressed in circulating blood eosinophils, airway epithelial cells and esophageal squamous epithelial cells. As such, ALOX-15 inhibitors are a druggable target for treating eosinophilic airway diseases, such as asthma, chronic rhinosinusitis, nasal polyposis, and allergic rhinitis and eosinophilic diseases of the gastro-intestinal tract, such as eosinophilic esophagitis and eosinophilic gastroenteritis.

SUMMARY OF THE INVENTION

Described herein are prodrugs of ALOX-15 inhibitors. Also disclosed herein are methods for synthesizing such prodrugs and methods for using such prodrugs in the treatment of diseases wherein ALOX-15 inhibition provides therapeutic benefit to the patient having the disease. Further described are pharmaceutical formulations that include a prodrug of an ALOX-15 inhibitor.

In one aspect is a compound having the structure of Formula (I) or Formula (II):

Formula (I)

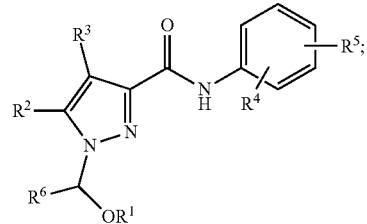

Formula (II)

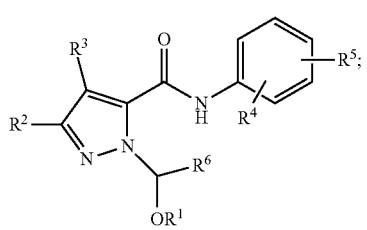

wherein:
$R^1$ is $-P(O)(OH)_2$, $-C(O)N(R^9)C_{2-6}alkyl-OC(O)R^7$,

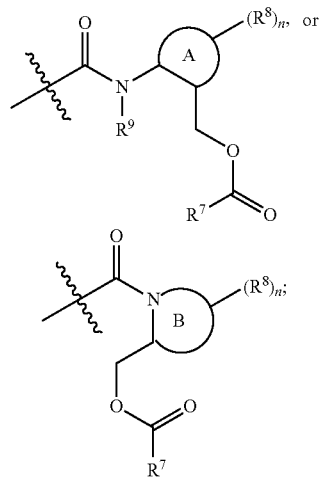

Ring A is selected from $C_{3-6}$cycloalkyl, $C_{2-9}$heterocycloalkyl, $C_{6-10}$aryl, and $C_{2-9}$heteroaryl;

Ring B is selected from $C_{2-9}$heterocycloalkyl and $C_{2-9}$heteroaryl;

$R^2$, $R^3$, $R^4$, and $R^5$ are each independently selected from H, halogen, $-CN$, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, $-OR^{10}$, $-SR^{10}$, $-N(R^{10})_2$, $-C(O)OR^{10}$, $-C(O)N(R^{10})_2$, $-OC(O)N(R^{10})_2$, $-N(R^{11})C(O)N(R^{10})_2$, $-N(R^{11})C(O)OR^{10}$, $-N(R^{11})C(O)R^{12}$, $-N(R^{11})S(O)_2R^{12}$, $-C(O)R^{12}$, $-S(O)R^{12}$, $-S(O)_2R^{12}$, $-S(O)_2N(R^{10})_2$, and $-OC(O)R^{12}$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{13}$;

$R^6$ is selected from H, $C_{1-6}$alkyl, and $C_{1-6}$haloalkyl;

$R^7$ is selected from $C_{1-6}$alkyl or $-C_{1-6}$alkyl-$N(R^{14})_2$;

each $R^8$ is independently selected from halogen, $-CN$, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, $-OR^{10}$, $-SR^{10}$, $-N(R^{10})_2$, $-C(O)OR^{10}$, $-C(O)N(R^{10})_2$, $-OC(O)N(R^{10})_2$, $-N(R^{11})C(O)N(R^{10})_2$, $-N(R^{11})C(O)OR^{10}$, $-N(R^{11})C(O)R^{12}$, $-N(R^{11})S(O)_2R^{12}$, $-C(O)R^{12}$, $-S(O)R^{12}$, $-S(O)_2R^{12}$, $-S(O)_2N(R^{10})_2$, and $-OC(O)R^{12}$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{13}$;

$R^9$ is selected from H, $C_{1-6}$alkyl, and $C_6$haloalkyl;

each $R^{10}$ is independently selected from H, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl; each $R^{11}$ is independently selected from H, $C_{1-6}$alkyl, and $C_{1-6}$haloalkyl;

each $R^{12}$ is independently selected from $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{13}$;

each $R^{13}$ is independently selected from halogen, $-CN$, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —OR$^{15}$, —SR$^{15}$, —N(R$^{16}$)(R$^{17}$), —C(O)OR$^{16}$, —C(O)N(R$^{16}$)(R$^{17}$), —C(O)C(O)N(R$^{16}$)(R$^{17}$), —OC(O)N(R$^{16}$)(R$^{17}$), —N(R$^{18}$)C(O)N(R$^{16}$)(R$^{17}$), —N(R$^{18}$)C(O)OR$^{19}$, —N(R$^{18}$)C(O)R$^{19}$, —N(R$^{18}$)S(O)$_2$R$^{19}$, —C(O)R$^{19}$, —S(O)$_2$R$^{19}$, —S(O)$_2$N(R$^{16}$)(R$^{17}$), and —OC(O)R$^{19}$, wherein C$_{1-6}$alkyl, C$_{2-6}$alkenyl, C$_{2-6}$alkynyl, C$_{3-6}$cycloalkyl, —CH$_2$—C$_{3-6}$cycloalkyl, C$_{2-9}$heterocycloalkyl, —CH$_2$—C$_{2-9}$heterocycloalkyl, C$_{6-10}$aryl, —CH$_2$—C$_{6-10}$aryl, and C$_{1-9}$heteroaryl are optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{15}$, —SR$^{15}$, —N(R$^{15}$)$_2$, —C(O)OR$^{15}$, —C(O)N(R$^{15}$)$_2$, —C(O)C(O)N(R$^{15}$)$_2$, —OC(O)N(R$^{15}$)$_2$, —N(R$^{16}$)C(O)N(R$^{15}$)$_2$, —N(R$^{16}$)C(O)OR$^{15}$, —N(R$^{16}$)C(O)R$^{17}$, —N(R$^{16}$)S(O)$_2$R$^{17}$, —C(O)R$^{17}$, —S(O)$_2$R$^{17}$, —S(O)$_2$N(R$^{15}$)$_2$, and —OC(O)R$^{17}$;

each R$^{14}$ is independently selected from H, C$_{1-6}$alkyl, and C$_{1-6}$haloalkyl;

each R$^{15}$ is independently selected from H, C$_{1-6}$alkyl, C$_{1-6}$haloalkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl;

each R$^{16}$ is independently selected from H and C$_{1-6}$alkyl;

each R$^{17}$ is selected from C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl;

each R$^{18}$ is independently selected from H and C$_{1-6}$alkyl;

each R$^{19}$ is selected from C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl; and n is 0, 1, 2, 3, or 4;

or a pharmaceutically acceptable salt or solvate thereof.

In some embodiments is a compound of Formula (I), or a pharmaceutically acceptable salt or solvate thereof:

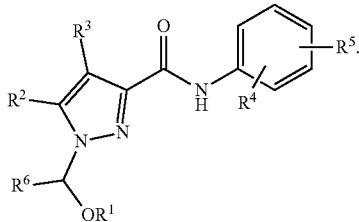

Formula (I)

In some embodiments is a compound of Formula (II), or a pharmaceutically acceptable salt or solvate thereof:

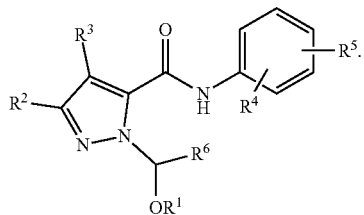

Formula (II)

In some embodiments is a compound of Formula (I) or (II), or a pharmaceutically acceptable salt or solvate thereof, wherein R$^1$ is

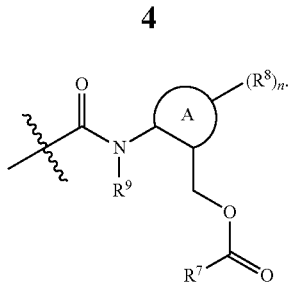

In some embodiments is a compound of Formula (Ib), or a pharmaceutically acceptable salt or solvate thereof:

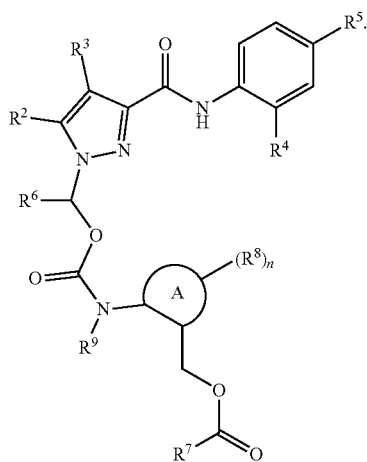

Formula (Ib)

In some embodiments is a compound of Formula (IIb), or a pharmaceutically acceptable salt or solvate thereof:

Formula (IIb)

In some embodiments is a compound of Formula (I), (Ib), (II), or (Ib), or a pharmaceutically acceptable salt or solvate thereof, wherein Ring A is C$_{2-9}$heteroaryl. In some embodiments is a compound of Formula (I), (Ib), (II), or (IIb), or a pharmaceutically acceptable salt or solvate thereof, wherein Ring A is C$_{2-9}$heteroaryl selected from oxazolyl, thiazolyl, pyrazolyl, furanyl, thienyl, pyrrolyl, imidazolyl, isoxazolyl, isothiazolyl, pyridinyl, pyrimidinyl, pyrazinyl, and pyridazinyl. In some embodiments is a compound of Formula (I), (Ib), (II), or (IIb), or a pharmaceutically acceptable salt or solvate thereof, wherein Ring A is $C_{2-9}$heteroaryl selected from pyridinyl, pyrimidinyl, pyrazinyl, and pyridazinyl. In some embodiments is a compound of Formula (I), (Ib), (II), or (IIb), or a pharmaceutically acceptable salt or solvate thereof, wherein Ring A is pyridinyl. In some embodiments is a compound of Formula (I), (Ib), (II), or (IIb), or a pharmaceutically acceptable salt or solvate thereof, wherein Ring A is phenyl. In some embodiments is a compound of Formula (I), (Ib), (II), or (IIb), or a pharmaceutically acceptable salt or solvate thereof, wherein $R^9$ is $C_{1-6}$alkyl.

In some embodiments is a compound of Formula (I) or (II), or a pharmaceutically acceptable salt or solvate thereof, wherein $R^1$ is

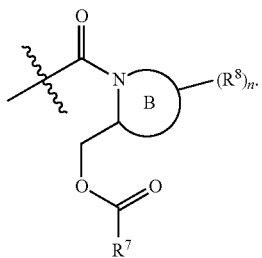

In some embodiments is a compound of Formula (I) or (II), or a pharmaceutically acceptable salt or solvate thereof, wherein Ring B is $C_{2-9}$heteroaryl. In some embodiments is a compound of Formula (I) or (II), or a pharmaceutically acceptable salt or solvate thereof, wherein Ring B is $C_{2-9}$heteroaryl selected from pyrazolyl, pyrrolyl, and imidazolyl. In some embodiments is a compound of Formula (I) or (II), or a pharmaceutically acceptable salt or solvate thereof, wherein Ring B is $C_{2-9}$heterocycloalkyl. In some embodiments is a compound of Formula (I) or (II), or a pharmaceutically acceptable salt or solvate thereof, wherein Ring B is $C_{2-9}$heteroaryl selected from pyrrolidinyl, piperidinyl, morpholinyl, and piperazinyl.

In some embodiments is a compound of Formula (I), (Ib), (II), or (Ib), or a pharmaceutically acceptable salt or solvate thereof, wherein $R^8$ is independently selected from halogen and unsubstituted $C_{1-6}$alkyl. In some embodiments is a compound of Formula (I), (Ib), (II), or (IIb), or a pharmaceutically acceptable salt or solvate thereof, wherein n is 0, 1, or 2. In some embodiments is a compound of Formula (I), (Ib), (II), or (IIb), or a pharmaceutically acceptable salt or solvate thereof, wherein n is 0.

In some embodiments is a compound of Formula (I) or (II), or a pharmaceutically acceptable salt or solvate thereof, wherein $R^1$ is $-C(O)N(R^9)C_{2-6}$alkyl-$OC(O)R^7$.

In some embodiments is a compound of Formula (I), (Ib), (II), or (IIb), or a pharmaceutically acceptable salt or solvate thereof, wherein $R^7$ is $C_{1-6}$alkyl. In some embodiments is a compound of Formula (I), (Ib), (II), or (IIb), or a pharmaceutically acceptable salt or solvate thereof, wherein $R^7$ is $-C_{1-6}$alkyl-$N(R^{14})_2$.

In some embodiments is a compound of Formula (I) or (II), or a pharmaceutically acceptable salt or solvate thereof, wherein $R^1$ is $-P(O)(OH)_2$.

In some embodiments is a compound of Formula (Ia), or a pharmaceutically acceptable salt or solvate thereof:

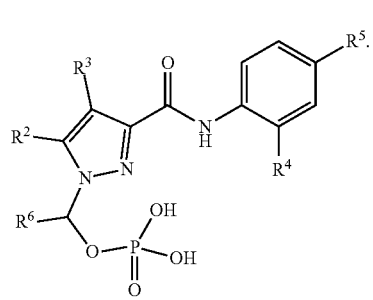

In some embodiments is a compound of Formula (IIa), or a pharmaceutically acceptable salt or solvate thereof:

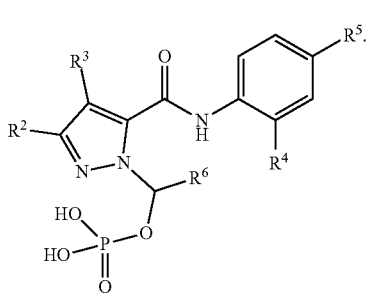

In some embodiments is a compound of Formula (I), (Ia), (Ib), (II), (IIa), or (IIb), or a pharmaceutically acceptable salt or solvate thereof, wherein $R^2$, $R^3$, $R^4$, and $R^5$ are each independently selected from H, halogen, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{13}$. In some embodiments is a compound of Formula (I), (Ia), (Ib), (II), (IIa), or (IIb), or a pharmaceutically acceptable salt or solvate thereof, wherein $R^2$, $R^3$, $R^4$, and $R^5$ are each independently selected from H, halogen, and $C_{1-6}$alkyl optionally substituted with one, two, or three $R^{13}$. In some embodiments is a compound of Formula (I), (Ia), (Ib), (II), (IIa), or (IIb), or a pharmaceutically acceptable salt or solvate thereof, wherein $R^2$, $R^3$, $R^4$, and $R^5$ are each independently selected from H and halogen. In some embodiments is a compound of Formula (I), (Ia), (Ib), (II), (IIa), or (IIb), or a pharmaceutically acceptable salt or solvate thereof, wherein $R^2$, $R^3$, $R^4$, and $R^5$ are each independently halogen. In some embodiments is a compound of Formula (I), (Ia), (Ib), (II), (IIa), or (IIb), or a pharmaceutically acceptable salt or solvate thereof, wherein $R^6$ is H. In some embodiments is a compound of Formula (I), (Ia), (Ib), (II), (IIa), or (IIb), or a pharmaceutically acceptable salt or solvate thereof, wherein $R^6$ is $C_{1-6}$alkyl.

In another aspect described herein is a pharmaceutical composition comprising a compound of Formula (I), (Ia), (Ib), (II), (IIa), or (IIb), or a pharmaceutically acceptable salt or solvate thereof, and at least one pharmaceutically acceptable excipient.

Also described herein is a method of treating an eosinophilic airway disease in a mammal in need thereof, comprising administering to the mammal a therapeutically effective amount of a compound of Formula (I), (Ia), (Ib), (II), (IIa), or (IIb), or a pharmaceutically acceptable salt or solvate thereof. In some embodiments is a method of treating an eosinophilic airway disease in a mammal in need thereof, comprising administering to the mammal a therapeutically effective amount of a compound of Formula (I), (Ia), (Ib), (II), (IIa), or (IIb), or a pharmaceutically acceptable salt or solvate thereof, wherein the eosinophilic airway disease is selected from asthma, chronic rhinosinusitis, nasal polyposis, and allergic rhinitis.

Also described herein is a method of treating an eosinophilic disease of the gastro-intestinal tract in a mammal in need thereof, comprising administering to the mammal a therapeutically effective amount of a compound of Formula (I), (Ia), (Ib), (II), (IIa), or (Ib), or a pharmaceutically acceptable salt or solvate thereof. In some embodiments is a method of treating an eosinophilic disease of the gastro-intestinal tract in a mammal in need thereof, comprising administering to the mammal a therapeutically effective amount of a compound of Formula (I), (Ia), (Ib), (II), (IIa), or (IIb), or a pharmaceutically acceptable salt or solvate thereof, wherein the eosinophilic disease of the gastro-intestinal tract is selected from eosinophilic esophagitis and eosinophilic gastritis.

BRIEF DESCRIPTION OF THE DRAWINGS

A better understanding of the features and advantages of the present subject matter will be obtained by reference to the following detailed description that sets forth illustrative embodiments and the accompanying drawings.

DETAILED DESCRIPTION OF THE INVENTION

Figure 1:
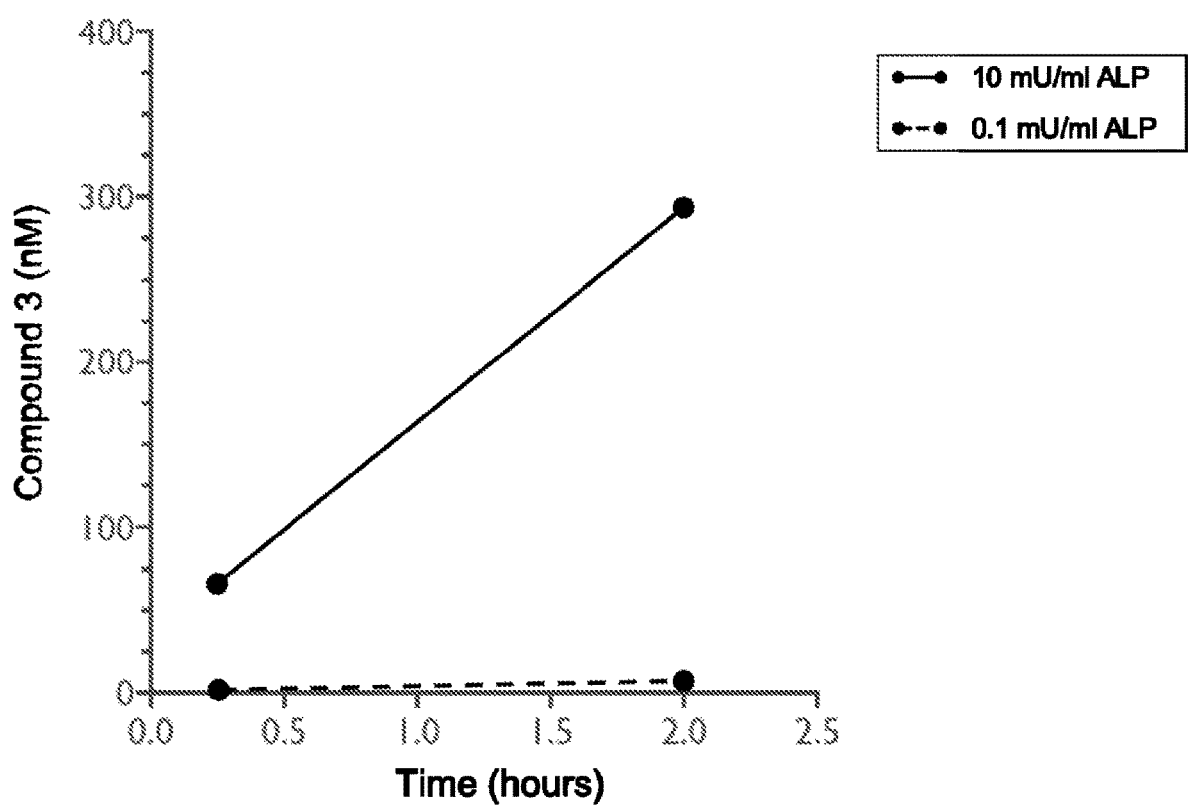
FIG. 1 depicts levels of compound 3 following alkaline phosphatase treatment of compound 5, as analyzed by LC-MS/MS.

ALOX15 is one of five (ALOX5/12/12B/15/15B) human lipoxygenases and is involved in the metabolism of arachidonic acid and other polyunsaturated fatty acid substrates. 15-HETE is its major arachidonic acid-derived metabolite, which is then further metabolized to eoxins, 5-oxo-15-hydroxy-ETE and other metabolites. ALOX15 metabolites are largely pro-inflammatory and have been shown to induce airway epithelial injury and promote goblet cell hyperplasia/mucus hypersecretion (15-HETE), increase vascular permeability (eoxin $C_4$) and are potent eosinophil chemoattractants (5-oxo-15-hydroxy-ETE). ALOX15 is highly expressed in circulating blood eosinophils, airway epithelial cells and esophageal squamous epithelial cells and is induced in vitro by IL-13, a central mediator of the Th2 response. Accordingly, therapies as described herein designed to inhibit the production of ALOX15 protein delivered locally to the nasal epithelium, via inhalation to the airway, orally or systemically, can be efficacious in treating eosinophilic diseases of the upper and lower airway, including nasal polyposis, chronic rhinosinusitis, allergic rhinitis and asthma; and eosinophilic diseases of the gastro-intestinal tract, including eosinophilic esophagitis and eosinophilic gastroenteritis.

Definitions

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range varies between 1% and 15% of the stated number or numerical range. The term "comprising" (and related terms such as "comprise" or "comprises" or "having" or "including") is not intended to exclude that which in other certain embodiments, for example, an embodiment of any composition of matter, composition, method, or process, or the like, described herein, may "consist of" or "consist essentially of" the described features.

As used in the specification and appended claims, unless specified to the contrary, the following terms have the meaning indicated below.

As used herein, $C_1$-$C_x$ includes $C_1$-$C_2$, $C_1$-$C_3$ ... $C_1$-$C_x$. $C_1$-$C_x$ refers to the number of carbon atoms that make up the moiety to which it designates (excluding optional substituents).

"Amino" refers to the —$NH_2$ radical.
"Cyano" refers to the —CN radical.
"Nitro" refers to the —$NO_2$ radical.
"Oxa" refers to the —O— radical.
"Oxo" refers to the =O radical.
"Thioxo" refers to the =S radical.
"Imino" refers to the =N—H radical.
"Oximo" refers to the =N—OH radical.

"Alkyl" or "alkylene" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to ten carbon atoms (e.g., $C_1$-$C_{10}$ alkyl). In certain embodiments, an alkyl comprises one to eight carbon atoms (e.g., $C_1$-$C_8$ alkyl). In other embodiments, an alkyl comprises one to six carbon atoms (e.g., $C_1$-$C_6$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl(n-propyl), 1-methylethyl(iso-propyl), 1-butyl(n-butyl), 1-methylpropyl(sec-butyl), 2-methylpropyl(iso-butyl), 1,1-dimethylethyl(tert-butyl), and 1-pentyl(n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —$OR^a$, —$SR^a$, —$OC(O)R^a$, —$N(R^a)_2$, —$C(O)R^a$, —$C(O)OR^a$, —$C(O)N(R^a)_2$, —$N(R^a)C(O)OR^f$, —$OC(O)$—$NR^aR^f$, —$N(R^a)C(O)R^f$, —$N(R^a)S(O)_tR^f$ (where t is 1 or 2), —$S(O)_tOR^a$ (where t is 1 or 2), —$S(O)_tR^f$ (where t is 1 or 2), and —$S(O)_tN(R^a)_2$ (where t is 1 or 2), where each $R^a$ is independently hydrogen, alkyl, fluoroalkyl, cycloalkyl, aryl, aralkyl, heterocycloalkyl, heteroaryl, or heteroarylalkyl, and each $R^f$ is independently alkyl, fluoroalkyl, cycloalkyl, aryl, aralkyl, heterocycloalkyl, heteroaryl, or heteroarylalkyl.

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In other embodiments, an alkenyl comprises two to ten carbon atoms. In certain embodiments, an alkenyl comprises two to eight carbon atoms. In other embodiments, an alkenyl comprises two to six carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —$OR^a$, —$SR^a$, —$OC(O)$—$R^f$, —$N(R^a)_2$, —$C(O)R^a$, —$C(O)OR^a$, —$C(O)N(R^a)_2$, —$N(R^a)C(O)OR^f$, —$OC(O)$-$nR^aR^f$, —$N(R^a)C(O)R^f$, —$N(R^a)S(O)_tR^f$ (where t is 1 or 2), —$S(O)_tOR^a$ (where t is 1 or 2), —$S(O)_tR^f$ (where t is 1 or 2), and —$S(O)_tN(R^a)_2$ (where t is 1 or 2), where each $R^a$ is independently hydrogen, alkyl, fluoroalkyl, cycloalkyl, aryl, aralkyl, heterocycloalkyl, heteroaryl, or heteroarylalkyl, and each $R^f$ is independently alkyl, fluoroalkyl, cycloalkyl, aryl, aralkyl, heterocycloalkyl, heteroaryl, or heteroarylalkyl.

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to ten carbon atoms. In certain embodiments, an alkynyl comprises two to eight carbon atoms. In other embodiments, an alkynyl has two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —$OR^a$, —$SR^a$, —$OC(O)R^a$, —$N(R^a)_2$, —$C(O)R^a$, —$C(O)OR^a$, —$C(O)N(R^a)_2$, —$N(R^a)C(O)OR^f$, —$OC(O)$—$NR^aR^f$, —$N(R^a)C(O)R^f$, —$N(R^a)S(O)_tR^f$ (where t is 1 or 2), —$S(O)_tOR^a$ (where t is 1 or 2), —$S(O)_tR^f$ (where t is 1 or 2), and —$S(O)_tN(R^a)_2$ (where t is 1 or 2), where each $R^a$ is independently hydrogen, alkyl, fluoroalkyl, cycloalkyl, aryl, aralkyl, heterocycloalkyl, heteroaryl, or heteroarylalkyl, and each $R^f$ is independently alkyl, fluoroalkyl, cycloalkyl, aryl, aralkyl, heterocycloalkyl, heteroaryl, or heteroarylalkyl.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from six to eighteen carbon atoms, where at least one of the rings in the ring system is fully unsaturated, i.e., it contains a cyclic, delocalized (4n+2) 7-electron system in accordance with the Hückel theory. The ring system from which aryl groups are derived include, but are not limited to, groups such as benzene, fluorene, indane, indene, tetralin, and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, aryl, aralkyl, alkenyl, aralkynyl, cycloalkyl, heterocycloalkyl, heteroaryl, heteroarylalkyl, —$R^b$—$OR^a$, —$R^b$—$OC(O)$—$R^a$, —$R^b$—$OC(O)$—$OR^a$, —$R^b$—$OC(O)$—$N(R^a)_2$, —$R^b$—$N(R^a)_2$, —$R^b$—$C(O)R^a$, —$R^b$—$C(O)OR^a$, —$R^b$—$C(O)N(R^a)_2$, —$R^b$—O—$R^c$—$C(O)N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)OR^a$ (where t is 1 or 2), —R—$S(O)_tR^a$ (where t is 1 or 2) and —R—$S(O)_tN(R^a)_2$ (where t is 1 or 2), where each $R^a$ is independently hydrogen, alkyl, fluoroalkyl, cycloalkyl, cycloalkylalkyl, aryl (optionally substituted with one or more halo groups), aralkyl, heterocycloalkyl, heteroaryl or heteroarylalkyl, each $R^b$ is independently a direct bond or a straight or branched alkylene or alkenylene chain, and $R^c$ is a straight or branched alkylene or alkenylene chain.

"Aryloxy" refers to a radical bonded through an oxygen atom of the formula —O-aryl, where aryl is as defined above.

"Aralkyl" refers to a radical of the formula —$R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkyloxy" refers to a radical bonded through an oxygen atom of the formula —O— aralkyl, where aralkyl is as defined above.

"Aralkenyl" refers to a radical of the formula —R$^d$-aryl where R$^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —R$^e$-aryl where R$^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Cycloalkyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a cycloalkyl comprises three to ten carbon atoms. In other embodiments, a cycloalkyl comprises five to seven carbon atoms. The cycloalkyl is attached to the rest of the molecule by a single bond. Cycloalkyls are saturated, (i.e., containing single C—C bonds only) or partially unsaturated (i.e., containing one or more double bonds or triple bonds.) Examples of monocyclic cycloalkyls include, e.g., cyclopropyl, cyclobutyl, cyclopentyl, cyclohexyl, cycloheptyl, and cyclooctyl. In certain embodiments, a cycloalkyl comprises three to eight carbon atoms (e.g., $C_3$-$C_8$ cycloalkyl). In other embodiments, a cycloalkyl comprises three to seven carbon atoms (e.g., $C_3$-$C_7$ cycloalkyl). In other embodiments, a cycloalkyl comprises three to six carbon atoms (e.g., $C_3$-$C_6$ cycloalkyl). In other embodiments, a cycloalkyl comprises three to five carbon atoms (e.g., $C_3$-$C_5$ cycloalkyl). In other embodiments, a cycloalkyl comprises three to four carbon atoms (e.g., $C_3$-$C_4$ cycloalkyl). A partially unsaturated cycloalkyl is also referred to as "cycloalkenyl." Examples of monocyclic cycloalkenyls include, e.g., cyclopentenyl, cyclohexenyl, cycloheptenyl, and cyclooctenyl. Polycyclic cycloalkyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "cycloalkyl" is meant to include cycloalkyl radicals optionally substituted by one or more substituents independently selected from alkyl, alkenyl, alkynyl, halo, fluoroalkyl, cyano, nitro, aryl, aralkyl, aralkenyl, aralkynyl, cycloalkyl, heterocycloalkyl, heteroaryl, heteroarylalkyl, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)OR$^a$ (where t is 1 or 2), —R$^b$—S(O)R$^a$ (where t is 1 or 2) and —R$^b$—S(O)$_t$N(R$^a$)$_2$ (where t is 1 or 2), where each R$^a$ is independently hydrogen, alkyl, fluoroalkyl, cycloalkyl, cycloalkylalkyl, aryl (optionally substituted with one or more halo groups), aralkyl, heterocycloalkyl, heteroaryl or heteroarylalkyl, each R$^b$ is independently a direct bond or a straight or branched alkylene or alkenylene chain, and R$^c$ is a straight or branched alkylene or alkenylene chain.

"Halo" or "halogen" refers to bromo, chloro, fluoro, or iodo substituents.

"Haloalkyl" refers to an alkyl radical, as defined above, that is substituted by one or more halo radicals, as defined above.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. The alkyl part of the fluoroalkyl radical are optionally substituted as defined above for an alkyl group.

"Haloalkoxy" refers to an alkoxy radical, as defined above, that is substituted by one or more halo radicals, as defined above.

"Heterocycloalkyl" refers to a stable 3- to 18-membered non-aromatic ring radical that comprises two to twelve carbon atoms and from one to six heteroatoms selected from nitrogen, oxygen, and sulfur. Unless stated otherwise specifically in the specification, the heterocycloalkyl radical is a monocyclic, bicyclic, tricyclic, or tetracyclic ring system, which include fused, spiro, or bridged ring systems. The heteroatoms in the heterocycloalkyl radical are optionally oxidized. One or more nitrogen atoms, if present, are optionally quaternized. The heterocycloalkyl radical is partially or fully saturated. In some embodiments, the heterocycloalkyl is attached to the rest of the molecule through any atom of the ring(s). Examples of such heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocycloalkyl" is meant to include heterocycloalkyl radicals as defined above that are optionally substituted by one or more substituents selected from alkyl, alkenyl, alkynyl, halo, fluoroalkyl, oxo, thioxo, cyano, nitro, aryl, aralkyl, aralkenyl, aralkynyl, cycloalkyl, heterocycloalkyl, heteroaryl, heteroarylalkyl, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)OR$^a$ (where t is 1 or 2), —R$^b$—S(O)R$^a$ (where t is 1 or 2) and —R$^b$—S(O)$_t$N(R$^a$)$_2$ (where t is 1 or 2), where each R$^a$ is independently hydrogen, alkyl, fluoroalkyl, cycloalkyl, cycloalkylalkyl, aryl, aralkyl, heterocycloalkyl, heteroaryl or heteroarylalkyl, each R$^b$ is independently a direct bond or a straight or branched alkylene or alkenylene chain, and R$^c$ is a straight or branched alkylene or alkenylene chain.

"Heteroaryl" refers to a radical derived from a 5- to 18-membered aromatic ring radical that comprises one to seventeen carbon atoms and from one to six heteroatoms selected from nitrogen, oxygen, and sulfur. As used herein, the heteroaryl radical is a monocyclic, bicyclic, tricyclic, or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Unless stated otherwise specifically in the specification, the term "heteroaryl" is meant to include heteroaryl radicals as defined above that are optionally substituted by one or more substituents selected from alkyl, alkenyl, alkynyl, halo, haloalkyl, oxo, thioxo, cyano, nitro, aryl, aralkyl, aralkenyl, aralkynyl, cycloalkyl, heterocycloalkyl, heteroaryl, heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$OR^a$ (where t is 1 or 2), —$R^b$—S(O)$_t$$R^a$ (where t is 1 or 2) and —$R^b$—S(O)$_t$N($R^a$)$_2$ (where t is 1 or 2), where each $R^a$ is independently hydrogen, alkyl, fluoroalkyl, cycloalkyl, cycloalkylalkyl, aryl, aralkyl, heterocycloalkyl, heteroaryl, or heteroarylalkyl, each $R^b$ is independently a direct bond or a straight or branched alkylene or alkenylene chain, and $R^c$ is a straight or branched alkylene or alkenylene chain.

nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

A "tautomer" refers to a molecule wherein a proton shift from one atom of a molecule to another atom of the same molecule is possible. In certain embodiments, the compounds presented herein exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

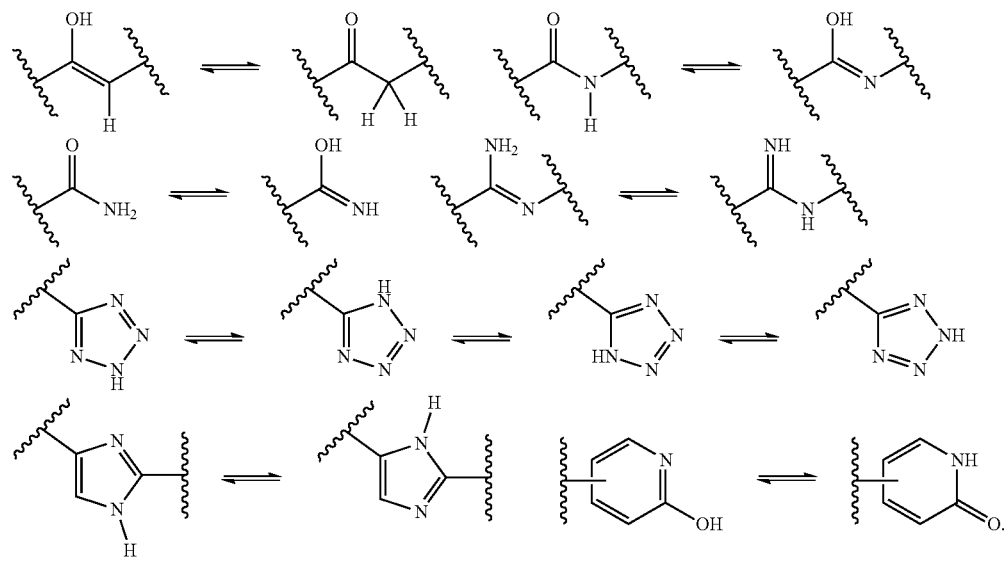

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroaryloxy" refers to radical bonded through an oxygen atom of the formula —O— heteroaryl, where heteroaryl is as defined above.

"Heteroarylalkyl" refers to a radical of the formula —R-heteroaryl, where R is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—R-heteroaryl, where $R^c$ is an alkylene chain as defined above. If the heteroaryl is a "Optional" or "optionally" means that a subsequently described event or circfshia e may or may not occur and that the description includes instances when the event or circumstance occurs and instances in which it does not. The term "optionally substituted" or "substituted" means that the referenced group may be substituted with one or more additional group(s) individually and independently selected from alkyl, cycloalkyl, aryl, heteroaryl, heterocycloalkyl, —OH, alkoxy, aryloxy, alkylthio, arylthio, alkylsulfoxide, arylsulfoxide, alkylsulfone, arylsulfone, —CN, alkyne, $C_1$-$C_6$alkylalkyne, halo, acyl, acyloxy, —$CO_2$H, —$CO_2$—alkyl, nitro, haloalkyl, fluoroalkyl, and amino, including mono- and di-substituted amino groups (e.g. —$NH_2$, —NHR, —N(R)$_2$), and the protected derivatives thereof. By way of example, an optional substituent may be $L^s$$R^s$, wherein each $L^s$ is independently selected from a bond, —O—, —C(=O)—, —S—, —S(=O)—, —S(=O)$_2$—, —NH—, —NHC(O)—, —C(O)NH—, S(=O)$_2$NH—, —NHS(=O)$_2$, —OC(O)NH—, —NHC(O)O—, —($C_1$-$C_6$alkyl)-, or —($C_2$-$C_6$alkenyl)-; and each $R^s$ is independently selected from among H, ($C_1$-$C_6$alkyl), ($C_3$-$C_8$cycloalkyl), aryl, heteroaryl, and heterocycloalkyl.

"Pharmaceutically acceptable salt" includes both acid and base addition salts. A pharmaceutically acceptable salt of any one of the compounds described herein is intended to encompass any and all pharmaceutically suitable salt forms.

Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science,* 66:1-19 (1997)). Acid addition salts of basic compounds are prepared by contacting the free base forms with a sufficient amount of the desired acid to produce the salt.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. In some embodiments, pharmaceutically acceptable base addition salts are formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins, and the like. See Berge et al., supra.

As used herein, "treatment" or "treating" or "palliating" or "ameliorating" are used interchangeably herein. These terms refer to an approach for obtaining beneficial or desired results including, but not limited to, therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are administered to a patient at risk of developing a particular disease, or to a patient reporting one or more of the physiological symptoms of a disease, even though a diagnosis of this disease has not been made.

A "prodrug" refers to an agent that is converted into the parent drug in vivo. Prodrugs are often useful because, in some situations, they are easier to administer than the parent drug. They are, for instance, bioavailable by oral administration whereas the parent is not. The prodrug may be a substrate for a transporter. Further or alternatively, the prodrug also has improved solubility in pharmaceutical compositions over the parent drug. In some embodiments, the design of a prodrug increases the effective water solubility. An example, without limitation, of a prodrug is a compound described herein, which is administered as an phosphonooxymethyl derivative (the "prodrug"), but then is metabolically hydrolyzed to provide the active entity. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound. In some embodiments, compounds described herein are cleaved by an esterase. In some embodiments, compounds described herein are cleaved by a phosphatase.

Prodrugs described herein include, but are not limited to, esters, ethers, carbonates, thiocarbonates, N-acyl derivatives, N-acyloxyalkyl derivatives, quaternary derivatives of tertiary amines, N-Mannich bases, Schiff bases, amino acid conjugates, phosphate esters, sulfonamides, amides, phosphoramidates and sulfonate esters. See for example Design of Prodrugs, Bundgaard, A. Ed., Elseview, 1985 and Method in Enzymology, Widder, K. et al., Ed.; Academic, 1985, vol. 42, p. 309-396; Bundgaard, H. "Design and Application of Prodrugs" in A Textbook of Drug Design and Development, Krosgaard-Larsen and H. Bundgaard, Ed., 1991, Chapter 5, p. 113-191; and Bundgaard, H., Advanced Drug Delivery Review, 1992, 8, 1-38, each of which is incorporated herein by reference.

Compounds

The compounds of Formula (I), (Ia), (Ib), (II), (IIa), (IIb), (III), (IIIa), or (IIIb) described herein are prodrugs of ALOX-15 inhibitors. In some embodiments, the compounds of Formula (I), (Ia), (Ib), (II), (IIa), (IIb), (III), (IIIa), or (IIIb) described herein, and pharmaceutical compositions comprising these compounds, are useful for the treatment of an eosinophilic airway disease including, but not limited to, asthma, chronic rhinosinusitis, nasal polyposis and allergic rhinitis. In some embodiments, the compounds of Formula (I), (Ia), (Ib), (II), (IIa), (IIb), (III), (IIIa), or (IIIb) described herein, and pharmaceutical compositions comprising these compounds, are useful for the treatment of an eosinophilic disease of the gastro-intestinal tract including, but not limited to, eosinophilic esophagitis and eosinophilic gastritis.

In some embodiments is a compound of Formula (I):
wherein

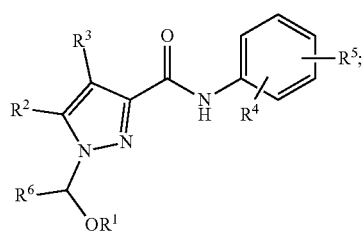

Formula (I)

$R^1$ is —P(O)(OH)$_2$, —C(O)N(R$^9$)C$_{2-6}$alkyl-OC(O)R$^7$,

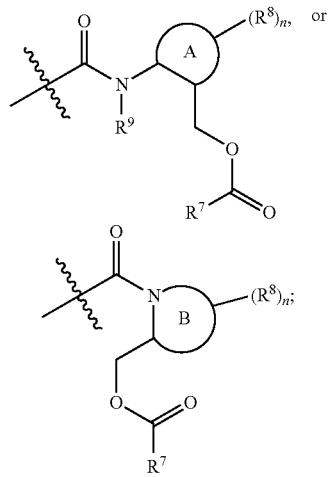

Ring A is selected from C$_{3-6}$cycloalkyl, C$_{2-9}$heterocycloalkyl, C$_{6-10}$aryl, and C$_{2-9}$heteroaryl;

Ring B is selected from C$_{2-9}$heterocycloalkyl and C$_{2-9}$heteroaryl;

$R^2$, $R^3$, $R^4$, and $R^5$ are each independently selected from H, halogen, —CN, C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, C$_{1-9}$heteroaryl, —OR$^{10}$, —SR$^{10}$, —N(R$^{10}$)$_2$, —C(O)OR$^{10}$, —C(O)N(R$^{10}$)$_2$, —OC(O)N(R$^{10}$)$_2$, —N(R$^{11}$)C(O)N(R$^{10}$)$_2$, —N(R$^{11}$)C(O)OR$^{10}$, —N(R$^{11}$)C(O)R$^{12}$, —N(R$^{11}$)S(O)$_2$R$^{12}$, —C(O)R$^{12}$, —S(O)R$^{12}$, —S(O)$_2$R$^{12}$, —S(O)$_2$N(R$^{11}$)$_2$, and —OC(O)R$^{12}$, wherein C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three R$^{13}$;

$R^6$ is selected from H, C$_{1-6}$alkyl, and C$_{1-6}$haloalkyl;

$R^7$ is selected from C$_{1-6}$alkyl or —C$_{1-6}$alkyl-N(R$^{14}$)$_2$;

each $R^8$ is independently selected from halogen, —CN, C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, C$_{1-9}$heteroaryl, —OR$^{10}$, —SR$^{10}$, —N(R$^{10}$)$_2$, —C(O)OR$^{10}$, —C(O)N(R$^{10}$)$_2$, —OC(O)N(R$^{10}$)$_2$, —N(R$^{11}$)C(O)N(R$^{10}$)$_2$, —N(R$^{11}$)C(O)OR$^{10}$, —N(R$^{11}$)C(O)R$^{12}$, —N(R$^{11}$)S(O)$_2$R$^{12}$, —C(O)R$^{12}$, —S(O)R$^{12}$, —S(O)$_2$R$^{12}$, —S(O)$_2$N(R$^{10}$)$_2$, and —OC(O)R$^{12}$, wherein C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three R$^{13}$;

$R^9$ is selected from H, C$_{1-6}$alkyl, and C$_6$haloalkyl;

each $R^{10}$ is independently selected from H, C$_{1-6}$alkyl, C$_{1-6}$haloalkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl;

each $R^{11}$ is independently selected from H, C$_{1-6}$alkyl, and C$_{1-6}$haloalkyl;

each $R^{12}$ is independently selected from C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl, wherein C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three R$^{13}$;

each $R^{13}$ is independently selected from halogen, —CN, C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, C$_{1-9}$heteroaryl, —OR$^{15}$, —SR$^{15}$, —N(R$^{16}$)(R$^{17}$), —C(O)OR$^{16}$, —C(O)N(R$^{16}$)(R$^{17}$), —C(O)C(O)N(R$^{16}$)(R$^{17}$), —OC(O)N(R$^{16}$)(R$^{17}$), —N(R$^{18}$)C(O)N(R$^{16}$)(R$^{17}$), —N(R$^{18}$)C(O)OR$^{19}$, —N(R$^{18}$)C(O)R$^{19}$, —N(R$^{18}$)S(O)$_2$R$^{19}$, —C(O)R$^{19}$, —S(O)$_2$R$^{19}$, —S(O)$_2$N(R$^{16}$)(R$^{17}$), and —OC(O)R$^{19}$, wherein C$_{1-6}$alkyl, C$_{2-6}$alkenyl, C$_{2-6}$alkynyl, C$_{3-6}$cycloalkyl, —CH$_2$—C$_{3-6}$cycloalkyl, C$_{2-9}$heterocycloalkyl, —CH$_2$—C$_{2-9}$heterocycloalkyl, C$_{6-10}$aryl, —CH$_2$—C$_{6-10}$aryl, and C$_{1-9}$ heteroaryl are optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{15}$, —SR$^{15}$, —N(R$^{15}$)$_2$, —C(O)OR$^{15}$, —C(O)N(R$^{15}$)$_2$, —C(O)C(O)N(R$^{15}$)$_2$, —OC(O)N(R$^{15}$)$_2$, —N(R$^{16}$)C(O)N(R$^{11}$)$_2$, —N(R$^{16}$)C(O)OR$^{11}$, —N(R$^{16}$)C(O)R$^{17}$, —N(R$^{16}$)S(O)$_2$R$^{17}$, —C(O)R$^{17}$, —S(O)$_2$R$^{17}$, —S(O)$_2$N(R$^{15}$)$_2$, and —OC(O)R$^{17}$;

each $R^{14}$ is independently selected from H, C$_{1-6}$alkyl, and C$_{1-6}$haloalkyl;

each $R^{15}$ is independently selected from H, C$_{1-6}$alkyl, C$_{1-6}$haloalkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl; each $R^{16}$ is independently selected from H and C$_{1-6}$alkyl;

each $R^{17}$ is selected from C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl;

each $R^{18}$ is independently selected from H and C$_{1-6}$alkyl;

each $R^{19}$ is selected from C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl; and n is 0, 1, 2, 3, or 4;

or a pharmaceutically acceptable salt or solvate thereof.

In some embodiments is a compound of Formula (I), or a pharmaceutically acceptable salt or solvate thereof, wherein $R^1$ is —P(O)(OH)$_2$.

In some embodiments is a compound of Formula (I), or a pharmaceutically acceptable salt or solvate thereof, wherein $R^1$ is —C(O)N(R$^9$)C$_{2-6}$alkyl-OC(O)R$^7$. In some embodiments is a compound of Formula (I), or a pharmaceutically acceptable salt or solvate thereof, wherein $R^1$ is —C(O)N(H)C$_{2-6}$alkyl-OC(O)R$^7$. In some embodiments is a compound of Formula (I), or a pharmaceutically acceptable salt or solvate thereof, wherein $R^1$ is —C(O)N(H)C$_{2-6}$alkyl-OC(O)R$^7$ and $R^7$ is C$_{1-6}$alkyl. In some embodiments is a compound of Formula (I), or a pharmaceutically acceptable salt or solvate thereof, wherein $R^1$ is —C(O)N(H)C$_{2-6}$alkyl-OC(O)R$^7$ and $R^7$ is —C$_{1-6}$ alkyl-N(R$^{14}$)$_2$. In some embodiments is a compound of Formula (I), or a pharmaceutically acceptable salt or solvate thereof, wherein $R^1$ is —C(O)N(H)C$_{2-6}$alkyl-OC(O)R$^7$ and $R^7$ is —C$_{1-6}$ alkyl-NH$_2$. In some embodiments is a compound of Formula (I), or a pharmaceutically acceptable salt or solvate thereof, wherein $R^1$ is —C(O)N(H)$C_{2-6}$alkyl-OC(O)$R^7$ and $R^7$ is —$C_{1-6}$ alkyl-N(H)$CH_3$. In some embodiments is a compound of Formula (I), or a pharmaceutically acceptable salt or solvate thereof, wherein $R^1$ is —C(O)N($CH_3$)$C_{2-6}$alkyl-OC(O)$R^7$. In some embodiments is a compound of Formula (I), or a pharmaceutically acceptable salt or solvate thereof, wherein $R^1$ is —C(O)N($CH_3$)$C_{2-6}$alkyl-OC(O)$R^7$ and $R^7$ is $C_{1-6}$alkyl. In some embodiments is a compound of Formula (I), or a pharmaceutically acceptable salt or solvate thereof, wherein $R^1$ is —C(O)N($CH_3$)$C_{2-6}$alkyl-OC(O)$R^7$ and $R^7$ is —$C_{1-6}$ alkyl-N($R^{14}$)$_2$. In some embodiments is a compound of Formula (I), or a pharmaceutically acceptable salt or solvate thereof, wherein $R^1$ is —C(O)N($CH_3$)$C_{2-6}$alkyl-OC(O)$R^7$ and $R^7$ is —$C_{1-6}$alkyl-$NH_2$. In some embodiments is a compound of Formula (I), or a pharmaceutically acceptable salt or solvate thereof, wherein $R^1$ is —C(O)N($CH_3$)$C_{2-6}$ alkyl-OC(O)$R^7$ and $R^7$ is —$C_{1-6}$alkyl-N(H)$CH_3$.

In some embodiments is a compound of Formula (I), or a pharmaceutically acceptable salt or solvate thereof, wherein $R^1$ is

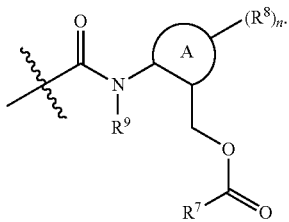

In some embodiments is a compound of Formula (I), or a pharmaceutically acceptable salt or solvate thereof, wherein $R^1$ is

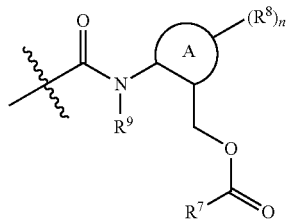

and Ring A is $C_{2-9}$heteroaryl. In some embodiments is a compound of Formula (I), or a pharmaceutically acceptable salt or solvate thereof, wherein $R^1$ is

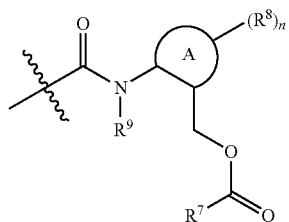

and Ring A is $C_{2-9}$heteroaryl selected from oxazolyl, thiazolyl, pyrazolyl, furanyl, thienyl, pyrrolyl, imidazolyl, isoxazolyl, isothiazolyl, pyridinyl, pyrimidinyl, pyrazinyl, and pyridazinyl. In some embodiments is a compound of Formula (I), or a pharmaceutically acceptable salt or solvate thereof, wherein $R^1$ is

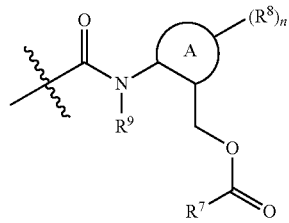

and Ring A is $C_{2-9}$heteroaryl selected from pyridinyl, pyrimidinyl, pyrazinyl, and pyridazinyl. In some embodiments is a compound of Formula (I), or a pharmaceutically acceptable salt or solvate thereof, wherein $R^1$ is

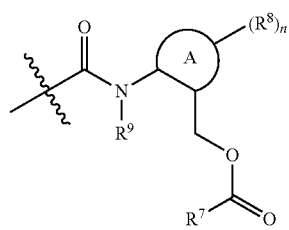

and Ring A is pyridinyl.

In some embodiments is a compound of Formula (I), or a pharmaceutically acceptable salt or solvate thereof, wherein $R^1$ is

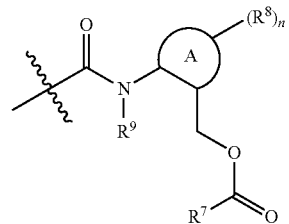

and Ring A is phenyl.

In some embodiments is a compound of Formula (I), or a pharmaceutically acceptable salt or solvate thereof, wherein $R^9$ is $C_{1-6}$alkyl.

In some embodiments is a compound of Formula (I), or a pharmaceutically acceptable salt or solvate thereof, wherein $R^1$ is

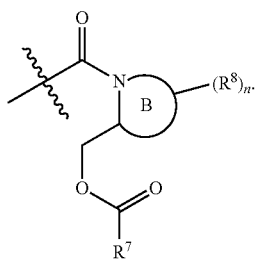

In some embodiments is a compound of Formula (I), or a pharmaceutically acceptable sa or solvate thereof, wherein $R^1$ is

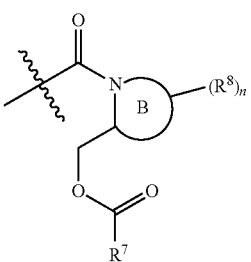

and Ring B is $C_{2-9}$heteroaryl. In some embodiments is a compound of Formula (I), or a pharmaceutically acceptable salt or solvate thereof, wherein $R^1$ is

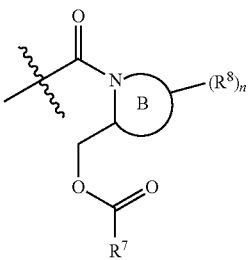

and Ring B is $C_{2-9}$heteroaryl selected from pyrazolyl, pyrrolyl, and imidazolyl.

In some embodiments is a compound of Formula (I), or a pharmaceutically acceptable salt or solvate thereof, wherein $R^1$ is

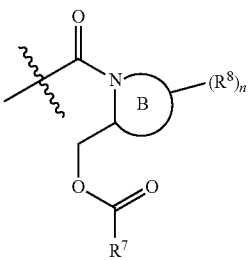

and Ring B is $C_{2-9}$heterocycloalkyl. In some embodiments is a compound of Formula (I), or a pharmaceutically acceptable salt or solvate thereof, wherein $R^1$ is

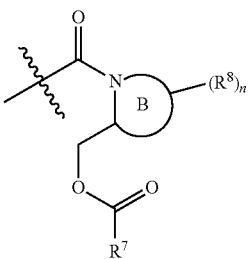

and Ring B is $C_{2-9}$heterocycloalkyl selected from pyrrolidinyl, piperidinyl, morpholinyl, and piperazinyl.

In some embodiments is a compound of Formula (I), or a pharmaceutically acceptable salt or solvate thereof, wherein n is 0, 1, or 2. In some embodiments is a compound of Formula (I), or a pharmaceutically acceptable salt or solvate thereof, wherein n is 2. In some embodiments is a compound of Formula (I), or a pharmaceutically acceptable salt or solvate thereof, wherein n is 1. In some embodiments is a compound of Formula (I), or a pharmaceutically acceptable salt or solvate thereof, wherein n is 0.

In some embodiments is a compound of Formula (I), or a pharmaceutically acceptable salt or solvate thereof, wherein each $R^8$ is independently selected from halogen and unsubstituted $C_{1-6}$alkyl. In some embodiments is a compound of Formula (I), or a pharmaceutically acceptable salt or solvate thereof, wherein n is 1 or 2 and each $R^8$ is independently selected from halogen and unsubstituted $C_{1-6}$alkyl. In some embodiments is a compound of Formula (I), or a pharmaceutically acceptable salt or solvate thereof, wherein n is 1 and $R^8$ is halogen. In some embodiments is a compound of Formula (I), or a pharmaceutically acceptable salt or solvate thereof, wherein n is 1 and $R^8$ is unsubstituted $C_{1-6}$alkyl.

In some embodiments is a compound of Formula (I), or a pharmaceutically acceptable salt or solvate thereof, wherein $R^2$, $R^3$, $R^4$, and $R^5$ are each independently selected from H, halogen, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{13}$. In some embodiments is a compound of Formula (I), or a pharmaceutically acceptable salt or solvate thereof, wherein $R^2$, $R^3$, $R^4$, and $R^5$ are each independently selected from H, halogen, and $C_{1-6}$ alkyl optionally substituted with one, two, or three $R^{13}$. In some embodiments is a compound of Formula (I), or a pharmaceutically acceptable salt or solvate thereof, wherein $R^2$, $R^3$, $R^4$, and $R^5$ are each independently selected from H, halogen, and unsubstituted $C_{1-6}$alkyl. In some embodiments is a compound of Formula (I), or a pharmaceutically acceptable salt or solvate thereof, wherein $R^2$, $R^3$, $R^4$, and $R^5$ are each independently selected from H and halogen. In some embodiments is a compound of Formula (I), or a pharmaceutically acceptable salt or solvate thereof, wherein $R^2$, $R^3$, $R^4$, and $R^5$ are each independently halogen.

In some embodiments is a compound of Formula (I), or a pharmaceutically acceptable salt or solvate thereof, wherein $R^2$, $R^3$, and $R^4$ are each —Cl and $R^5$ is —F. In some embodiments is a compound of Formula (I), or a pharmaceutically acceptable salt or solvate thereof, wherein $R^2$, $R^3$, and $R^5$ are each —Cl and $R^4$ is —F. In some embodiments is a compound of Formula (I), or a pharmaceutically acceptable salt or solvate thereof, wherein $R^2$ and $R^4$ are each —Cl, $R^3$ is —Br, and $R^5$ is —F. In some embodiments is a compound of Formula (I), or a pharmaceutically acceptable salt or solvate thereof, wherein $R^2$, $R^3$, $R^4$, and $R^5$ are each —Cl. In some embodiments is a compound of Formula (I), or a pharmaceutically acceptable salt or solvate thereof, wherein $R^2$, $R^4$, and $R^5$ are each —Cl and $R^3$ is —Br. In some embodiments is a compound of Formula (I), or a pharmaceutically acceptable salt or solvate thereof, wherein $R^2$ and $R^3$ are each —Cl, and $R^4$ and $R^5$ are each —F. In some embodiments is a compound of Formula (I), or a pharmaceutically acceptable salt or solvate thereof, wherein $R^2$ is —Cl, $R^3$ is —Br, and $R^4$ and $R^5$ are each —F. In some embodiments is a compound of Formula (I), or a pharmaceutically acceptable salt or solvate thereof, wherein $R^2$ and $R^5$ are each —F, $R^3$ is H, and $R^4$ is —Cl. In some embodiments is a compound of Formula (I), or a pharmaceutically acceptable salt or solvate thereof, wherein $R^2$ and $R^4$ are each —Cl, and $R^3$ and $R^5$ are each —F. In some embodiments is a compound of Formula (I), or a pharmaceutically acceptable salt or solvate thereof, wherein $R^2$ is —F, $R^3$ is H, and $R^4$ and $R^5$ are each —Cl. In some embodiments is a compound of Formula (I), or a pharmaceutically acceptable salt or solvate thereof, wherein $R^2$, $R^4$, and $R^5$ are each —Cl and $R^3$ is —F. In some embodiments is a compound of Formula (I), or a pharmaceutically acceptable salt or solvate thereof, wherein $R^2$ is —Cl, $R^3$ is H, and $R^4$ and $R^5$ are each —F. In some embodiments is a compound of Formula (I), or a pharmaceutically acceptable salt or solvate thereof, wherein $R^2$ is —Cl, and $R^3$, $R^4$, and $R^5$ are each —F. In some embodiments is a compound of Formula (I), or a pharmaceutically acceptable salt or solvate thereof, wherein $R^2$ and $R^3$ are each —Br, $R^4$ is —Cl, and $R^5$ is —F. In some embodiments is a compound of Formula (I), or a pharmaceutically acceptable salt or solvate thereof, wherein $R^2$ and $R^3$ are each —Br, and $R^4$ and $R^5$ are each —Cl. In some embodiments is a compound of Formula (I), or a pharmaceutically acceptable salt or solvate thereof, wherein $R^2$ and $R^3$ are each —Br, and $R^4$ and $R^5$ are each —F.

In some embodiments is a compound of Formula (I), or a pharmaceutically acceptable salt or solvate thereof, wherein $R^6$ is H. In some embodiments is a compound of Formula (I), or a pharmaceutically acceptable salt or solvate thereof, wherein $R^6$ is $C_{1-6}$alkyl. In some embodiments is a compound of Formula (I), or a pharmaceutically acceptable salt or solvate thereof, wherein $R^6$ is —$CH_3$.

In some embodiments is a compound of Formula (I) having the structure of Formula (Ia):

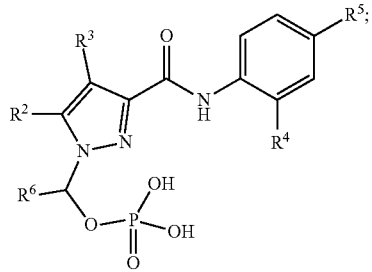

Formula (Ia)

wherein:

$R^2$, $R^3$, $R^4$, and $R^5$ are each independently selected from H, halogen, —CN, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$OR^{10}$, —$SR^{10}$, —$N(R^{10})_2$, —$C(O)OR^{10}$, —$C(O)N(R^{10})_2$, —$OC(O)N(R^{10})_2$, —$N(R^{11})C(O)N(R^{10})_2$, —$N(R^{11})C(O)OR^{10}$, —$N(R^{11})C(O)R^{12}$, —$N(R^{11})S(O)_2R^{12}$, —$C(O)R^{12}$, —$S(O)R^{12}$, —$S(O)_2R^{12}$, —$S(O)_2N(R^{10})_2$, and —$OC(O)R^{12}$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{13}$;

$R^6$ is selected from H, $C_{1-6}$alkyl, and $C_{1-6}$haloalkyl;

each $R^{10}$ is independently selected from H, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl;

each $R^{11}$ is independently selected from H, $C_{1-6}$alkyl, and $C_{1-6}$haloalkyl;

each $R^{12}$ is independently selected from $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{13}$;

each $R^{13}$ is independently selected from halogen, —CN, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$OR^{15}$, —$SR^{15}$, —$N(R^{16})(R^{17})$, —$C(O)OR^{16}$, —$C(O)N(R^{16})(R^{17})$, —$C(O)C(O)N(R^{16})(R^{17})$, —$OC(O)N(R^{16})(R^{17})$, —$N(R^{18})C(O)N(R^{16})(R^{17})$, —$N(R^{18})C(O)OR^{19}$, —$N(R^{18})C(O)R^{19}$, —$N(R^{18})S(O)_2R^{19}$, —$C(O)R^{19}$, —$S(O)_2R^{19}$, —$S(O)_2N(R^{16})(R^{17})$, and —$OC(O)R^{19}$, wherein $C_{1-6}$alkyl, $C_{2-6}$alkenyl, $C_{2-6}$alkynyl, $C_{3-6}$cycloalkyl, —$CH_2$—$C_{3-6}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, and $C_{1-9}$ heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{15}$, —$SR^{15}$, —$N(R^{15})_2$, —$C(O)OR^{15}$, —$C(O)N(R^{15})_2$, —$C(O)C(O)N(R^{15})_2$, —$OC(O)N(R^{15})_2$, —$N(R^{16})C(O)N(R^{15})_2$, —$N(R^{16})C(O)OR^{15}$, —$N(R^{16})C(O)R^{17}$, —$N(R^{16})S(O)_2R^{17}$, —$C(O)R^{17}$, —$S(O)_2R^{17}$, —$S(O)_2N(R^{15})_2$, and —$OC(O)R^{17}$;

each $R^{15}$ is independently selected from H, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl;

each $R^{16}$ is independently selected from H and $C_{1-6}$alkyl;

each $R^{17}$ is selected from $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl;

each $R^{18}$ is independently selected from H and $C_{1-6}$alkyl; and each $R^{19}$ is selected from $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl;

or a pharmaceutically acceptable salt or solvate thereof.

In some embodiments is a compound of Formula (Ia), or a pharmaceutically acceptable salt or solvate thereof, wherein $R^2$, $R^3$, $R^4$, and $R^5$ are each independently selected from H, halogen, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{13}$. In some embodiments is a compound of Formula (Ia), or a pharmaceutically acceptable salt or solvate thereof, wherein $R^2$, $R^3$, $R^4$, and $R^5$ are each independently selected from H, halogen, and $C_{1-6}$ alkyl optionally substituted with one, two, or three $R^{13}$. In some embodiments is a compound of Formula (Ia), or a pharmaceutically acceptable salt or solvate thereof, wherein $R^2$, $R^3$, $R^4$, and $R^5$ are each independently selected from H, halogen, and unsubstituted $C_{1-6}$alkyl. In some embodiments is a compound of Formula (Ia), or a pharmaceutically acceptable salt or solvate thereof, wherein $R^2$, $R^3$, $R^4$, and $R^5$ are each independently selected from H and halogen. In some embodiments is a compound of Formula (Ia), or a pharmaceutically acceptable salt or solvate thereof, wherein $R^2$, $R^3$, $R^4$, and $R^5$ are each independently halogen.

In some embodiments is a compound of Formula (Ia), or a pharmaceutically acceptable salt or solvate thereof, wherein $R^2$, $R^3$, and $R^4$ are each —Cl and $R^5$ is —F. In some embodiments is a compound of Formula (Ia), or a pharmaceutically acceptable salt or solvate thereof, wherein $R^2$, $R^3$, and $R^5$ are each —Cl and $R^4$ is —F. In some embodiments is a compound of Formula (Ia), or a pharmaceutically acceptable salt or solvate thereof, wherein $R^2$ and $R^4$ are each —Cl, $R^3$ is —Br, and $R^5$ is —F. In some embodiments is a compound of Formula (Ia), or a pharmaceutically acceptable salt or solvate thereof, wherein $R^2$, $R^3$, $R^4$, and $R^5$ are each —Cl. In some embodiments is a compound of Formula (Ia), or a pharmaceutically acceptable salt or solvate thereof, wherein $R^2$, $R^4$, and $R^5$ are each —Cl and $R^3$ is —Br. In some embodiments is a compound of Formula (Ia), or a pharmaceutically acceptable salt or solvate thereof, wherein $R^2$ and $R^3$ are each —Cl, and $R^4$ and $R^5$ are each —F. In some embodiments is a compound of Formula (Ia), or a pharmaceutically acceptable salt or solvate thereof, wherein $R^2$ is —Cl, $R^3$ is —Br, and $R^4$ and $R^5$ are each —F. In some embodiments is a compound of Formula (Ia), or a pharmaceutically acceptable salt or solvate thereof, wherein $R^2$ and $R^5$ are each —F, $R^3$ is H, and $R^4$ is —Cl. In some embodiments is a compound of Formula (Ia), or a pharmaceutically acceptable salt or solvate thereof, wherein $R^2$ and $R^4$ are each —Cl, and $R^3$ and $R^5$ are each —F. In some embodiments is a compound of Formula (Ia), or a pharmaceutically acceptable salt or solvate thereof, wherein $R^2$ is —F, $R^3$ is H, and $R^4$ and $R^5$ are each —Cl. In some embodiments is a compound of Formula (Ia), or a pharmaceutically acceptable salt or solvate thereof, wherein $R^2$, $R^4$, and $R^5$ are each —Cl and $R^3$ is —F. In some embodiments is a compound of Formula (Ia), or a pharmaceutically acceptable salt or solvate thereof, wherein $R^2$ is —Cl, $R^3$ is H, and $R^4$ and $R^5$ are each —F. In some embodiments is a compound of Formula (Ia), or a pharmaceutically acceptable salt or solvate thereof, wherein $R^2$ is —Cl, and $R^3$, $R^4$, and $R^5$ are each —F. In some embodiments is a compound of Formula (Ia), or a pharmaceutically acceptable salt or solvate thereof, wherein $R^2$ and $R^3$ are each —Br, $R^4$ is —Cl, and $R^5$ is —F. In some embodiments is a compound of Formula (Ia), or a pharmaceutically acceptable salt or solvate thereof, wherein $R^2$ and $R^3$ are each —Br, and $R^4$ and $R^5$ are each —Cl. In some embodiments is a compound of Formula (Ia), or a pharmaceutically acceptable salt or solvate thereof, wherein $R^2$ and $R^3$ are each —Br, and $R^4$ and $R^5$ are each —F.

In some embodiments is a compound of Formula (Ia), or a pharmaceutically acceptable salt or solvate thereof, wherein $R^6$ is H. In some embodiments is a compound of Formula (Ia), or a pharmaceutically acceptable salt or solvate thereof, wherein $R^6$ is $C_{1-6}$alkyl. In some embodiments is a compound of Formula (Ia), or a pharmaceutically acceptable salt or solvate thereof, wherein $R^6$ is —$CH_3$.

In some embodiments is a compound of Formula (I) having the structure of Formula (Ib):

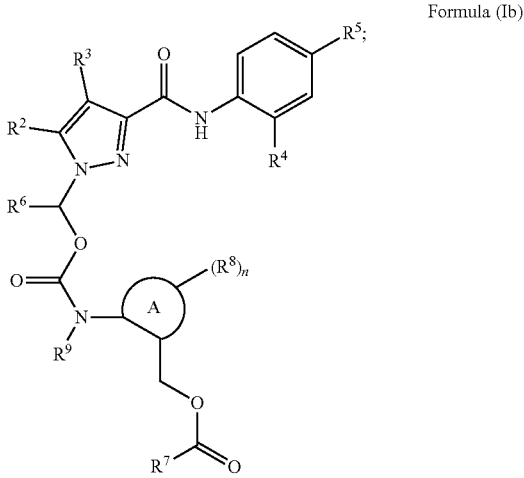

Formula (Ib)

wherein:
Ring A is selected from $C_{3-6}$cycloalkyl, $C_{2-9}$heterocycloalkyl, $C_{6-10}$aryl, and $C_{2-9}$heteroaryl;

$R^2$, $R^3$, $R^4$, and $R^5$ are each independently selected from H, halogen, —CN, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$OR^{10}$, —$SR^{10}$, —$N(R^{10})_2$, —$C(O)OR^{10}$, —$C(O)N(R^{10})_2$, —$OC(O)N(R^{10})_2$, —$N(R^{11})C(O)N(R^{10})_2$, —$N(R^{11})C(O)OR^{10}$, —$N(R^{11})C(O)R^{12}$, —$N(R^{11})S(O)_2R^{12}$, —$C(O)R^{12}$, —$S(O)R^{12}$, —$S(O)_2R^{12}$, —$S(O)_2N(R^{10})_2$, and —$OC(O)R^{12}$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{13}$;

$R^6$ is selected from H, $C_{1-6}$alkyl, and $C_{1-6}$haloalkyl;

$R^7$ is selected from $C_{1-6}$alkyl or —$C_{1-6}$alkyl-$N(R^{14})_2$;

each $R^8$ is independently selected from halogen, —CN, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$OR^{10}$, —$SR^{10}$, —$N(R^{10})_2$, —$C(O)OR^{10}$, —$C(O)N(R^{10})_2$, —$OC(O)N(R^{10})_2$, —$N(R^{11})C(O)N(R^{10})_2$, —$N(R^{11})C(O)OR^{10}$, —$N(R^{11})C(O)R^{12}$, —$N(R^{11})S(O)_2R^{12}$, —$C(O)R^{12}$, —$S(O)R^{12}$, —$S(O)_2R^{12}$, —$S(O)_2N(R^{10})_2$, and —$OC(O)R^{12}$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{13}$;

$R^9$ is selected from H, $C_{1-6}$alkyl, and $C_{1-6}$haloalkyl;

each $R^{10}$ is independently selected from H, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl; each $R^{11}$ is independently selected from H, $C_{1-6}$alkyl, and $C_{1-6}$haloalkyl;

each $R^{12}$ is independently selected from $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{13}$;

each $R^{13}$ is independently selected from halogen, —CN, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$OR^{15}$, —$SR^{15}$, —$N(R^{16})(R^{17})$, —$C(O)OR^{16}$, —$C(O)N(R^{16})(R^{17})$, —$C(O)C(O)N(R^{16})(R^{17})$, —$OC(O)N(R^{16})(R^{17})$, —$N(R^{18})C(O)N(R^{16})(R^{17})$, —$N(R^{18})C(O)OR^{19}$, —$N(R^{18})C(O)R^{19}$, —$N(R^{18})S(O)_2R^{19}$, —$C(O)R^{19}$, —$S(O)_2R^{19}$, —$S(O)_2N(R^{16})(R^{17})$, and —$OC(O)R^{19}$, wherein $C_{1-6}$alkyl, $C_{2-6}$alkenyl, $C_{2-6}$alkynyl, $C_{3-6}$cycloalkyl, —$CH_2$—$C_{3-6}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{15}$, —$SR^{15}$, —$N(R^{15})_2$, —$C(O)OR^{15}$, —$C(O)N(R^{15})_2$, —$C(O)C(O)N(R^{15})_2$, —$OC(O)N(R^{15})_2$, —$N(R^{16})C(O)N(R^{15})_2$, —$N(R^{16})C(O)OR^{15}$, —$N(R^{16})C(O)R^{17}$, —$N(R^{16})S(O)_2R^{17}$, —$C(O)R^{17}$, —$S(O)_2R^{17}$, —$S(O)_2N(R^{15})_2$, and —$OC(O)R^{17}$;

each $R^{14}$ is independently selected from H, $C_{1-6}$alkyl, and $C_{1-6}$haloalkyl;

each $R^{15}$ is independently selected from H, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl; each $R^{16}$ is independently selected from H and $C_{1-6}$alkyl;

each $R^{17}$ is selected from $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl;

each $R^{18}$ is independently selected from H and $C_{1-6}$alkyl;

each $R^{19}$ is selected from $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl; and n is 0, 1, 2, 3, or 4;

or a pharmaceutically acceptable salt or solvate thereof.

In some embodiments is a compound of Formula (Ib), or a pharmaceutically acceptable salt or solvate thereof, wherein $R^7$ is $C_{1-6}$alkyl. In some embodiments is a compound of Formula (Ib), or a pharmaceutically acceptable salt or solvate thereof, wherein $R^7$ is —$C_{1-6}$alkyl-N($R^{14}$)$_2$. In some embodiments is a compound of Formula (Ib), or a pharmaceutically acceptable salt or solvate thereof, wherein $R^7$ is —$C_{1-6}$alkyl-NH$_2$. In some embodiments is a compound of Formula (Ib), or a pharmaceutically acceptable salt or solvate thereof, wherein $R^7$ is —$C_{1-6}$alkyl-N(H)CH$_3$.

In some embodiments is a compound of Formula (Ib), or a pharmaceutically acceptable salt or solvate thereof, wherein $R^9$ is $C_{1-6}$alkyl. In some embodiments is a compound of Formula (Ib), or a pharmaceutically acceptable salt or solvate thereof, wherein $R^9$ is —CH$_3$. In some embodiments is a compound of Formula (Ib), or a pharmaceutically acceptable salt or solvate thereof, wherein $R^9$ is H.

In some embodiments is a compound of Formula (Ib), or a pharmaceutically acceptable salt or solvate thereof, wherein n is 0, 1, or 2. In some embodiments is a compound of Formula (Ib), or a pharmaceutically acceptable salt or solvate thereof, wherein n is 2. In some embodiments is a compound of Formula (Ib), or a pharmaceutically acceptable salt or solvate thereof, wherein n is 1. In some embodiments is a compound of Formula (Ib), or a pharmaceutically acceptable salt or solvate thereof, wherein n is 0.

In some embodiments is a compound of Formula (Ib), or a pharmaceutically acceptable salt or solvate thereof, wherein each $R^8$ is independently selected from halogen and unsubstituted $C_{1-6}$alkyl. In some embodiments is a compound of Formula (Ib), or a pharmaceutically acceptable salt or solvate thereof, wherein n is 1 or 2 and each $R^8$ is independently selected from halogen and unsubstituted $C_{1-6}$alkyl. In some embodiments is a compound of Formula (Ib), or a pharmaceutically acceptable salt or solvate thereof, wherein n is 1 and $R^8$ is halogen. In some embodiments is a compound of Formula (Ib), or a pharmaceutically acceptable salt or solvate thereof, wherein n is 1 and $R^8$ is unsubstituted $C_{1-6}$alkyl.

In some embodiments is a compound of Formula (Ib), or a pharmaceutically acceptable salt or solvate thereof, wherein $R^2$, $R^3$, $R^4$, and $R^5$ are each independently selected from H, halogen, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{13}$. In some embodiments is a compound of Formula (Ib), or a pharmaceutically acceptable salt or solvate thereof, wherein $R^2$, $R^3$, $R^4$, and $R^5$ are each independently selected from H, halogen, and $C_{1-6}$ alkyl optionally substituted with one, two, or three $R^{13}$. In some embodiments is a compound of Formula (Ib), or a pharmaceutically acceptable salt or solvate thereof, wherein $R^2$, $R^3$, $R^4$, and $R^5$ are each independently selected from H, halogen, and unsubstituted $C_{1-6}$alkyl. In some embodiments is a compound of Formula (Ib), or a pharmaceutically acceptable salt or solvate thereof, wherein $R^2$, $R^3$, $R^4$, and $R^5$ are each independently selected from H and halogen. In some embodiments is a compound of Formula (Ib), or a pharmaceutically acceptable salt or solvate thereof, wherein $R^2$, $R^3$, $R^4$, and $R^5$ are each independently halogen.

In some embodiments is a compound of Formula (Ib), or a pharmaceutically acceptable salt or solvate thereof, wherein $R^2$, $R^3$, and $R^4$ are each —Cl and $R^5$ is —F. In some embodiments is a compound of Formula (Ib), or a pharmaceutically acceptable salt or solvate thereof, wherein $R^2$, $R^3$, and $R^5$ are each —Cl and $R^4$ is —F. In some embodiments is a compound of Formula (Ib), or a pharmaceutically acceptable salt or solvate thereof, wherein $R^2$ and $R^4$ are each —Cl, $R^3$ is —Br, and $R^5$ is —F. In some embodiments is a compound of Formula (Ib), or a pharmaceutically acceptable salt or solvate thereof, wherein $R^2$, $R^3$, $R^4$, and $R^5$ are each —Cl. In some embodiments is a compound of Formula (Ib), or a pharmaceutically acceptable salt or solvate thereof, wherein $R^2$, $R^4$, and $R^5$ are each —Cl and $R^3$ is —Br. In some embodiments is a compound of Formula (Ib), or a pharmaceutically acceptable salt or solvate thereof, wherein $R^2$ and $R^3$ are each —Cl, and $R^4$ and $R^5$ are each —F. In some embodiments is a compound of Formula (Ib), or a pharmaceutically acceptable salt or solvate thereof, wherein $R^2$ is —Cl, $R^3$ is —Br, and $R^4$ and $R^5$ are each —F. In some embodiments is a compound of Formula (Ib), or a pharmaceutically acceptable salt or solvate thereof, wherein $R^2$ and $R^5$ are each —F, $R^3$ is H, and $R^4$ is —Cl. In some embodiments is a compound of Formula (Ib), or a pharmaceutically acceptable salt or solvate thereof, wherein $R^2$ and $R^4$ are each —Cl, and $R^3$ and $R^5$ are each —F. In some embodiments is a compound of Formula (Ib), or a pharmaceutically acceptable salt or solvate thereof, wherein $R^2$ is —F, $R^3$ is H, and $R^4$ and $R^5$ are each —Cl. In some embodiments is a compound of Formula (Ib), or a pharmaceutically acceptable salt or solvate thereof, wherein $R^2$, $R^4$, and $R^5$ are each —Cl and $R^3$ is —F. In some embodiments is a compound of Formula (Ib), or a pharmaceutically acceptable salt or solvate thereof, wherein $R^2$ is —Cl, $R^3$ is H, and $R^4$ and $R^5$ are each —F. In some embodiments is a compound of Formula (Ib), or a pharmaceutically acceptable salt or solvate thereof, wherein $R^2$ is —Cl, and $R^3$, $R^4$, and $R^5$ are each —F. In some embodiments is a compound of Formula (Ib), or a pharmaceutically acceptable salt or solvate thereof, wherein $R^2$ and $R^3$ are each —Br, $R^4$ is —Cl, and $R^5$ is —F. In some embodiments is a compound of Formula (Ib), or a pharmaceutically acceptable salt or solvate thereof, wherein $R^2$ and $R^3$ are each —Br, and $R^4$ and $R^5$ are each —Cl. In some embodiments is a compound of Formula (Ib), or a pharmaceutically acceptable salt or solvate thereof, wherein $R^2$ and $R^3$ are each —Br, and $R^4$ and $R^5$ are each —F.

In some embodiments is a compound of Formula (Ib), or a pharmaceutically acceptable salt or solvate thereof, wherein $R^6$ is H. In some embodiments is a compound of Formula (Ib), or a pharmaceutically acceptable salt or solvate thereof, wherein $R^6$ is $C_{1-6}$alkyl. In some embodiments is a compound of Formula (Ib), or a pharmaceutically acceptable salt or solvate thereof, wherein $R^6$ is —$CH_3$.

In some embodiments is a compound of Formula (II): wherein.

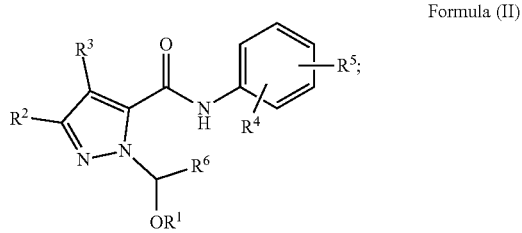

Formula (II)

$R^1$ is —P(O)(OH)$_2$, —C(O)N($R^9$)$C_{2-6}$alkyl-OC(O)$R^7$,

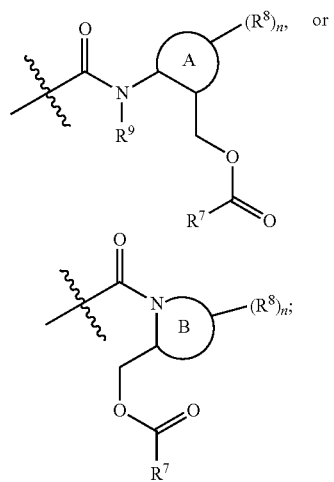

Ring A is selected from $C_{3-6}$cycloalkyl, $C_{2-9}$heterocycloalkyl, $C_{6-10}$aryl, and $C_{2-9}$heteroaryl;

Ring B is selected from $C_{2-9}$heterocycloalkyl and $C_{2-9}$heteroaryl;

$R^2$, $R^3$, $R^4$, and $R^5$ are each independently selected from H, halogen, —CN, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —OR$^{10}$, —SR$^{10}$, —N(R$^{10}$)$_2$, —C(O)OR$^{10}$, —C(O)N(R$^{10}$)$_2$, —OC(O)N(R$^{10}$)$_2$, —N(R$^{11}$)C(O)N(R$^{10}$)$_2$, —N(R$^{11}$)C(O)OR$^{10}$, —N(R$^{11}$)C(O)R$^{12}$, —N(R$^{11}$)S(O)$_2$R$^{12}$, —C(O)R$^{12}$, —S(O)R$^{12}$, —S(O)$_2$R$^{12}$, —S(O)$_2$N(R$^{10}$)$_2$, and —OC(O)R$^{12}$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{13}$;

$R^6$ is selected from H, $C_{1-6}$alkyl, and $C_{1-6}$haloalkyl;

$R^7$ is selected from $C_{1-6}$alkyl or —$C_{1-6}$alkyl-N(R$^{14}$)$_2$;

each $R^8$ is independently selected from halogen, —CN, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —OR$^{10}$, —SR$^{10}$, —N(R$^{10}$)$_2$, —C(O)OR$^{10}$, —C(O)N(R$^{10}$)$_2$, —OC(O)N(R$^{10}$)$_2$, —N(R$^{11}$)C(O)N(R$^{10}$)$_2$, —N(R$^{11}$)C(O)OR$^{10}$, —N(R$^{11}$)C(O)R$^{12}$, —N(R$^{11}$)S(O)$_2$ R$^{12}$, —C(O)R$^{12}$, —S(O)R$^{12}$, —S(O)$_2$R$^{12}$, —S(O)$_2$ N(R$^{10}$)$_2$, and —OC(O)R$^{12}$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{13}$;

$R^9$ is selected from H, $C_{1-6}$alkyl, and $C_{1-6}$haloalkyl;

each $R^{10}$ is independently selected from H, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl;

each $R^{11}$ is independently selected from H, $C_{1-6}$alkyl, and $C_{1-6}$haloalkyl;

each $R^{12}$ is independently selected from $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{13}$;

each $R^{13}$ is independently selected from halogen, —CN, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —OR$^{11}$, —SR$^{15}$, —N(R$^{16}$)(R$^{17}$), —C(O)OR$^{16}$, —C(O)N(R$^{16}$)(R$^{17}$), —C(O)C(O)N(R$^{16}$)(R$^{17}$), —OC(O)N(R$^{16}$)(R$^{17}$), —N(R$^{18}$)C(O)N(R$^{16}$)(R$^{17}$), —N(R$^{18}$)C(O)OR$^{19}$, —N(R$^{18}$)C(O)R$^{19}$, —N(R$^{18}$)S(O)$_2$R$^{19}$, —C(O)R$^{19}$, —S(O)$_2$R$^{19}$, —S(O)$_2$N(R$^{16}$)(R$^{17}$), and —OC(O)R$^{19}$, wherein $C_{1-6}$alkyl, $C_{2-6}$alkenyl, $C_{2-6}$alkynyl, $C_{3-6}$cycloalkyl, —CH$_2$—$C_{3-6}$cycloalkyl, $C_{2-9}$heterocycloalkyl, —CH$_2$—$C_{2-9}$heterocycloalkyl, $C_{6-10}$aryl, —CH$_2$—$C_{6-10}$aryl, and $C_{1-9}$ heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{15}$, —SR$^{15}$, —N(R$^{15}$)$_2$, —C(O)OR$^{15}$, —C(O)N(R$^{15}$)$_2$, —C(O)C(O)N(R$^{15}$)$_2$, —OC(O)N(R$^{15}$)$_2$, —N(R$^{16}$)C(O)N(R$^{15}$)$_2$, —N(R$^{16}$)C(O)OR$^{15}$, —N(R$^{16}$)C(O)R$^{17}$, —N(R$^{16}$)S(O)$_2$R$^{17}$, —C(O)R$^{17}$, —S(O)$_2$R$^{17}$, —S(O)$_2$N(R$^{15}$)$_2$, and —OC(O)R$^{17}$;

each $R^{14}$ is independently selected from H, $C_{1-6}$alkyl, and $C_{1-6}$haloalkyl;

each $R^{15}$ is independently selected from H, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl;

each $R^{16}$ is independently selected from H and $C_{1-6}$alkyl;

each $R^{17}$ is selected from $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl;

each $R^{18}$ is independently selected from H and $C_{1-6}$alkyl;

each $R^{19}$ is selected from $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl; and n is 0, 1, 2, 3, or 4;

or a pharmaceutically acceptable salt or solvate thereof.

In some embodiments is a compound of Formula (II), or a pharmaceutically acceptable salt or solvate thereof, wherein $R^1$ is —P(O)(OH)$_2$.

In some embodiments is a compound of Formula (II), or a pharmaceutically acceptable salt or solvate thereof, wherein $R^1$ is —C(O)N(R$^9$)$C_{2-6}$alkyl-OC(O)R$^7$. In some embodiments is a compound of Formula (II), or a pharmaceutically acceptable salt or solvate thereof, wherein $R^1$ is —C(O)N(H)$C_{2-6}$alkyl-OC(O)R$^7$. In some embodiments is a compound of Formula (II), or a pharmaceutically acceptable salt or solvate thereof, wherein $R^1$ is —C(O)N(H)$C_{2-6}$alkyl-OC(O)R$^7$ and $R^7$ is $C_{1-6}$alkyl. In some embodiments is a compound of Formula (II), or a pharmaceutically acceptable salt or solvate thereof, wherein $R^1$ is —C(O)N(H)$C_{2-6}$alkyl-OC(O)R$^7$ and $R^7$ is —$C_{1-6}$ alkyl-N(R$^{14}$)$_2$. In some embodiments is a compound of Formula (II), or a pharmaceutically acceptable salt or solvate thereof, wherein $R^1$ is —C(O)N(H)$C_{2-6}$alkyl-OC(O)$R^7$ and $R^7$ is —$C_{1-6}$ alkyl-NH$_2$. In some embodiments is a compound of Formula (II), or a pharmaceutically acceptable salt or solvate thereof, wherein $R^1$ is —C(O)N(H)$C_{2-6}$alkyl-OC(O)$R^7$ and $R^7$ is —$C_{1-6}$ alkyl-N(H)CH$_3$. In some embodiments is a compound of Formula (II), or a pharmaceutically acceptable salt or solvate thereof, wherein $R^1$ is —C(O)N(CH$_3$)$C_{2-6}$alkyl-OC(O)$R^7$. In some embodiments is a compound of Formula (II), or a pharmaceutically acceptable salt or solvate thereof, wherein $R^1$ is —C(O)N(CH$_3$)$C_{2-6}$alkyl-OC(O)$R^7$ and $R^7$ is $C_{1-6}$alkyl. In some embodiments is a compound of Formula (II), or a pharmaceutically acceptable salt or solvate thereof, wherein $R^1$ is —C(O)N(CH$_3$)$C_{2-6}$alkyl-OC(O)$R^7$ and $R^7$ is —$C_{1-6}$ alkyl-N($R^{14}$)$_2$. In some embodiments is a compound of Formula (II), or a pharmaceutically acceptable salt or solvate thereof, wherein $R^1$ is —C(O)N(CH$_3$)$C_{2-6}$alkyl-OC(O)$R^7$ and $R^7$ is —$C_{1-6}$alkyl-NH$_2$. In some embodiments is a compound of Formula (II), or a pharmaceutically acceptable salt or solvate thereof, wherein $R^1$ is —C(O)N(CH$_3$)$C_{2-6}$ alkyl-OC(O)$R^7$ and $R^7$ is —$C_{1-6}$alkyl-N(H)CH$_3$.

In some embodiments is a compound of Formula (II), or a pharmaceutically acceptable salt or solvate thereof, wherein $R^1$ is

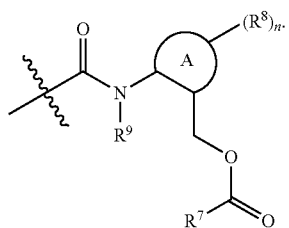

In some embodiments is a compound of Formula (II), or a pharmaceutically acceptable salt or solvate thereof, wherein $R^1$ is

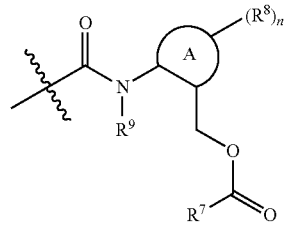

and Ring A is $C_{2-9}$heteroaryl. In some embodiments is a compound of Formula (II), or a pharmaceutically acceptable salt or solvate thereof, wherein $R^1$ is

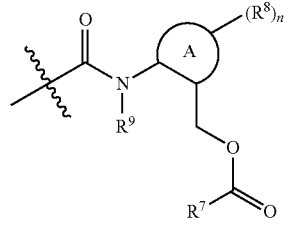

and Ring A is $C_{2-9}$heteroaryl selected from oxazolyl, thiazolyl, pyrazolyl, furanyl, thienyl, pyrrolyl, imidazolyl, isoxazolyl, isothiazolyl, pyridinyl, pyrimidinyl, pyrazinyl, and pyridazinyl. In some embodiments is a compound of Formula (II), or a pharmaceutically acceptable salt or solvate thereof, wherein $R^1$ is

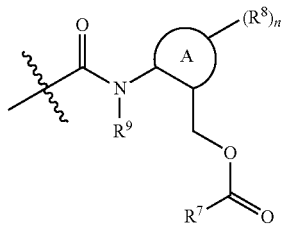

and Ring A is $C_{2-9}$heteroaryl selected from pyridinyl, pyrimidinyl, pyrazinyl, and pyridazinyl. In some embodiments is a compound of Formula (II), or a pharmaceutically acceptable salt or solvate thereof, wherein $R^1$ is

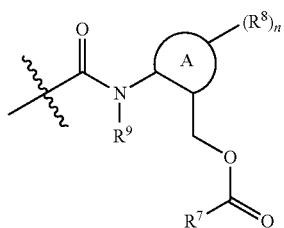

and Ring A is pyridinyl.

In some embodiments is a compound of Formula (II), or a pharmaceutically acceptable salt or solvate thereof, wherein R is

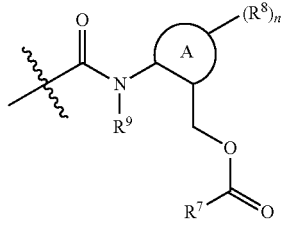

and Ring A is phenyl.

In some embodiments is a compound of Formula (II), or a pharmaceutically acceptable salt or solvate thereof, wherein $R^9$ is $C_{1-6}$alkyl.

In some embodiments is a compound of Formula (II), or a pharmaceutically acceptable salt or solvate thereof, wherein $R^1$ is

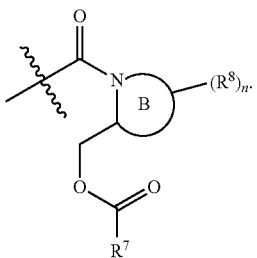

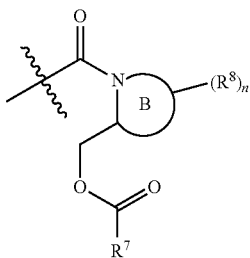

In some embodiments is a compound of Formula (II), or a pharmaceutically acceptable salt or solvate thereof, wherein $R^1$ is

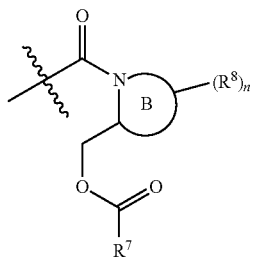

and Ring B is $C_{2-9}$heteroaryl. In some embodiments is a compound of Formula (II), or a pharmaceutically acceptable salt or solvate thereof, wherein $R^1$ is

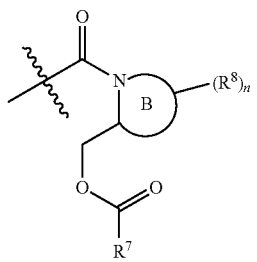

and Ring B is $C_{2-9}$heteroaryl selected from pyrazolyl, pyrrolyl, and imidazolyl.

In some embodiments is a compound of Formula (II), or a pharmaceutically acceptable salt or solvate thereof, wherein $R^1$ is

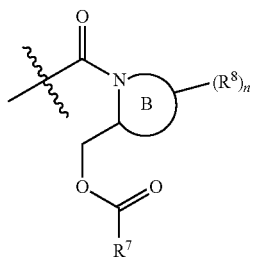

and Ring B is $C_{2-9}$heterocycloalkyl. In some embodiments is a compound of Formula (II), or a pharmaceutically acceptable salt or solvate thereof, wherein $R^1$ is and Ring B is $C_{2-9}$heterocycloalkyl selected from pyrrolidinyl, piperidinyl, morpholinyl, and piperazinyl.

In some embodiments is a compound of Formula (II), or a pharmaceutically acceptable salt or solvate thereof, wherein n is 0, 1, or 2. In some embodiments is a compound of Formula (II), or a pharmaceutically acceptable salt or solvate thereof, wherein n is 2. In some embodiments is a compound of Formula (II), or a pharmaceutically acceptable salt or solvate thereof, wherein n is 1. In some embodiments is a compound of Formula (II), or a pharmaceutically acceptable salt or solvate thereof, wherein n is 0.

In some embodiments is a compound of Formula (II), or a pharmaceutically acceptable salt or solvate thereof, wherein each $R^8$ is independently selected from halogen and unsubstituted $C_{1-6}$alkyl. In some embodiments is a compound of Formula (II), or a pharmaceutically acceptable salt or solvate thereof, wherein n is 1 or 2 and each $R^8$ is independently selected from halogen and unsubstituted $C_{1-6}$alkyl. In some embodiments is a compound of Formula (II), or a pharmaceutically acceptable salt or solvate thereof, wherein n is 1 and $R^8$ is halogen. In some embodiments is a compound of Formula (II), or a pharmaceutically acceptable salt or solvate thereof, wherein n is 1 and $R^8$ is unsubstituted $C_{1-6}$alkyl.

In some embodiments is a compound of Formula (II), or a pharmaceutically acceptable salt or solvate thereof, wherein $R^2$, $R^3$, $R^4$, and $R^5$ are each independently selected from H, halogen, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{13}$. In some embodiments is a compound of Formula (II), or a pharmaceutically acceptable salt or solvate thereof, wherein $R^2$, $R^3$, $R^4$, and $R^5$ are each independently selected from H, halogen, and $C_{1-6}$ alkyl optionally substituted with one, two, or three $R^{13}$. In some embodiments is a compound of Formula (II), or a pharmaceutically acceptable salt or solvate thereof, wherein $R^2$, $R^3$, $R^4$, and $R^5$ are each independently selected from H, halogen, and unsubstituted $C_{1-6}$alkyl. In some embodiments is a compound of Formula (II), or a pharmaceutically acceptable salt or solvate thereof, wherein $R^2$, $R^3$, $R^4$, and $R^5$ are each independently selected from H and halogen. In some embodiments is a compound of Formula (II), or a pharmaceutically acceptable salt or solvate thereof, wherein $R^2$, $R^3$, $R^4$, and $R^5$ are each independently halogen.

In some embodiments is a compound of Formula (II), or a pharmaceutically acceptable salt or solvate thereof, wherein $R^2$, $R^3$, and $R^4$ are each —Cl and $R^5$ is —F. In some embodiments is a compound of Formula (II), or a pharmaceutically acceptable salt or solvate thereof, wherein $R^2$, $R^3$, and $R^5$ are each —Cl and $R^4$ is —F. In some embodiments is a compound of Formula (II), or a pharmaceutically acceptable salt or solvate thereof, wherein $R^2$ and $R^4$ are each —Cl, $R^3$ is —Br, and $R^5$ is —F. In some embodiments is a compound of Formula (II), or a pharmaceutically acceptable salt or solvate thereof, wherein $R^2$, $R^3$, $R^4$, and $R^5$ are each —Cl. In some embodiments is a compound of Formula (II), or a pharmaceutically acceptable salt or solvate thereof, wherein $R^2$, $R^4$, and $R^5$ are each —Cl and $R^3$ is —Br. In some embodiments is a compound of Formula (II), or a pharmaceutically acceptable salt or solvate thereof, wherein $R^2$ and $R^3$ are each —Cl, and $R^4$ and $R^5$ are each —F. In some embodiments is a compound of Formula (II), or a pharmaceutically acceptable salt or solvate thereof, wherein $R^2$ is —Cl, $R^3$ is —Br, and $R^4$ and $R^5$ are each —F. In some embodiments is a compound of Formula (II), or a pharmaceutically acceptable salt or solvate thereof, wherein $R^2$ and $R^5$ are each —F, $R^3$ is H, and $R^4$ is —C$_1$. In some embodiments is a compound of Formula (II), or a pharmaceutically acceptable salt or solvate thereof, wherein $R^2$ and $R^4$ are each —Cl, and $R^3$ and $R^5$ are each —F. In some embodiments is a compound of Formula (II), or a pharmaceutically acceptable salt or solvate thereof, wherein $R^2$ is —F, $R^3$ is H, and $R^4$ and $R^5$ are each —Cl. In some embodiments is a compound of Formula (II), or a pharmaceutically acceptable salt or solvate thereof, wherein $R^2$, $R^4$, and $R^5$ are each —C$_1$ and $R^3$ is —F. In some embodiments is a compound of Formula (II), or a pharmaceutically acceptable salt or solvate thereof, wherein $R^2$ is —Cl, $R^3$ is H, and $R^4$ and $R^5$ are each —F. In some embodiments is a compound of Formula (II), or a pharmaceutically acceptable salt or solvate thereof, wherein $R^2$ is —Cl, and $R^3$, $R^4$, and $R^5$ are each —F. In some embodiments is a compound of Formula (II), or a pharmaceutically acceptable salt or solvate thereof, wherein $R^2$ and $R^3$ are each —Br, $R^4$ is —Cl, and $R^5$ is —F. In some embodiments is a compound of Formula (II), or a pharmaceutically acceptable salt or solvate thereof, wherein $R^2$ and $R^3$ are each —Br, and $R^4$ and $R^5$ are each —Cl. In some embodiments is a compound of Formula (II), or a pharmaceutically acceptable salt or solvate thereof, wherein $R^2$ and $R^3$ are each —Br, and $R^4$ and $R^5$ are each —F.

In some embodiments is a compound of Formula (II), or a pharmaceutically acceptable salt or solvate thereof, wherein $R^6$ is H. In some embodiments is a compound of Formula (II), or a pharmaceutically acceptable salt or solvate thereof, wherein $R^6$ is $C_{1-6}$alkyl. In some embodiments is a compound of Formula (II), or a pharmaceutically acceptable salt or solvate thereof, wherein $R^6$ is —CH$_3$.

In some embodiments is a compound of Formula (II) having the structure of Formula (IIa):
wherein:

Formula (IIa)

$R^2$, $R^3$, $R^4$, and $R^5$ are each independently selected from H, halogen, —CN, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —OR$^{10}$, —SR$^{10}$, —N(R$^{10}$)$_2$, —C(O)OR$^{10}$, —C(O)N(R$^{10}$)$_2$, —OC(O)N(R$^{10}$)$_2$, —N(R$^{11}$)C(O)N(R$^{10}$)$_2$, —N(R$^{11}$)C(O)OR$^{10}$, —N(R$^{11}$)C(O)R$^{12}$, —N(R$^{11}$)S(O)$_2$R$^{12}$, —C(O)R$^{12}$, —S(O)R$^{12}$, —S(O)$_2$R$^{12}$, —S(O)$_2$N(R$^{10}$)$_2$, and —OC(O)R$^{12}$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three R$^{13}$;

$R^6$ is selected from H, $C_{1-6}$alkyl, and $C_{1-6}$haloalkyl;

each R$^{10}$ is independently selected from H, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl;

each R$^{11}$ is independently selected from H, $C_{1-6}$alkyl, and $C_{1-6}$haloalkyl;

each R$^{12}$ is independently selected from $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three R$^{13}$;

each R$^{13}$ is independently selected from halogen, —CN, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —OR$^{15}$, —SR$^{15}$, —N(R$^{16}$)(R$^{17}$), —C(O)OR$^{16}$, —C(O)N(R$^{16}$)(R$^{17}$), —C(O)C(O)N(R$^{16}$)(R$^{17}$), —OC(O)N(R$^{16}$)(R$^{17}$), —N(R$^{18}$)C(O)N(R$^{16}$)(R$^{17}$), —N(R$^{18}$)C(O)OR$^{19}$, —N(R$^{18}$)C(O)R$^{19}$, —N(R$^{18}$)S(O)$_2$R$^{19}$, —C(O)R$^{19}$, —S(O)$_2$R$^{19}$, —S(O)$_2$N(R$^{16}$)(R$^{17}$), and —OC(O)R$^{19}$, wherein $C_{1-6}$alkyl, $C_{2-6}$alkenyl, $C_{2-6}$alkynyl, $C_{3-6}$cycloalkyl, —CH$_2$—$C_{3-6}$cycloalkyl, $C_{2-9}$heterocycloalkyl, —CH$_2$—$C_{2-9}$heterocycloalkyl, $C_{6-10}$aryl, —CH$_2$—$C_{6-10}$aryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{15}$, —SR$^{15}$, —N(R$^{15}$)$_2$, —C(O)OR$^{15}$, —C(O)N(R$^{15}$)$_2$, —C(O)C(O)N(R$^{15}$)$_2$, —OC(O)N(R$^{15}$)$_2$, —N(R$^{16}$)C(O)N(R$^{15}$)$_2$, —N(R$^{16}$)C(O)OR$^{15}$, —N(R$^{16}$)C(O)R$^{17}$, —N(R$^{16}$)S(O)$_2$R$^{17}$, —C(O)R$^{17}$, —S(O)$_2$R$^{17}$, —S(O)$_2$N(R$^{15}$)$_2$, and —OC(O)R$^{17}$;

each R$^{15}$ is independently selected from H, $C_{1-6}$alkyl, $C_6$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl;

each R$^{16}$ is independently selected from H and $C_{1-6}$alkyl;

each R$^{17}$ is selected from $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl;

each R$^{11}$ is independently selected from H and $C_{1-6}$alkyl; and each R$^{19}$ is selected from $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl;

or a pharmaceutically acceptable salt or solvate thereof.

In some embodiments is a compound of Formula (IIa), or a pharmaceutically acceptable salt or solvate thereof, wherein $R^2$, $R^3$, $R^4$, and $R^5$ are each independently selected from H, halogen, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three R$^{13}$. In some embodiments is a compound of Formula (IIa), or a pharmaceutically acceptable salt or solvate thereof, wherein $R^2$, $R^3$, $R^4$, and $R^5$ are each independently selected from H, halogen, and $C_{1-6}$alkyl optionally substituted with one, two, or three $R^{13}$. In some embodiments is a compound of Formula (IIa), or a pharmaceutically acceptable salt or solvate thereof, wherein $R^2$, $R^3$, $R^4$, and $R^5$ are each independently selected from H, halogen, and unsubstituted $C_{1-6}$alkyl. In some embodiments is a compound of Formula (IIa), or a pharmaceutically acceptable salt or solvate thereof, wherein $R^2$, $R^3$, $R^4$, and $R^5$ are each independently selected from H and halogen. In some embodiments is a compound of Formula (IIa), or a pharmaceutically acceptable salt or solvate thereof, wherein $R^2$, $R^3$, $R^4$, and $R^5$ are each independently halogen.

In some embodiments is a compound of Formula (IIa), or a pharmaceutically acceptable salt or solvate thereof, wherein $R^2$, $R^3$, and $R^4$ are each —Cl and $R^5$ is —F. In some embodiments is a compound of Formula (IIa), or a pharmaceutically acceptable salt or solvate thereof, wherein $R^2$, $R^3$, and $R^5$ are each —Cl and $R^4$ is —F. In some embodiments is a compound of Formula (IIa), or a pharmaceutically acceptable salt or solvate thereof, wherein $R^2$ and $R^4$ are each —Cl, $R^3$ is —Br, and $R^5$ is —F. In some embodiments is a compound of Formula (IIa), or a pharmaceutically acceptable salt or solvate thereof, wherein $R^2$, $R^3$, $R^4$, and $R^5$ are each —Cl. In some embodiments is a compound of Formula (IIa), or a pharmaceutically acceptable salt or solvate thereof, wherein $R^2$, $R^4$, and $R^5$ are each —Cl and $R^3$ is —Br. In some embodiments is a compound of Formula (IIa), or a pharmaceutically acceptable salt or solvate thereof, wherein $R^2$ and $R^3$ are each —Cl, and $R^4$ and $R^5$ are each —F. In some embodiments is a compound of Formula (IIa), or a pharmaceutically acceptable salt or solvate thereof, wherein $R^2$ is —Cl, $R^3$ is —Br, and $R^4$ and $R^5$ are each —F. In some embodiments is a compound of Formula (IIa), or a pharmaceutically acceptable salt or solvate thereof, wherein $R^2$ and $R^5$ are each —F, $R^3$ is H, and $R^4$ is —Cl. In some embodiments is a compound of Formula (IIa), or a pharmaceutically acceptable salt or solvate thereof, wherein $R^2$ and $R^4$ are each —Cl, and $R^3$ and $R^5$ are each —F. In some embodiments is a compound of Formula (IIa), or a pharmaceutically acceptable salt or solvate thereof, wherein $R^2$ is —F, $R^3$ is H, and $R^4$ and $R^5$ are each —Cl. In some embodiments is a compound of Formula (IIa), or a pharmaceutically acceptable salt or solvate thereof, wherein $R^2$, $R^4$, and $R^5$ are each —Cl and $R^3$ is —F. In some embodiments is a compound of Formula (IIa), or a pharmaceutically acceptable salt or solvate thereof, wherein $R^2$ is —Cl, $R^3$ is H, and $R^4$ and $R^5$ are each —F. In some embodiments is a compound of Formula (IIa), or a pharmaceutically acceptable salt or solvate thereof, wherein $R^2$ is —Cl, and $R^3$, $R^4$, and $R^5$ are each —F. In some embodiments is a compound of Formula (IIa), or a pharmaceutically acceptable salt or solvate thereof, wherein $R^2$ and $R^3$ are each —Br, $R^4$ is —Cl, and $R^5$ is —F. In some embodiments is a compound of Formula (IIa), or a pharmaceutically acceptable salt or solvate thereof, wherein $R^2$ and $R^3$ are each —Br, and $R^4$ and $R^5$ are each —Cl. In some embodiments is a compound of Formula (IIa), or a pharmaceutically acceptable salt or solvate thereof, wherein $R^2$ and $R^3$ are each —Br, and $R^4$ and $R^5$ are each —F.

In some embodiments is a compound of Formula (IIa), or a pharmaceutically acceptable salt or solvate thereof, wherein $R^6$ is H. In some embodiments is a compound of Formula (IIa), or a pharmaceutically acceptable salt or solvate thereof, wherein $R^6$ is $C_{1-6}$alkyl. In some embodiments is a compound of Formula (IIa), or a pharmaceutically acceptable salt or solvate thereof, wherein $R^6$ is —CH$_3$.

In some embodiments is a compound of Formula (II) having the structure of Formula (IIb):

wherein:

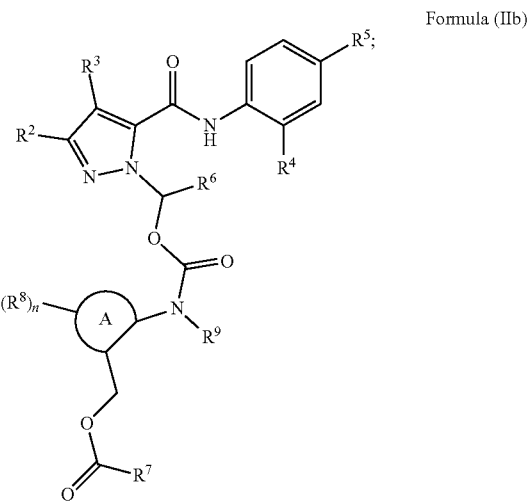

Formula (IIb)

Ring A is selected from $C_{3-6}$cycloalkyl, $C_{2-9}$heterocycloalkyl, $C_{6-10}$aryl, and $C_{2-9}$heteroaryl;

$R^2$, $R^3$, $R^4$, and $R^5$ are each independently selected from H, halogen, —CN, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —OR$^{10}$, —SR$^{10}$, —N(R$^{10}$)$_2$, —C(O)OR$^{10}$, —C(O)N(R$^{10}$)$_2$, —OC(O)N(R$^{10}$)$_2$, —N(R$^{11}$)C(O)N(R$^{10}$)$_2$, —N(R$^{11}$)C(O)OR$^{10}$, —N(R$^{11}$)C(O)R$^{12}$, —N(R$^{11}$)S(O)$_2$R$^{12}$, —C(O)R$^{12}$, —S(O)R$^{12}$, —S(O)$_2$R$^{12}$, —S(O)$_2$N(R$^1$)$_2$, and —OC(O)R$^{12}$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{13}$;

$R^6$ is selected from H, $C_{1-6}$alkyl, and $C_{1-6}$haloalkyl;

$R^7$ is selected from $C_{1-6}$alkyl or —$C_{1-6}$alkyl-N(R$^{14}$)$_2$;

each $R^8$ is independently selected from halogen, —CN, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —OR$^{10}$, —SR$^{10}$, —N(R$^{10}$)$_2$, —C(O)OR$^{10}$, —C(O)N (R$^{10}$)$_2$, —OC(O)N(R$^{10}$)$_2$, —N(R$^{11}$)C(O)N(R$^{10}$)$_2$, —N(R$^{11}$)C(O)OR$^{10}$, —N(R$^{11}$)C(O)R$^{12}$, —N(R$^{11}$)S(O)$_2$ R$^{12}$, —C(O)R$^{12}$, —S(O)R$^{12}$, —S(O)$_2$R$^{12}$, —S(O)$_2$ N(R$^{10}$)$_2$, and —OC(O)R$^{12}$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{13}$;

$R^9$ is selected from H, $C_{1-6}$alkyl, and $C_6$haloalkyl;

each $R^{10}$ is independently selected from H, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl;

each $R^{11}$ is independently selected from H, $C_{1-6}$alkyl, and $C_{1-6}$haloalkyl;

each $R^{12}$ is independently selected from $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{13}$;

each $R^{13}$ is independently selected from halogen, —CN, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —OR$^{15}$, —SR$^{15}$, —N(R$^{16}$)(R$^{17}$), —C(O)OR$^{16}$, —C(O)N($R^{16}$)($R^{17}$), —C(O)C(O)N($R^{16}$)($R^{17}$), —OC(O)N($R^{16}$)($R^{17}$), —N($R^{18}$)C(O)N($R^{16}$)($R^{17}$), —N($R^{18}$)C(O)O$R^{19}$, —N($R^{18}$)C(O)$R^{19}$, —N($R^{18}$)S(O)$_2R^{19}$, —C(O)$R^{19}$, —S(O)$_2R^{19}$, —S(O)$_2$N($R^{16}$)($R^{17}$), and —OC(O)$R^{19}$, wherein $C_{1-6}$alkyl, $C_{2-6}$alkenyl, $C_{2-6}$alkynyl, $C_{3-6}$cycloalkyl, —CH$_2$—$C_{3-6}$cycloalkyl, $C_{2-9}$heterocycloalkyl, —CH$_2$—$C_{2-9}$heterocycloalkyl, $C_{6-10}$aryl, —CH$_2$—$C_{6-10}$aryl, and $C_{1-9}$ heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —O$R^{15}$, —S$R^{15}$, —N($R^{15}$)$_2$, —C(O)O$R^{15}$, —C(O)N($R^{15}$)$_2$, —C(O)C(O)N($R^{15}$)$_2$, —OC(O)N($R^{15}$)$_2$, —N($R^{16}$)C(O)N($R^{15}$)$_2$, —N($R^{16}$)C(O)O$R^{15}$, —N($R^{16}$)C(O)$R^{17}$, —N($R^{16}$)S(O)$_2R^{17}$, —C(O)$R^{17}$, —S(O)$_2R^{17}$, —S(O)$_2$N($R^{15}$)$_2$, and —OC(O)$R^{17}$;

each $R^{14}$ is independently selected from H, $C_{1-6}$alkyl, and $C_{1-6}$haloalkyl;

each $R^{15}$ is independently selected from H, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl;

each $R^{16}$ is independently selected from H and $C_{1-6}$alkyl;

each $R^{17}$ is selected from $C_{1-6}$alkyl, $C_{2-6}$alkenyl, $C_{2-6}$alkynyl, $C_{3-6}$cycloalkyl, $C_{2-9}$heterocycloalkyl, $C_{1-10}$ aryl, and $C_{1-9}$heteroaryl;

each $R^{11}$ is independently selected from H and $C_{1-6}$alkyl;

each $R^{19}$ is selected from $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl; and n is 0, 1, 2, 3, or 4;
or a pharmaceutically acceptable salt or solvate thereof.

In some embodiments is a compound of Formula (IIb), or a pharmaceutically acceptable salt or solvate thereof, wherein $R^7$ is $C_{1-6}$alkyl. In some embodiments is a compound of Formula (IIb), or a pharmaceutically acceptable salt or solvate thereof, wherein $R^7$ is —$C_{1-6}$ alkyl-N($R^{14}$)$_2$. In some embodiments is a compound of Formula (IIb), or a pharmaceutically acceptable salt or solvate thereof, wherein $R^7$ is —$C_{1-6}$alkyl-NH$_2$. In some embodiments is a compound of Formula (IIb), or a pharmaceutically acceptable salt or solvate thereof, wherein $R^7$ is —$C_{1-6}$alkyl-N(H)CH$_3$.

In some embodiments is a compound of Formula (IIb), or a pharmaceutically acceptable salt or solvate thereof, wherein $R^9$ is $C_{1-6}$alkyl. In some embodiments is a compound of Formula (IIb), or a pharmaceutically acceptable salt or solvate thereof, wherein $R^9$ is —CH$_3$. In some embodiments is a compound of Formula (IIb), or a pharmaceutically acceptable salt or solvate thereof, wherein $R^9$ is H.

In some embodiments is a compound of Formula (IIb), or a pharmaceutically acceptable salt or solvate thereof, wherein n is 0, 1, or 2. In some embodiments is a compound of Formula (IIb), or a pharmaceutically acceptable salt or solvate thereof, wherein n is 2. In some embodiments is a compound of Formula (IIb), or a pharmaceutically acceptable salt or solvate thereof, wherein n is 1. In some embodiments is a compound of Formula (IIb), or a pharmaceutically acceptable salt or solvate thereof, wherein n is 0.

In some embodiments is a compound of Formula (IIb), or a pharmaceutically acceptable salt or solvate thereof, wherein each $R^8$ is independently selected from halogen and unsubstituted $C_{1-6}$alkyl. In some embodiments is a compound of Formula (Ib), or a pharmaceutically acceptable salt or solvate thereof, wherein n is 1 or 2 and each $R^8$ is independently selected from halogen and unsubstituted $C_{1-6}$alkyl. In some embodiments is a compound of Formula (IIb), or a pharmaceutically acceptable salt or solvate thereof, wherein n is 1 and $R^8$ is halogen. In some embodiments is a compound of Formula (IIb), or a pharmaceutically acceptable salt or solvate thereof, wherein n is 1 and $R^8$ is unsubstituted $C_{1-6}$alkyl.

In some embodiments is a compound of Formula (IIb), or a pharmaceutically acceptable salt or solvate thereof, wherein $R^2$, $R^3$, $R^4$, and $R^5$ are each independently selected from H, halogen, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{13}$. In some embodiments is a compound of Formula (IIb), or a pharmaceutically acceptable salt or solvate thereof, wherein $R^2$, $R^3$, $R^4$, and $R^5$ are each independently selected from H, halogen, and $C_{1-6}$alkyl optionally substituted with one, two, or three $R^{13}$. In some embodiments is a compound of Formula (IIb), or a pharmaceutically acceptable salt or solvate thereof, wherein $R^2$, $R^3$, $R^4$, and $R^5$ are each independently selected from H, halogen, and unsubstituted $C_{1-6}$alkyl. In some embodiments is a compound of Formula (IIb), or a pharmaceutically acceptable salt or solvate thereof, wherein $R^2$, $R^3$, $R^4$, and $R^5$ are each independently selected from H and halogen. In some embodiments is a compound of Formula (IIb), or a pharmaceutically acceptable salt or solvate thereof, wherein $R^2$, $R^3$, $R^4$, and $R^5$ are each independently halogen.

In some embodiments is a compound of Formula (IIb), or a pharmaceutically acceptable salt or solvate thereof, wherein $R^2$, $R^3$, and $R^4$ are each —Cl and $R^5$ is —F. In some embodiments is a compound of Formula (IIb), or a pharmaceutically acceptable salt or solvate thereof, wherein $R^2$, $R^3$, and $R^5$ are each —Cl and $R^4$ is —F. In some embodiments is a compound of Formula (IIb), or a pharmaceutically acceptable salt or solvate thereof, wherein $R^2$ and $R^4$ are each —Cl, $R^3$ is —Br, and $R^5$ is —F. In some embodiments is a compound of Formula (Ib), or a pharmaceutically acceptable salt or solvate thereof, wherein $R^2$, $R^3$, $R^4$, and $R^5$ are each —Cl. In some embodiments is a compound of Formula (IIb), or a pharmaceutically acceptable salt or solvate thereof, wherein $R^2$, $R^4$, and $R^5$ are each —Cl and $R^3$ is —Br. In some embodiments is a compound of Formula (IIb), or a pharmaceutically acceptable salt or solvate thereof, wherein $R^2$ and $R^3$ are each —Cl, and $R^4$ and $R^5$ are each —F. In some embodiments is a compound of Formula (IIb), or a pharmaceutically acceptable salt or solvate thereof, wherein $R^2$ is —Cl, $R^3$ is —Br, and $R^4$ and $R^5$ are each —F. In some embodiments is a compound of Formula (IIb), or a pharmaceutically acceptable salt or solvate thereof, wherein $R^2$ and $R^5$ are each —F, $R^3$ is H, and $R^4$ is —$C_1$. In some embodiments is a compound of Formula (IIb), or a pharmaceutically acceptable salt or solvate thereof, wherein $R^2$ and $R^4$ each —Cl, and $R^3$ and $R^5$ are each —F. In some embodiments is a compound of Formula (IIb), or a pharmaceutically acceptable salt or solvate thereof, wherein $R^2$ is —F, $R^3$ is H, and $R^4$ and $R^5$ are each —Cl. In some embodiments is a compound of Formula (IIb), or a pharmaceutically acceptable salt or solvate thereof, wherein $R^2$, $R^4$, and $R^5$ are each —Cl and $R^3$ is —F. In some embodiments is a compound of Formula (IIb), or a pharmaceutically acceptable salt or solvate thereof, wherein $R^2$ is —Cl, $R^3$ is H, and $R^4$ and $R^5$ are each —F. In some embodiments is a compound of Formula (Ib), or a pharmaceutically acceptable salt or solvate thereof, wherein $R^2$ is —Cl, and $R^3$, $R^4$, and $R^5$ are each —F. In some embodiments is a compound of Formula (IIb), or a pharmaceutically acceptable salt or solvate thereof, wherein $R^2$ and $R^3$ are each —Br, $R^4$ is —Cl, and $R^5$ is —F. In some embodiments is a compound of Formula (IIb), or a pharmaceutically acceptable salt or solvate thereof, wherein $R^2$ and $R^3$ are each —Br, and $R^4$ and $R^5$ are each —Cl. In some embodiments is a compound of Formula (IIb), or a pharmaceutically acceptable salt or solvate thereof, wherein $R^2$ and $R^3$ are each —Br, and $R^4$ and $R^5$ are each —F.

In some embodiments is a compound of Formula (IIb), or a pharmaceutically acceptable salt or solvate thereof, wherein $R^6$ is H. In some embodiments is a compound of Formula (IIb), or a pharmaceutically acceptable salt or solvate thereof, wherein $R^6$ is $C_{1-6}$alkyl. In some embodiments is a compound of Formula (IIb), or a pharmaceutically acceptable salt or solvate thereof, wherein $R^6$ is —$CH_3$.

In some embodiments is a compound of Formula (III): wherein:

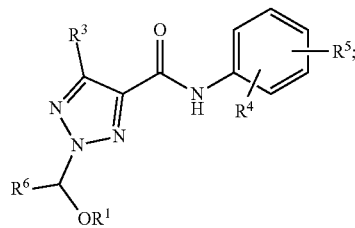

Formula (III)

$R^1$ is —P(O)(OH)$_2$, —C(O)N($R^9$)$C_2$alkyl-OC(O)$R^7$,

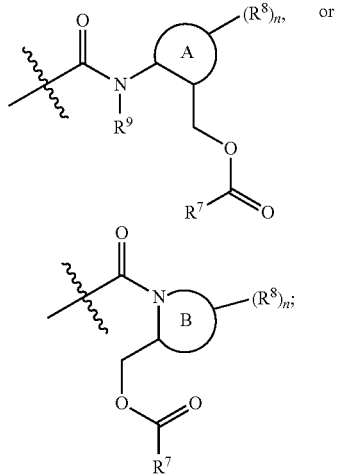

Ring A is selected from $C_{3-6}$cycloalkyl, $C_{2-9}$heterocycloalkyl, $C_{6-10}$aryl, and $C_{2-9}$heteroaryl;
Ring B is selected from $C_{2-9}$heterocycloalkyl and $C_{2-9}$heteroaryl;
$R^3$, $R^4$, and $R^5$ are each independently selected from H, halogen, —CN, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —OR$^{10}$, —SR$^{10}$, —N(R$^{10}$)$_2$, —C(O)OR$^{10}$, —C(O)N(R$^{10}$)$_2$, —OC(O)N(R$^{10}$)$_2$, —N(R$^{11}$)C(O)N(R$^{10}$)$_2$, —N(R$^{11}$)C(O)OR$^{10}$, —N(R$^{11}$)C(O)R$^{12}$, —N(R$^{11}$)S(O)$_2$R$^{12}$, —C(O)R$^{12}$, —S(O)R$^{12}$, —S(O)$_2$R$^{12}$, —S(O)$_2$N(R$^{11}$)$_2$, and —OC(O)R$^{12}$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{13}$;
$R^6$ is selected from H, $C_{1-6}$alkyl, and $C_{1-6}$haloalkyl;
$R^7$ is selected from $C_{1-6}$alkyl or —$C_{1-6}$alkyl-N(R$^{14}$)$_2$;
each $R^8$ is independently selected from halogen, —CN, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —OR$^{10}$, —SR$^{10}$, —N(R$^{10}$)$_2$, —C(O)OR$^{10}$, —C(O)N(R$^{10}$)$_2$, —OC(O)N(R$^{10}$)$_2$, —N(R$^{11}$)C(O)N(R$^{10}$)$_2$, —N(R$^{11}$)C(O)OR$^{10}$, —N(R$^{11}$)C(O)R$^{12}$, —N(R$^{11}$)S(O)$_2$ R$^{12}$, —C(O)R$^{12}$, —S(O)R$^{12}$, —S(O)$_2$R$^{12}$, —S(O)$_2$ N(R$^{10}$)$_2$, and —OC(O)R$^{12}$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{13}$;
$R^9$ is selected from H, $C_{1-6}$alkyl, and $C_{1-6}$haloalkyl;
each $R^{10}$ is independently selected from H, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl; each $R^{11}$ is independently selected from H, $C_{1-6}$alkyl, and $C_{1-6}$haloalkyl;
each $R^{12}$ is independently selected from $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{13}$;
each $R^{13}$ is independently selected from halogen, —CN, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —OR$^{15}$, —SR$^{15}$, —N(R$^{16}$)(R$^{17}$), —C(O)OR$^{16}$, —C(O)N(R$^{16}$)(R$^{17}$), —C(O)C(O)N(R$^{16}$)(R$^{17}$), —OC(O)N(R$^{16}$)(R$^{17}$), —N(R$^{18}$)C(O)N(R$^{16}$)(R$^{17}$), —N(R$^{18}$)C(O)OR$^{19}$, —N(R$^{18}$)C(O)R$^{19}$, —N(R$^{18}$)S(O)$_2$R$^{19}$, —C(O)R$^{19}$, —S(O)$_2$R$^{19}$, —S(O)$_2$N(R$^{16}$)(R$^{17}$), and —OC(O)R$^{19}$, wherein $C_{1-6}$alkyl, $C_{2-6}$alkenyl, $C_{2-6}$alkynyl, $C_{3-6}$cycloalkyl, —$CH_2$—$C_{3-6}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, and $C_{1-9}$ heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{15}$, —SR$^{15}$, —N(R$^{15}$)$_2$, —C(O)OR$^{15}$, —C(O)N(R$^{15}$)$_2$, —C(O)C(O)N(R$^{15}$)$_2$, —OC(O)N(R$^{15}$)$_2$, —N(R$^{16}$)C(O)N(R$^{15}$)$_2$, —N(R$^{16}$)C(O)OR$^{15}$, —N(R$^{16}$)C(O)R$^{17}$, —N(R$^{16}$)S(O)$_2$R$^{17}$, —C(O)R$^{17}$, —S(O)$_2$R$^{17}$, —S(O)$_2$N(R$^{15}$)$_2$, and —OC(O)R$^{17}$;
each $R^{14}$ is independently selected from H, $C_{1-6}$alkyl, and $C_{1-6}$haloalkyl;
each $R^{15}$ is independently selected from H, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl;
each $R^{16}$ is independently selected from H and $C_{1-6}$alkyl;
each $R^{17}$ is selected from $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl;
each $R^{18}$ is independently selected from H and $C_{1-6}$alkyl;
each $R^{19}$ is selected from $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl; and
n is 0, 1, 2, 3, or 4;
or a pharmaceutically acceptable salt or solvate thereof.
In some embodiments is a compound of Formula (III), or a pharmaceutically acceptable salt or solvate thereof, wherein $R^1$ is —P(O)(OH)$_2$.

In some embodiments is a compound of Formula (III), or a pharmaceutically acceptable salt or solvate thereof, wherein $R^1$ is —C(O)N(R$^9$)$C_{2-6}$alkyl-OC(O)$R^7$. In some embodiments is a compound of Formula (III), or a pharmaceutically acceptable salt or solvate thereof, wherein $R^1$ is —C(O)N(H)C$_{2-6}$alkyl-OC(O)R$^7$. In some embodiments is a compound of Formula (III), or a pharmaceutically acceptable salt or solvate thereof, wherein $R^1$ is —C(O)N(H)C$_{2-6}$alkyl-OC(O)R$^7$ and $R^7$ is C$_{1-6}$alkyl. In some embodiments is a compound of Formula (III), or a pharmaceutically acceptable salt or solvate thereof, wherein $R^1$ is —C(O)N(H)C$_{2-6}$alkyl-OC(O)R$^7$ and $R^7$ is —C$_{1-6}$alkyl-N(R$^{14}$)$_2$. In some embodiments is a compound of Formula (III), or a pharmaceutically acceptable salt or solvate thereof, wherein $R^1$ is —C(O)N(H)C$_{2-6}$alkyl-OC(O)R$^7$ and $R^7$ is —C$_{1-6}$alkyl-NH$_2$. In some embodiments is a compound of Formula (III), or a pharmaceutically acceptable salt or solvate thereof, wherein $R^1$ is —C(O)N(H)C$_{2-6}$alkyl-OC(O)R$^7$ and $R^7$ is —C$_{1-6}$alkyl-N(H)CH$_3$. In some embodiments is a compound of Formula (III), or a pharmaceutically acceptable salt or solvate thereof, wherein $R^1$ is —C(O)N(CH$_3$)C$_{2-6}$alkyl-OC(O)R$^7$. In some embodiments is a compound of Formula (III), or a pharmaceutically acceptable salt or solvate thereof, wherein $R^1$ is —C(O)N(CH$_3$)C$_{2-6}$alkyl-OC(O)R$^7$ and $R^7$ is C$_{1-6}$alkyl. In some embodiments is a compound of Formula (III), or a pharmaceutically acceptable salt or solvate thereof, wherein $R^1$ is —C(O)N(CH$_3$)C$_{2-6}$alkyl-OC(O)R$^7$ and $R^7$ is —C$_{1-6}$alkyl-N(R$^{14}$)$_2$. In some embodiments is a compound of Formula (III), or a pharmaceutically acceptable salt or solvate thereof, wherein $R^1$ is —C(O)N(CH$_3$)C$_{2-6}$alkyl-OC(O)R$^7$ and $R^7$ is —C$_{1-6}$alkyl-NH$_2$. In some embodiments is a compound of Formula (III), or a pharmaceutically acceptable salt or solvate thereof, wherein $R^1$ is —C(O)N(CH$_3$)C$_{2-6}$alkyl-OC(O)R$^7$ and $R^7$ is —C$_{1-6}$alkyl-N(H)CH$_3$.

In some embodiments is a compound of Formula (III), or a pharmaceutically acceptable salt or solvate thereof, wherein $R^1$ is

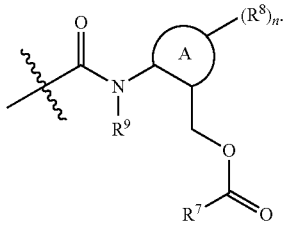

In some embodiments is a compound of Formula (III), or a pharmaceutically acceptable salt or solvate thereof, wherein $R^1$ is

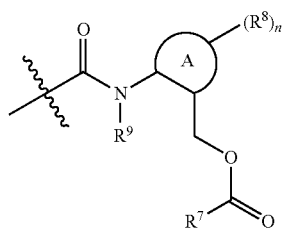

and Ring A is C$_{2-9}$heteroaryl. In some embodiments is a compound of Formula (III), or a pharmaceutically acceptable salt or solvate thereof, wherein $R^1$ is

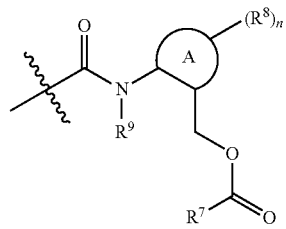

and Ring A is C$_{2-9}$heteroaryl selected from oxazolyl, thiazolyl, pyrazolyl, furanyl, thienyl, pyrrolyl, imidazolyl, isoxazolyl, isothiazolyl, pyridinyl, pyrimidinyl, pyrazinyl, and pyridazinyl. In some embodiments is a compound of Formula (III), or a pharmaceutically acceptable salt or solvate thereof, wherein $R^1$ is

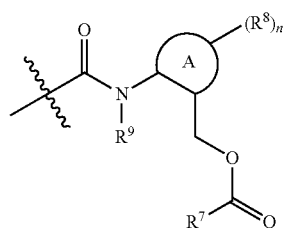

and Ring A is C$_{2-9}$heteroaryl selected from pyridinyl, pyrimidinyl, pyrazinyl, and pyridazinyl. In some embodiments is a compound of Formula (III), or a pharmaceutically acceptable salt or solvate thereof, wherein $R^1$ is

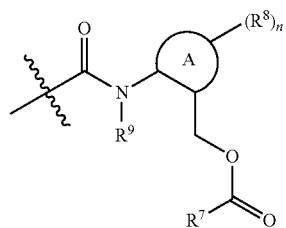

and Ring A is pyridinyl.

In some embodiments is a compound of Formula (III), or a pharmaceutically acceptable salt or solvate thereof, wherein $R^1$ is

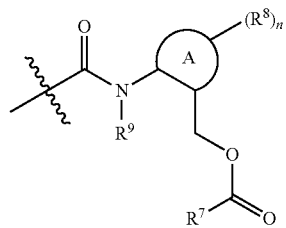

and Ring A is phenyl.

In some embodiments is a compound of Formula (III), or a pharmaceutically acceptable salt or solvate thereof, wherein $R^9$ is C$_{1-6}$alkyl.

In some embodiments is a compound of Formula (III), or a pharmaceutically acceptable salt or solvate thereof, wherein $R^1$ is

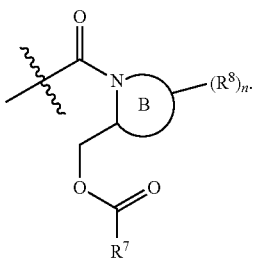

In some embodiments is a compound of Formula (III), or a pharmaceutically acceptable salt or solvate thereof, wherein $R^1$ is

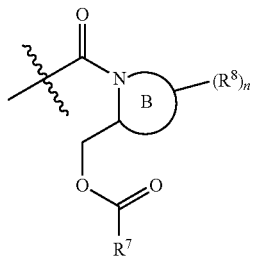

and Ring B is $C_{2-9}$heteroaryl. In some embodiments is a compound of Formula (III), or a pharmaceutically acceptable salt or solvate thereof, wherein $R^1$ is

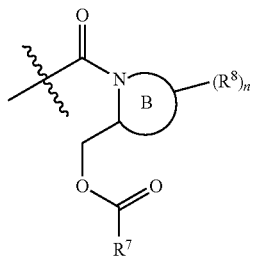

and Ring B is $C_{2-9}$heteroaryl selected from pyrazolyl, pyrrolyl, and imidazolyl.

In some embodiments is a compound of Formula (III), or a pharmaceutically acceptable salt or solvate thereof, wherein $R^1$ is

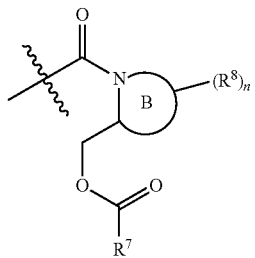

and Ring B is $C_{2-9}$heterocycloalkyl. In some embodiments is a compound of Formula (III), or a pharmaceutically acceptable salt or solvate thereof, wherein $R^1$ is

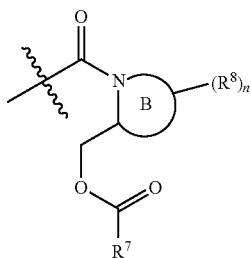

and Ring B is $C_{2-9}$heterocycloalkyl selected from pyrrolidinyl, piperidinyl, morpholinyl, and piperazinyl.

In some embodiments is a compound of Formula (III), or a pharmaceutically acceptable salt or solvate thereof, wherein n is 0, 1, or 2. In some embodiments is a compound of Formula (III), or a pharmaceutically acceptable salt or solvate thereof, wherein n is 2. In some embodiments is a compound of Formula (III), or a pharmaceutically acceptable salt or solvate thereof, wherein n is 1. In some embodiments is a compound of Formula (III), or a pharmaceutically acceptable salt or solvate thereof, wherein n is 0.

In some embodiments is a compound of Formula (III), or a pharmaceutically acceptable salt or solvate thereof, wherein each $R^8$ is independently selected from halogen and unsubstituted $C_{1-6}$alkyl. In some embodiments is a compound of Formula (III), or a pharmaceutically acceptable salt or solvate thereof, wherein n is 1 or 2 and each $R^8$ is independently selected from halogen and unsubstituted $C_{1-6}$alkyl. In some embodiments is a compound of Formula (III), or a pharmaceutically acceptable salt or solvate thereof, wherein n is 1 and $R^8$ is halogen. In some embodiments is a compound of Formula (III), or a pharmaceutically acceptable salt or solvate thereof, wherein n is 1 and $R^8$ is unsubstituted $C_{1-6}$alkyl.

In some embodiments is a compound of Formula (III), or a pharmaceutically acceptable salt or solvate thereof, wherein $R^3$, $R^4$, and $R^5$ are each independently selected from H, halogen, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{13}$. In some embodiments is a compound of Formula (III), or a pharmaceutically acceptable salt or solvate thereof, wherein $R^3$, $R^4$, and $R^5$ are each independently selected from H, halogen, and $C_{1-6}$alkyl optionally substituted with one, two, or three $R^{13}$. In some embodiments is a compound of Formula (III), or a pharmaceutically acceptable salt or solvate thereof, wherein $R^3$, $R^4$, and $R^5$ are each independently selected from H, halogen, and unsubstituted $C_{1-6}$alkyl. In some embodiments is a compound of Formula (III), or a pharmaceutically acceptable salt or solvate thereof, wherein $R^3$, $R^4$, and $R^5$ are each independently selected from H and halogen. In some embodiments is a compound of Formula (III), or a pharmaceutically acceptable salt or solvate thereof, wherein $R^3$, $R^4$, and $R^5$ are each independently halogen.

In some embodiments is a compound of Formula (III), or a pharmaceutically acceptable salt or solvate thereof, wherein $R^3$ and $R^4$ are each —Cl and $R^5$ is —F. In some embodiments is a compound of Formula (III), or a pharmaceutically acceptable salt or solvate thereof, wherein $R^4$ is —Cl, $R^3$ is —Br, and $R^5$ is —F. In some embodiments is a compound of Formula (III), or a pharmaceutically acceptable salt or solvate thereof, wherein $R^3$, $R^4$, and $R^5$ are each —Cl. In some embodiments is a compound of Formula (III), or a pharmaceutically acceptable salt or solvate thereof, wherein $R^4$ and $R^5$ are each —Cl and $R^3$ is —Br. In some embodiments is a compound of Formula (III), or a pharmaceutically acceptable salt or solvate thereof, wherein $R^3$ is —Cl, and $R^4$ and $R^5$ are each —F. In some embodiments is a compound of Formula (III), or a pharmaceutically acceptable salt or solvate thereof, wherein $R^3$ is —Br, and $R^4$ and $R^5$ are each —F. In some embodiments is a compound of Formula (III), or a pharmaceutically acceptable salt or solvate thereof, wherein $R^5$ is —F, $R^3$ is H, and $R^4$ is —C$_1$. In some embodiments is a compound of Formula (III), or a pharmaceutically acceptable salt or solvate thereof, wherein $R^4$ is —Cl, and $R^3$ and $R^5$ are each —F. In some embodiments is a compound of Formula (III), or a pharmaceutically acceptable salt or solvate thereof, wherein $R^3$ is H, and $R^4$ and $R^5$ are each —Cl. In some embodiments is a compound of Formula (III), or a pharmaceutically acceptable salt or solvate thereof, wherein $R^4$ and $R^5$ are each —Cl and $R^3$ is —F. In some embodiments is a compound of Formula (III), or a pharmaceutically acceptable salt or solvate thereof, wherein $R^3$ is H, and $R^4$ and $R^5$ are each —F. In some embodiments is a compound of Formula (III), or a pharmaceutically acceptable salt or solvate thereof, wherein $R^3$, $R^4$, and $R^5$ are each —F. In some embodiments is a compound of Formula (III), or a pharmaceutically acceptable salt or solvate thereof, wherein $R^3$ is —Br, $R^4$ is —Cl, and $R^5$ is —F. In some embodiments is a compound of Formula (III), or a pharmaceutically acceptable salt or solvate thereof, wherein $R^3$ is —Br, and $R^4$ and $R^5$ are each —Cl. In some embodiments is a compound of Formula (III), or a pharmaceutically acceptable salt or solvate thereof, wherein $R^3$ is —Br, and $R^4$ and $R^5$ are each —F.

In some embodiments is a compound of Formula (III), or a pharmaceutically acceptable salt or solvate thereof, wherein $R^6$ is H. In some embodiments is a compound of Formula (III), or a pharmaceutically acceptable salt or solvate thereof, wherein $R^6$ is $C_{1-6}$alkyl. In some embodiments is a compound of Formula (III), or a pharmaceutically acceptable salt or solvate thereof, wherein $R^6$ is —CH$_3$.

In some embodiments is a compound of Formula (III) having the structure of Formula (IIIa):

wherein:

Formula (IIIa)

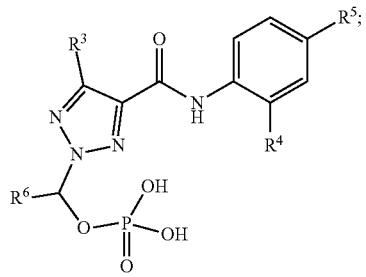

$R^3$, $R^4$, and $R^5$ are each independently selected from H, halogen, —CN, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —OR$^{10}$, —SR$^{10}$, —N(R$^{10}$)$_2$, —C(O)OR$^{10}$, —C(O)N(R$^{10}$)$_2$, —OC(O)N(R$^{10}$)$_2$, —N(R$^{11}$)C(O)N(R$^{10}$)$_2$, —N(R$^{11}$)C(O)OR$^{10}$, —N(R$^{11}$)C(O)R$^{12}$, —N(R$^{11}$)S(O)$_2$R$^{12}$, —C(O)R$^{12}$, —S(O)R$^{12}$, —S(O)$_2$R$^{12}$, —S(O)$_2$N(R$^{10}$)$_2$, and —OC(O)R$^{12}$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three R$^{13}$;

$R^6$ is selected from H, $C_{1-6}$alkyl, and $C_{1-6}$haloalkyl;

each R$^{10}$ is independently selected from H, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl; each R$^{11}$ is independently selected from H, $C_{1-6}$alkyl, and $C_{1-6}$haloalkyl;

each R$^{12}$ is independently selected from $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three R$^{13}$;

each R$^{13}$ is independently selected from halogen, —CN, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —OR$^{15}$, —SR$^{15}$, —N(R$^{16}$)(R$^{17}$), —C(O)OR$^{16}$, —C(O)N(R$^{16}$)(R$^{17}$), —C(O)C(O)N(R$^{16}$)(R$^{17}$), —OC(O)N(R$^{16}$)(R$^{17}$), —N(R$^{18}$)C(O)N(R$^{16}$)(R$^{17}$), —N(R$^{18}$)C(O)OR$^{19}$, —N(R$^{18}$)C(O)R$^{19}$, —N(R$^{18}$)S(O)$_2$R$^{19}$, —C(O)R$^{19}$, —S(O)$_2$R$^{19}$, —S(O)$_2$N(R$^{16}$)(R$^{17}$), and —OC(O)R$^{19}$, wherein $C_{1-6}$alkyl, $C_{2-6}$alkenyl, $C_{2-6}$alkynyl, $C_{3-6}$cycloalkyl, —CH$_2$—$C_{3-6}$cycloalkyl, $C_{2-9}$heterocycloalkyl, —CH$_2$—$C_{2-9}$heterocycloalkyl, $C_{6-10}$aryl, —CH$_2$—$C_{6-10}$aryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{15}$, —SR$^{15}$, —N(R$^{15}$)$_2$, —C(O)OR$^{15}$, —C(O)N(R$^{15}$)$_2$, —C(O)C(O)N(R$^{15}$)$_2$, —OC(O)N(R$^{15}$)$_2$, —N(R$^{16}$)C(O)N(R$^{15}$)$_2$, —N(R$^{16}$)C(O)OR$^{15}$, —N(R$^{16}$)C(O)R$^{17}$, —N(R$^{16}$)S(O)$_2$R$^{17}$, —C(O)R$^{17}$, —S(O)$_2$R$^{17}$, —S(O)$_2$N(R$^{15}$)$_2$, and —OC(O)R$^{17}$;

each R$^{15}$ is independently selected from H, $C_{1-6}$alkyl, $C_6$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl;

each R$^{16}$ is independently selected from H and $C_{1-6}$alkyl;

each R$^{17}$ is selected from $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl;

each R$^{18}$ is independently selected from H and $C_{1-6}$alkyl; and each R$^{19}$ is selected from $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl;

or a pharmaceutically acceptable salt or solvate thereof.

In some embodiments is a compound of Formula (IIIa), or a pharmaceutically acceptable salt or solvate thereof, wherein $R^3$, $R^4$, and $R^5$ are each independently selected from H, halogen, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three R$^{13}$. In some embodiments is a compound of Formula (IIIa), or a pharmaceutically acceptable salt or solvate thereof, wherein $R^3$, $R^4$, and $R^5$ are each independently selected from H, halogen, and $C_{1-6}$alkyl optionally substituted with one, two, or three R$^{13}$. In some embodiments is a compound of Formula (IIIa), or a pharmaceutically acceptable salt or solvate thereof, wherein $R^3$, $R^4$, and $R^5$ are each independently selected from H, halogen, and unsubstituted $C_{1-6}$alkyl. In some embodiments is a compound of Formula (IIIa), or a pharmaceutically acceptable salt or solvate thereof, wherein $R^3$, $R^4$, and $R^5$ are each independently selected from H and halogen. In some embodiments is a compound of Formula (IIIa), or a pharmaceutically acceptable salt or solvate thereof, wherein $R^3$, $R^4$, and $R^5$ are each independently halogen.

In some embodiments is a compound of Formula (IIIa), or a pharmaceutically acceptable salt or solvate thereof, wherein $R^3$ and $R^4$ are each —Cl and $R^5$ is —F. In some embodiments is a compound of Formula (IIIa), or a pharmaceutically acceptable salt or solvate thereof, wherein $R^4$ is —Cl, $R^3$ is —Br, and $R^5$ is —F. In some embodiments is a compound of Formula (IIIa), or a pharmaceutically acceptable salt or solvate thereof, wherein $R^3$, $R^4$, and $R^5$ are each —Cl. In some embodiments is a compound of Formula (IIIa), or a pharmaceutically acceptable salt or solvate thereof, wherein $R^4$ and $R^5$ are each —Cl and $R^3$ is —Br. In some embodiments is a compound of Formula (IIIa), or a pharmaceutically acceptable salt or solvate thereof, wherein $R^3$ is —Cl, and $R^4$ and $R^5$ are each —F. In some embodiments is a compound of Formula (IIIa), or a pharmaceutically acceptable salt or solvate thereof, wherein $R^3$ is —Br, and $R^4$ and $R^5$ are each —F. In some embodiments is a compound of Formula (IIa), or a pharmaceutically acceptable salt or solvate thereof, wherein $R^5$ is —F, $R^3$ is H, and $R^4$ is —$C_1$. In some embodiments is a compound of Formula (IIIa), or a pharmaceutically acceptable salt or solvate thereof, wherein $R^4$ is —Cl, and $R^3$ and $R^5$ are each —F. In some embodiments is a compound of Formula (IIIa), or a pharmaceutically acceptable salt or solvate thereof, wherein $R^3$ is H, and $R^4$ and $R^5$ are each —Cl. In some embodiments is a compound of Formula (IIIa), or a pharmaceutically acceptable salt or solvate thereof, wherein $R^4$ and $R^5$ are each —Cl and $R^3$ is —F. In some embodiments is a compound of Formula (IIIa), or a pharmaceutically acceptable salt or solvate thereof, wherein $R^3$ is H, and $R^4$ and $R^5$ are each —F. In some embodiments is a compound of Formula (IIIa), or a pharmaceutically acceptable salt or solvate thereof, wherein $R^3$, $R^4$, and $R^5$ are each —F. In some embodiments is a compound of Formula (IIIa), or a pharmaceutically acceptable salt or solvate thereof, wherein $R^3$ is —Br, $R^4$ is —Cl, and $R^5$ is —F. In some embodiments is a compound of Formula (IIIa), or a pharmaceutically acceptable salt or solvate thereof, wherein $R^3$ is —Br, and $R^4$ and $R^5$ are each —Cl. In some embodiments is a compound of Formula (IIIa), or a pharmaceutically acceptable salt or solvate thereof, wherein $R^3$ is —Br, and $R^4$ and $R^5$ are each —F.

In some embodiments is a compound of Formula (IIIa), or a pharmaceutically acceptable salt or solvate thereof, wherein $R^6$ is H. In some embodiments is a compound of Formula (IIIa), or a pharmaceutically acceptable salt or solvate thereof, wherein $R^6$ is $C_{1-6}$alkyl. In some embodiments is a compound of Formula (IIIa), or a pharmaceutically acceptable salt or solvate thereof, wherein $R^6$ is —$CH_3$.

In some embodiments is a compound of Formula (III) having the structure of Formula (IIIb):

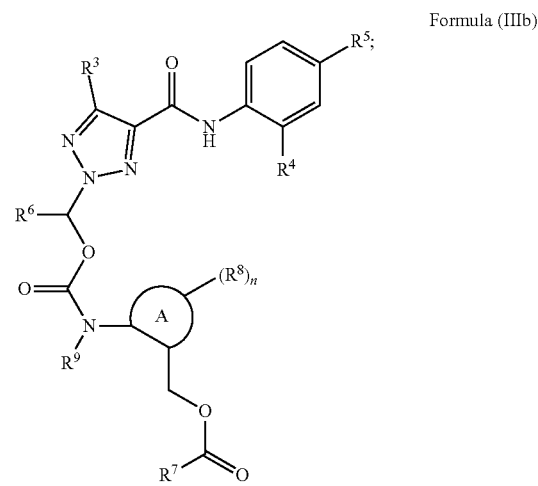

Formula (IIIb)

wherein:
Ring A is selected from $C_{3-6}$cycloalkyl, $C_{2-9}$heterocycloalkyl, $C_{6-10}$aryl, and $C_{2-9}$heteroaryl;
$R^3$, $R^4$, and $R^5$ are each independently selected from H, halogen, —CN, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$OR^{10}$, —$SR^{10}$, —$N(R^{10})_2$, —$C(O)OR^{10}$, —$C(O)N(R^{10})_2$, —$OC(O)N(R^{10})_2$, —$N(R^{11})C(O)N(R^{10})_2$, —$N(R^{11})C(O)OR^{10}$, —$N(R^{11})C(O)R^{12}$, —$N(R^{11})S(O)_2R^{12}$, —$C(O)R^{12}$, —$S(O)R^{12}$, —$S(O)_2R^{12}$, —$S(O)_2N(R^1)_2$, and —$OC(O)R^{12}$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{13}$;
$R^6$ is selected from H, $C_{1-6}$alkyl, and $C_{1-6}$haloalkyl;
$R^7$ is selected from $C_{1-6}$alkyl or —$C_{1-6}$alkyl-$N(R^{14})_2$;
each $R^8$ is independently selected from halogen, —CN, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$OR^{10}$, —$SR^{10}$, —$N(R^{10})_2$, —$C(O)OR^{10}$, —$C(O)N(R^{10})_2$, —$OC(O)N(R^{10})_2$, —$N(R^{11})C(O)N(R^{10})_2$, —$N(R^{11})C(O)OR^{10}$, —$N(R^{11})C(O)R^{12}$, —$N(R^{11})S(O)_2R^{12}$, —$C(O)R^{12}$, —$S(O)R^{12}$, —$S(O)_2R^{12}$, —$S(O)_2N(R^{10})_2$, and —$OC(O)R^{12}$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{13}$;
$R^9$ is selected from H, $C_{1-6}$alkyl, and $C_6$haloalkyl;
each $R^{10}$ is independently selected from H, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl;
each $R^{11}$ is independently selected from H, $C_{1-6}$alkyl, and $C_{1-6}$haloalkyl;
each $R^{12}$ is independently selected from $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{13}$;
each $R^{13}$ is independently selected from halogen, —CN, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$OR^{15}$, —$SR^{15}$, —$N(R^{16})(R^{17})$, —$C(O)OR^{16}$, —$C(O)N(R^{16})(R^{17})$, —$C(O)C(O)N(R^{16})(R^{17})$, —$OC(O)N(R^{16})(R^{17})$, —$N(R^{11})C(O)N(R^{16})(R^{17})$, —$N(R^{18})$ C(O)OR$^{19}$, —N(R$^{18}$)C(O)R$^{19}$, —N(R$^{18}$)S(O)$_2$R$^{19}$, —C(O)R$^{19}$, —S(O)$_2$R$^{19}$, —S(O)$_2$N(R$^{16}$)(R$^{17}$), and —OC(O)R$^{19}$, wherein C$_{1-6}$alkyl, C$_{2-6}$alkenyl, C$_{2-6}$alkynyl, C$_{3-6}$cycloalkyl, —CH$_2$—C$_{3-6}$cycloalkyl, C$_{2-9}$heterocycloalkyl, —CH$_2$—C$_{2-9}$heterocycloalkyl, C$_{6-10}$aryl, —CH$_2$—C$_{6-10}$aryl, and C$_{1-9}$heteroaryl are optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{15}$, —SR$^{15}$, —N(R$^{15}$)$_2$, —C(O)OR$^{15}$, —C(O)N(R$^{15}$)$_2$, —C(O)C(O)N(R$^{15}$)$_2$, —OC(O)N(R$^{15}$)$_2$, —N(R$^{16}$)C(O)N(R$^{15}$)$_2$, —N(R$^{16}$)C(O)OR$^{15}$, —N(R$^{16}$)C(O)R$^{17}$, —N(R$^{16}$)S(O)$_2$R$^{17}$, —C(O)R$^{17}$, —S(O)$_2$R$^{17}$, —S(O)$_2$N(R$^{15}$)$_2$, and —OC(O)R$^{17}$;

each R$^{14}$ is independently selected from H, C$_{1-6}$alkyl, and C$_{1-6}$haloalkyl;

each R$^{15}$ is independently selected from H, C$_{1-6}$alkyl, C$_{1-6}$haloalkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl;

each R$^{16}$ is independently selected from H and C$_{1-6}$alkyl;

each R$^{17}$ is selected from C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl;

each R$^{18}$ is independently selected from H and C$_{1-6}$alkyl;

each R$^{19}$ is selected from C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl; and n is 0, 1, 2, 3, or 4;

or a pharmaceutically acceptable salt or solvate thereof.

In some embodiments is a compound of Formula (IIIb), or a pharmaceutically acceptable salt or solvate thereof, wherein R$^7$ is C$_{1-6}$alkyl. In some embodiments is a compound of Formula (IIIb), or a pharmaceutically acceptable salt or solvate thereof, wherein R$^7$ is —C$_{1-6}$ alkyl-N(R$^{14}$)$_2$. In some embodiments is a compound of Formula (IIIb), or a pharmaceutically acceptable salt or solvate thereof, wherein R$^7$ is —C$_{1-6}$alkyl-NH$_2$. In some embodiments is a compound of Formula (IIIb), or a pharmaceutically acceptable salt or solvate thereof, wherein R$^7$ is —C$_{1-6}$alkyl-N(H)CH$_3$.

In some embodiments is a compound of Formula (IIIb), or a pharmaceutically acceptable salt or solvate thereof, wherein R$^9$ is C$_{1-6}$alkyl. In some embodiments is a compound of Formula (IIIb), or a pharmaceutically acceptable salt or solvate thereof, wherein R$^9$ is —CH$_3$. In some embodiments is a compound of Formula (IIIb), or a pharmaceutically acceptable salt or solvate thereof, wherein R$^9$ is H.

In some embodiments is a compound of Formula (IIIb), or a pharmaceutically acceptable salt or solvate thereof, wherein n is 0, 1, or 2. In some embodiments is a compound of Formula (IIIb), or a pharmaceutically acceptable salt or solvate thereof, wherein n is 2. In some embodiments is a compound of Formula (IIIb), or a pharmaceutically acceptable salt or solvate thereof, wherein n is 1. In some embodiments is a compound of Formula (IIb), or a pharmaceutically acceptable salt or solvate thereof, wherein n is 0.

In some embodiments is a compound of Formula (IIIb), or a pharmaceutically acceptable salt or solvate thereof, wherein each R$^8$ is independently selected from halogen and unsubstituted C$_{1-6}$alkyl. In some embodiments is a compound of Formula (IIb), or a pharmaceutically acceptable salt or solvate thereof, wherein n is 1 or 2 and each R$^8$ is independently selected from halogen and unsubstituted C$_{1-6}$alkyl. In some embodiments is a compound of Formula (IIIb), or a pharmaceutically acceptable salt or solvate thereof, wherein n is 1 and R$^8$ is halogen. In some embodiments is a compound of Formula (IIIb), or a pharmaceutically acceptable salt or solvate thereof, wherein n is 1 and R$^8$ is unsubstituted C$_{1-6}$alkyl.

In some embodiments is a compound of Formula (IIIb), or a pharmaceutically acceptable salt or solvate thereof, wherein R$^3$, R$^4$, and R$^5$ are each independently selected from H, halogen, C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl, wherein C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three R$^{13}$. In some embodiments is a compound of Formula (IIIb), or a pharmaceutically acceptable salt or solvate thereof, wherein R$^3$, R$^4$, and R$^5$ are each independently selected from H, halogen, and C$_{1-6}$alkyl optionally substituted with one, two, or three R$^{13}$. In some embodiments is a compound of Formula (IIIb), or a pharmaceutically acceptable salt or solvate thereof, wherein R$^3$, R$^4$, and R$^5$ are each independently selected from H, halogen, and unsubstituted C$_{1-6}$alkyl. In some embodiments is a compound of Formula (IIIb), or a pharmaceutically acceptable salt or solvate thereof, wherein R$^3$, R$^4$, and R$^5$ are each independently selected from H and halogen. In some embodiments is a compound of Formula (IIIb), or a pharmaceutically acceptable salt or solvate thereof, wherein R$^3$, R$^4$, and R$^5$ are each independently halogen.

In some embodiments is a compound of Formula (IIIb), or a pharmaceutically acceptable salt or solvate thereof, wherein R$^3$ and R$^4$ are each —Cl and R$^5$ is —F. In some embodiments is a compound of Formula (IIIb), or a pharmaceutically acceptable salt or solvate thereof, wherein R$^4$ is —Cl, R$^3$ is —Br, and R$^5$ is —F. In some embodiments is a compound of Formula (IIIb), or a pharmaceutically acceptable salt or solvate thereof, wherein R$^3$, R$^4$, and R$^5$ are each —Cl. In some embodiments is a compound of Formula (IIIb), or a pharmaceutically acceptable salt or solvate thereof, wherein R$^4$ and R$^5$ are each —Cl and R$^3$ is —Br. In some embodiments is a compound of Formula (IIIb), or a pharmaceutically acceptable salt or solvate thereof, wherein R$^3$ is —Cl, and R$^4$ and R$^5$ are each —F. In some embodiments is a compound of Formula (IIIb), or a pharmaceutically acceptable salt or solvate thereof, wherein R$^3$ is —Br, and R$^4$ and R$^5$ are each —F. In some embodiments is a compound of Formula (IIIb), or a pharmaceutically acceptable salt or solvate thereof, wherein R$^5$ is —F, R$^3$ is H, and R$^4$ is —C$_1$. In some embodiments is a compound of Formula (IIIb), or a pharmaceutically acceptable salt or solvate thereof, wherein R$^4$ is —Cl, and R$^3$ and R$^5$ are each —F. In some embodiments is a compound of Formula (IIIb), or a pharmaceutically acceptable salt or solvate thereof, wherein R$^3$ is H, and R$^4$ and R$^5$ are each —Cl. In some embodiments is a compound of Formula (IIIb), or a pharmaceutically acceptable salt or solvate thereof, wherein R$^4$ and R$^5$ are each —Cl and R$^3$ is —F. In some embodiments is a compound of Formula (IIIb), or a pharmaceutically acceptable salt or solvate thereof, wherein R$^3$ is H, and R$^4$ and R$^5$ are each —F. In some embodiments is a compound of Formula (IIIb), or a pharmaceutically acceptable salt or solvate thereof, wherein R$^3$, R$^4$, and R$^5$ are each —F. In some embodiments is a compound of Formula (IIb), or a pharmaceutically acceptable salt or solvate thereof, wherein R$^3$ is —Br, R$^4$ is —Cl, and R$^5$ is —F. In some embodiments is a compound of Formula (IIIb), or a pharmaceutically acceptable salt or solvate thereof, wherein R$^3$ is —Br, and R$^4$ and R$^5$ are each —Cl. In some embodiments is a compound of Formula (IIIb), or a pharmaceutically acceptable salt or solvate thereof, wherein $R^3$ is —Br, and $R^4$ and $R^5$ are each —F.

In some embodiments is a compound of Formula (IIIb), or a pharmaceutically acceptable salt or solvate thereof, wherein $R^6$ is H. In some embodiments is a compound of Formula (IIIb), or a pharmaceutically acceptable salt or solvate thereof, wherein $R^6$ is $C_{1-6}$alkyl. In some embodiments is a compound of Formula (IIIb), or a pharmaceutically acceptable salt or solvate thereof, wherein $R^6$ is —$CH_3$.

Any combination of the groups described above for the various variables is contemplated herein.

Throughout the specification, groups and substituents thereof can be chosen to provide stable moieties and compounds.

In some embodiments, the compound disclosed herein is a compound of any one of the compounds described herein, or a pharmaceutically acceptable salt or solvate thereof.

In some embodiments is a compound, or a pharmaceutically acceptable salt or solvate thereof, having the structure:

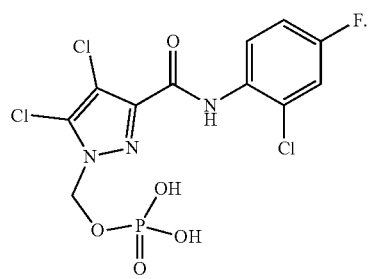 [SMILES: O=C(Nc1ccc(F)cc1Cl)c1nn(COP(=O)(O)O)c(Cl)c1Cl]

In some embodiments is a compound, or a pharmaceutically acceptable salt or solvate thereof, selected from:

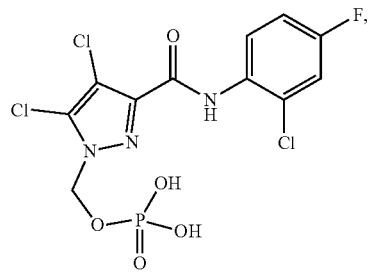

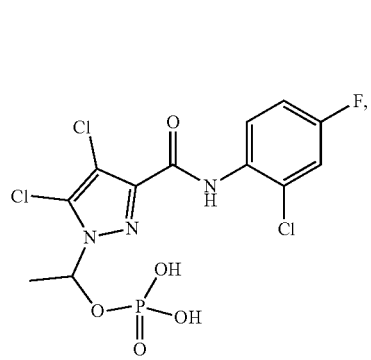

-continued

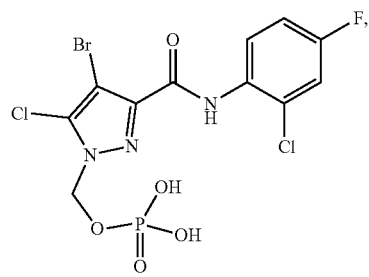

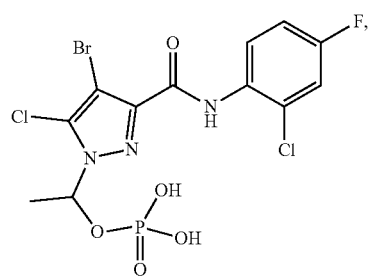

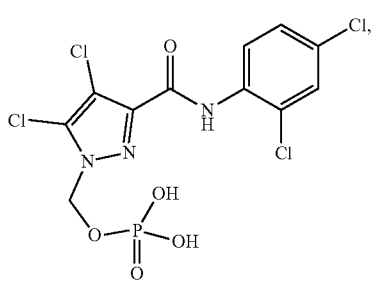

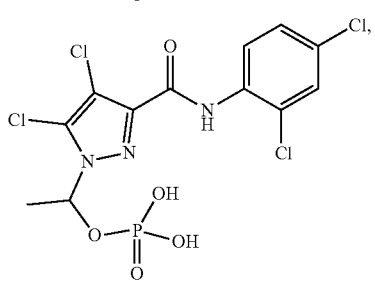

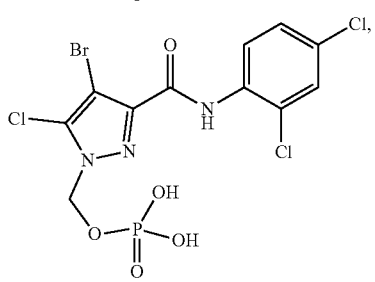

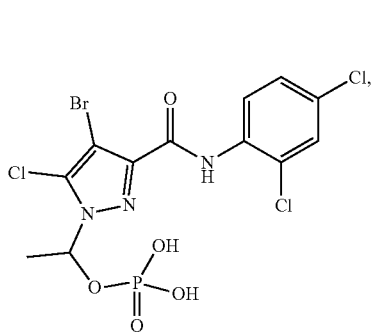

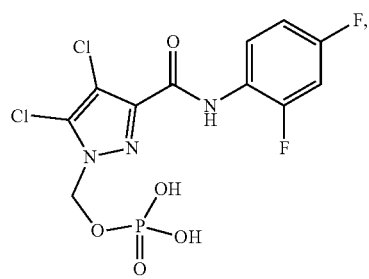
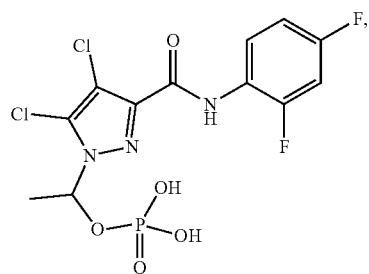
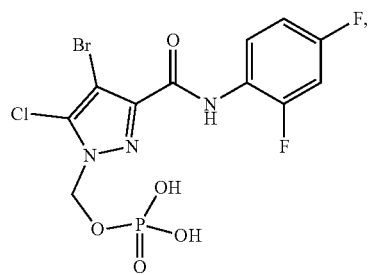
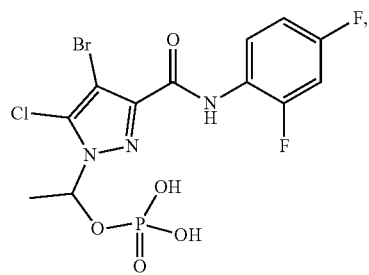
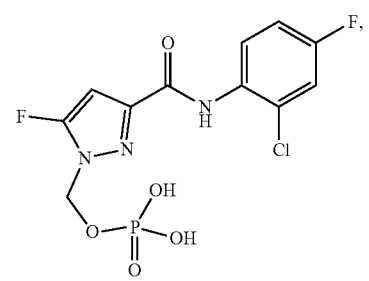
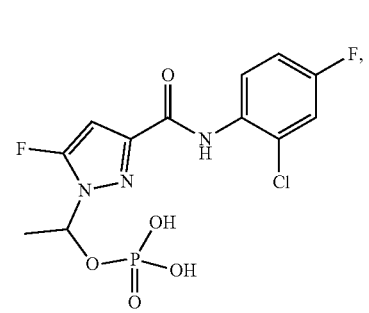
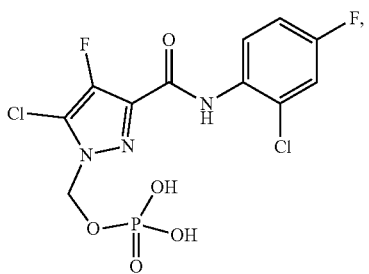
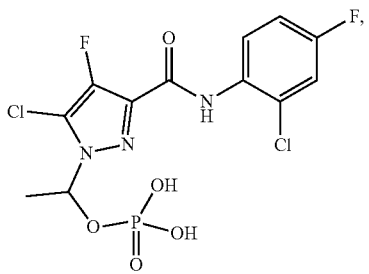
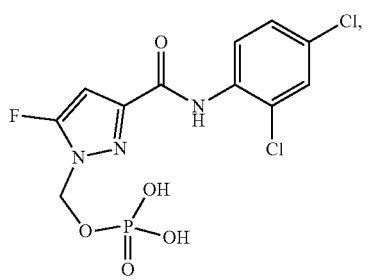
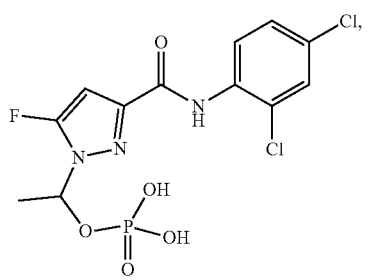
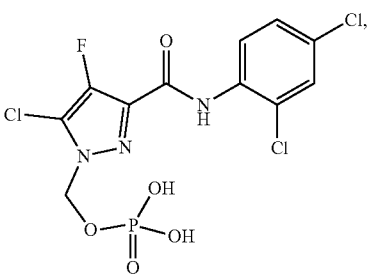
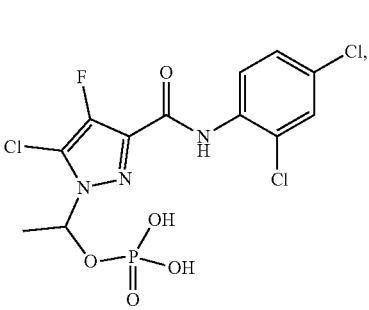

57
-continued
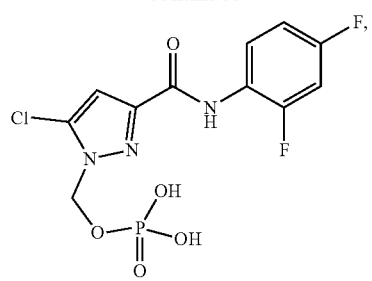
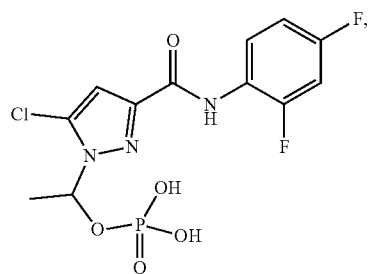
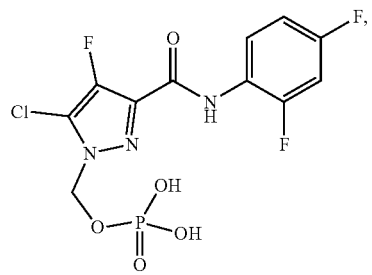
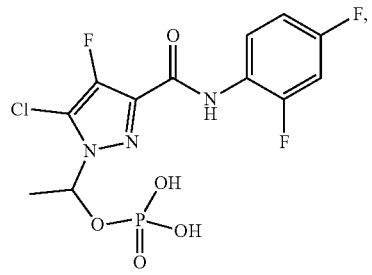
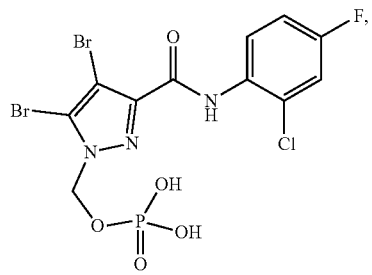
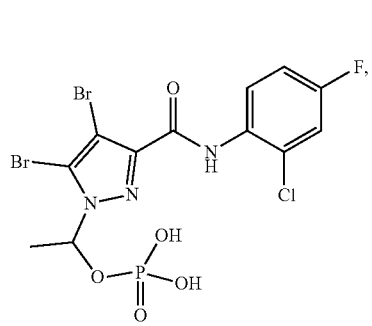
58
-continued
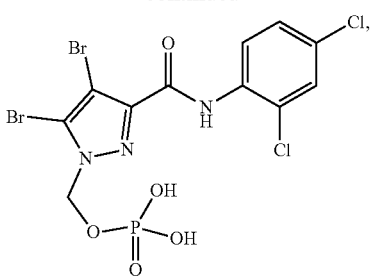
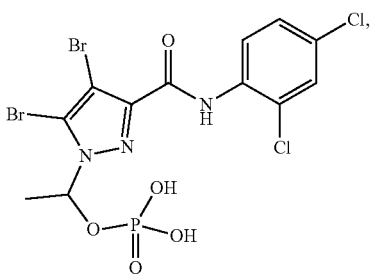
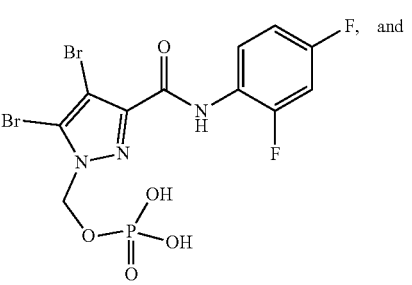
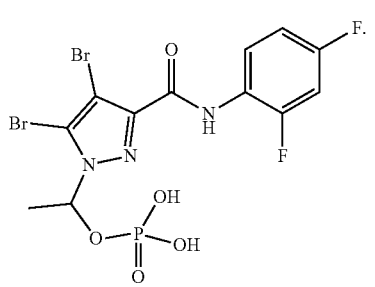
In some embodiments is a compound, or a pharmaceutically acceptable salt or solvate thereof, selected from:
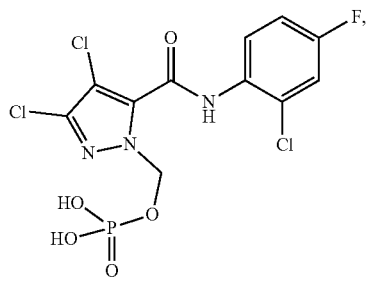

-continued
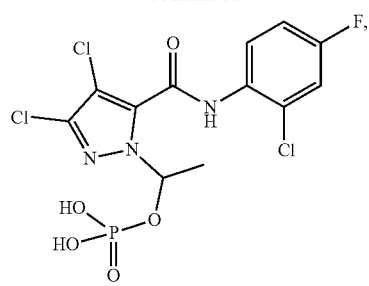
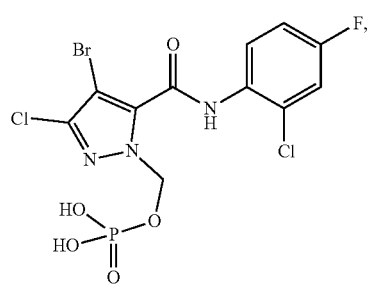
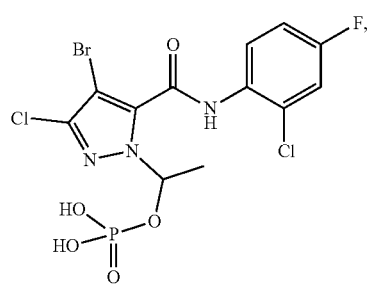
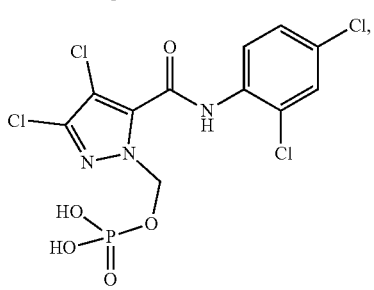
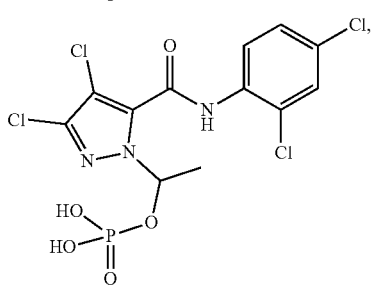
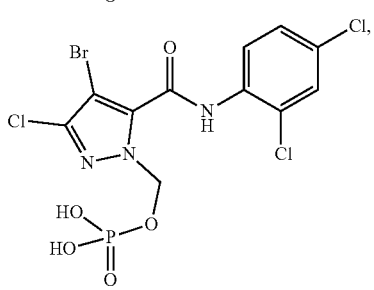
-continued
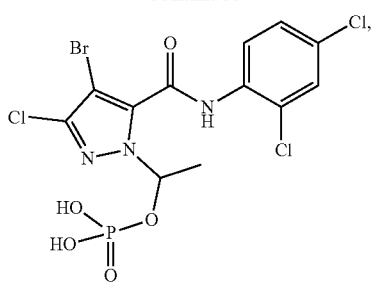
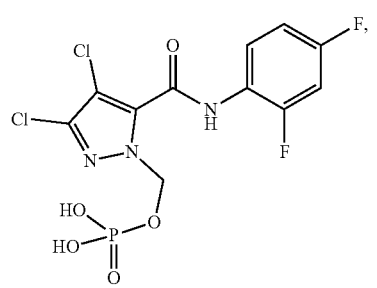
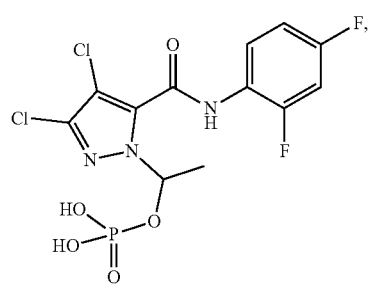
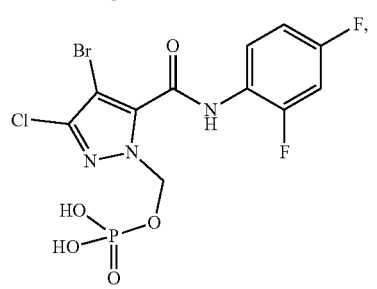
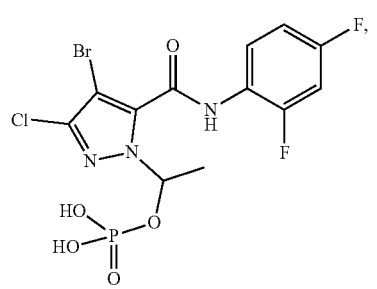
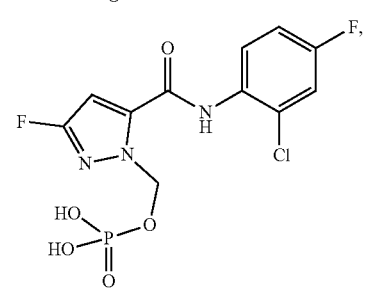

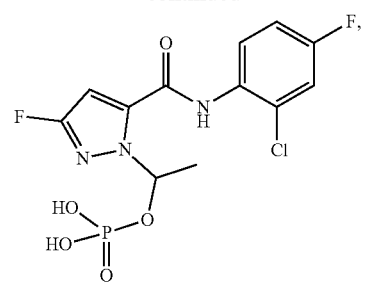
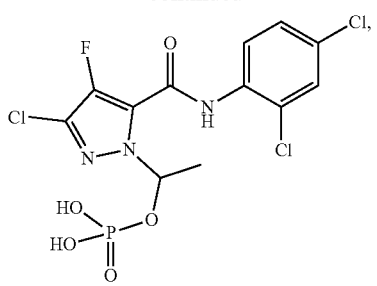

63
-continued
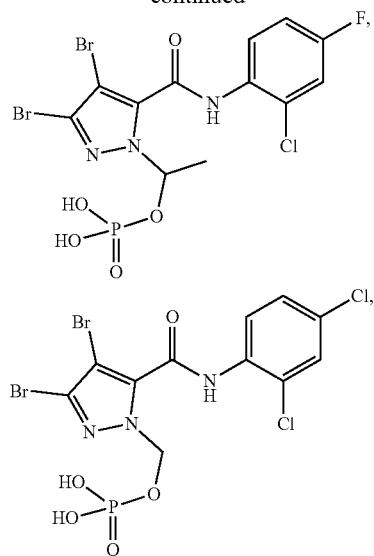
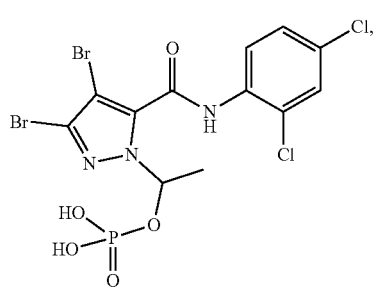
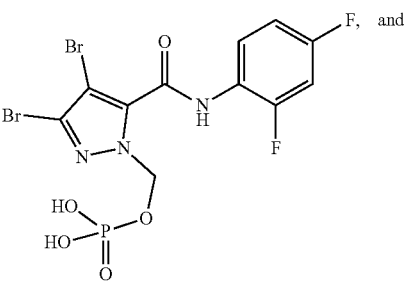
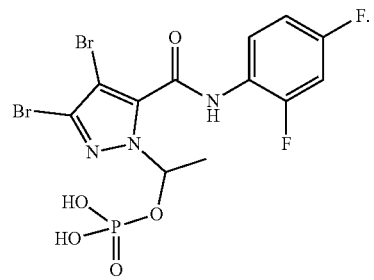, and
64
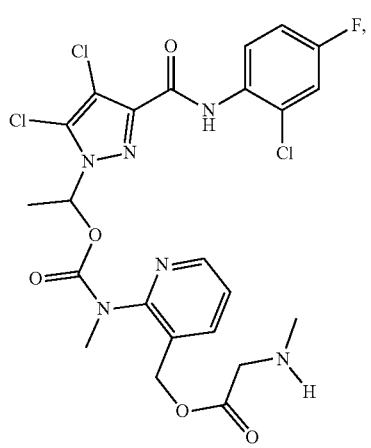
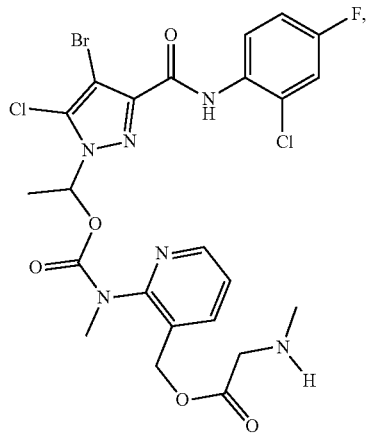
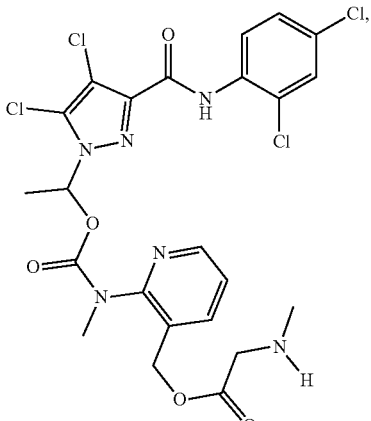
In some embodiments is a compound, or a pharmaceutically acceptable salt or solvate thereof, selected from:

65
-continued
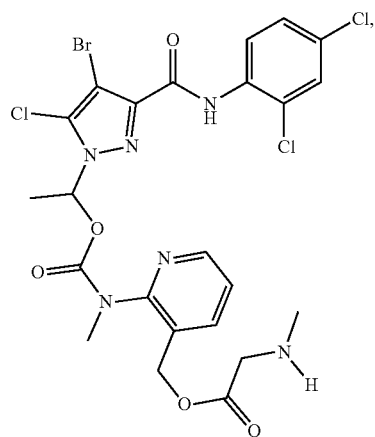
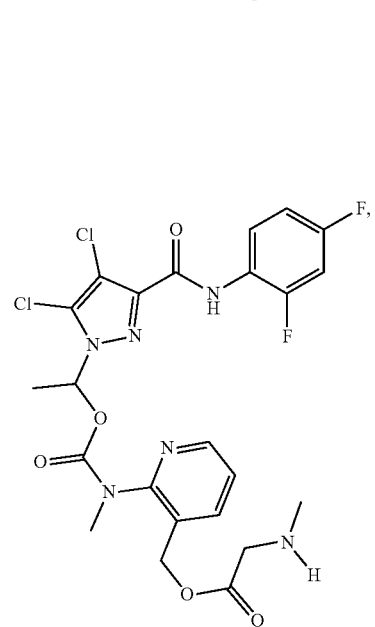
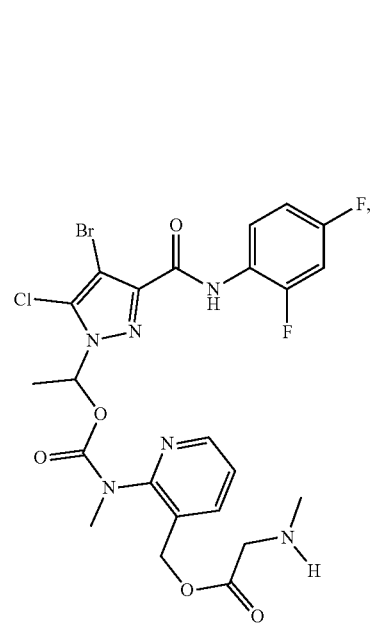
66
-continued
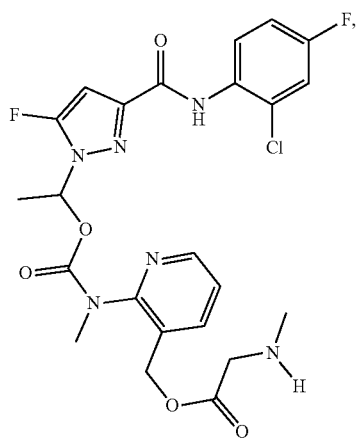
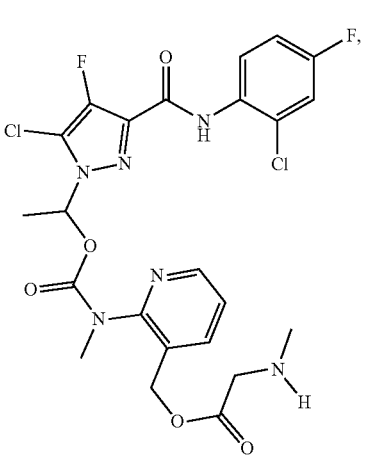
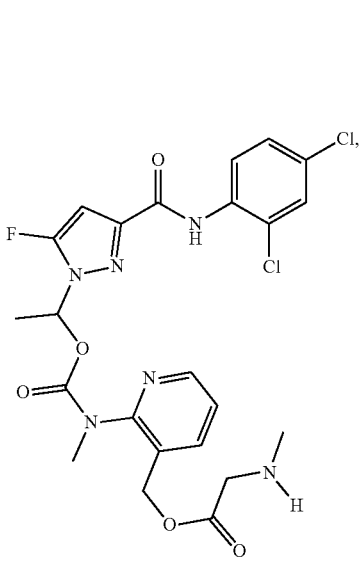

67
-continued
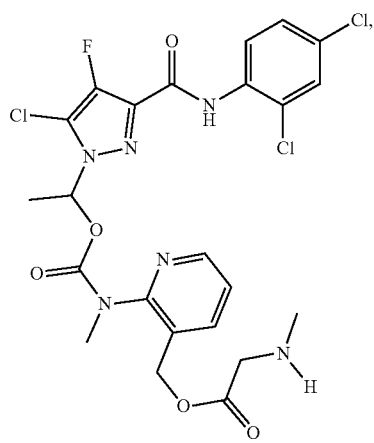
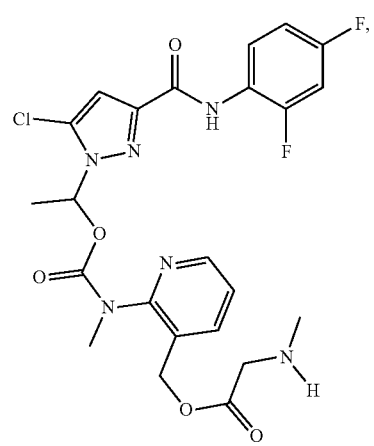
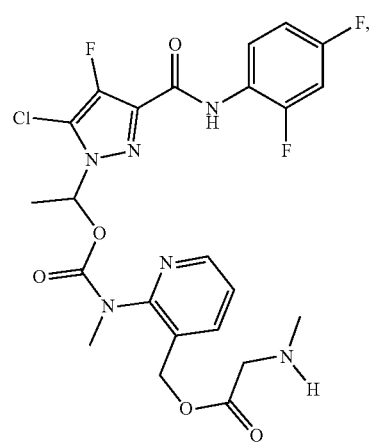
68
-continued
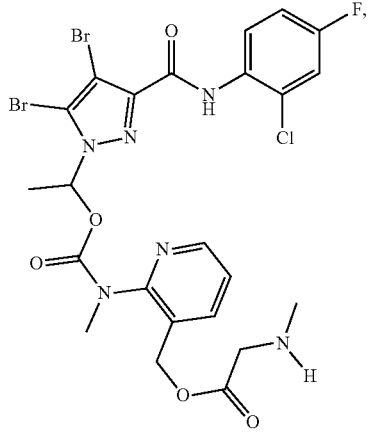
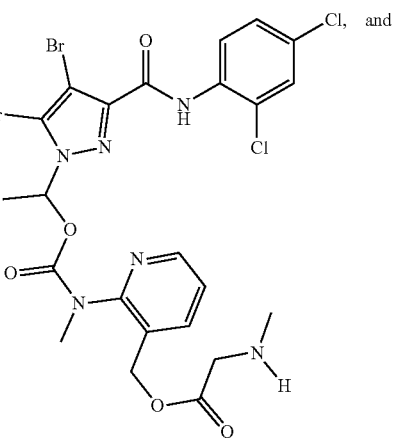
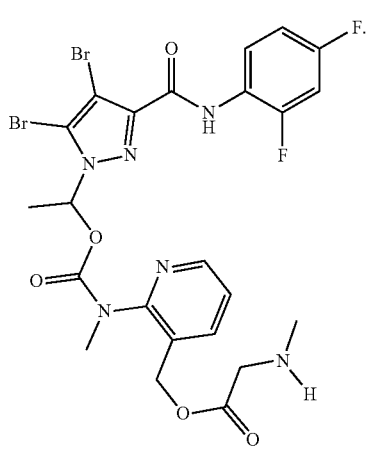
In some embodiments is a compound, or a pharmaceutically acceptable salt or solvate thereof, selected from:

69
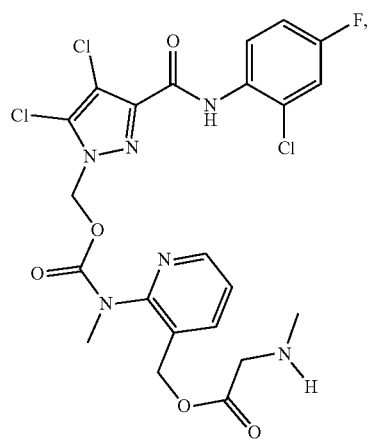
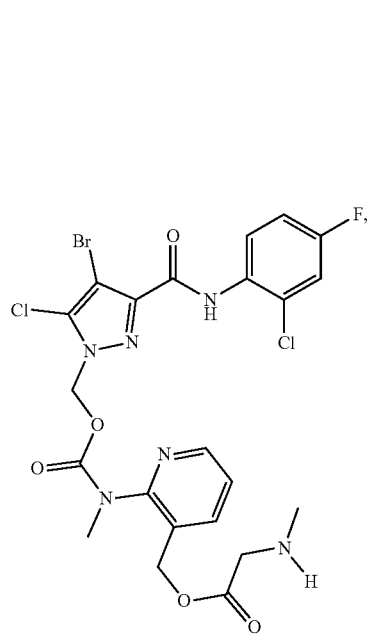
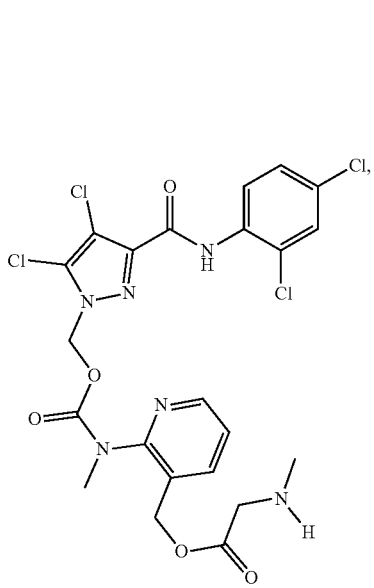
70
-continued
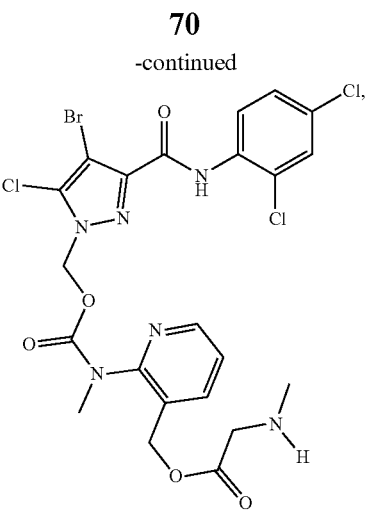
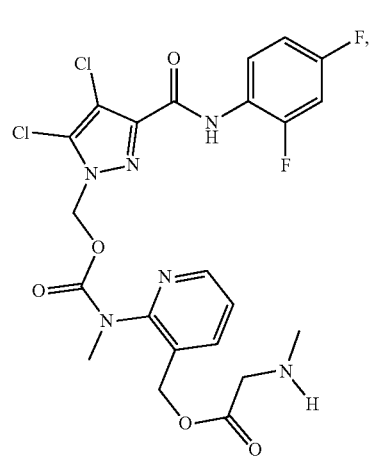
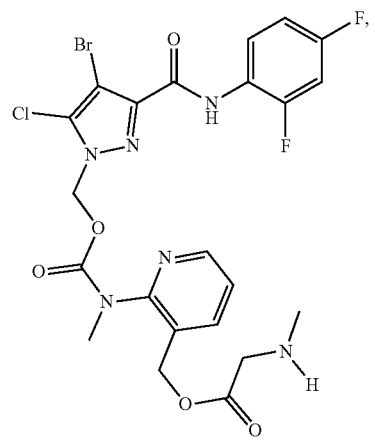

71
-continued
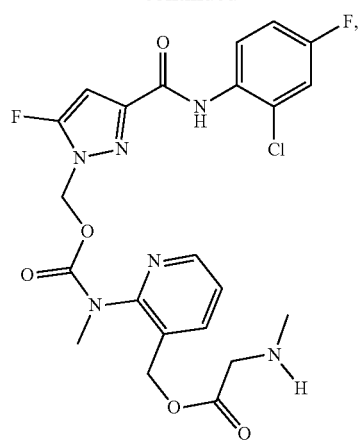
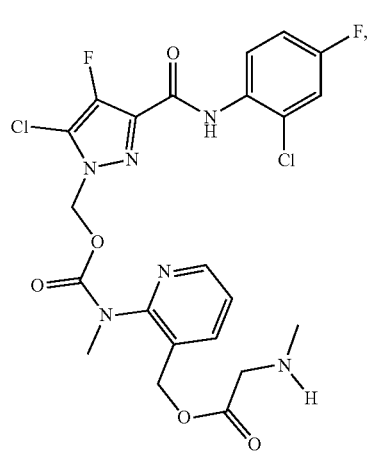
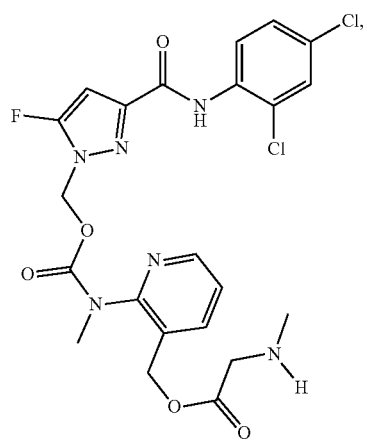
72
-continued
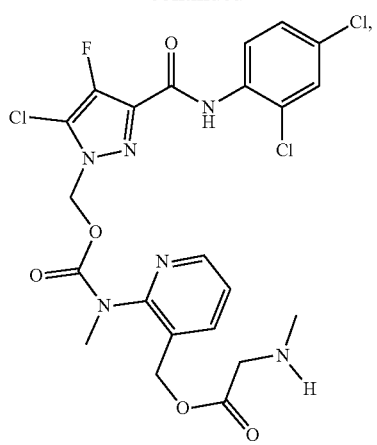
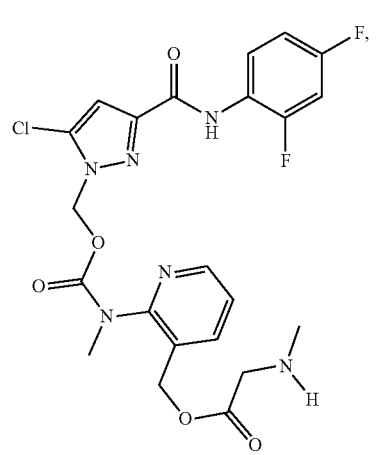
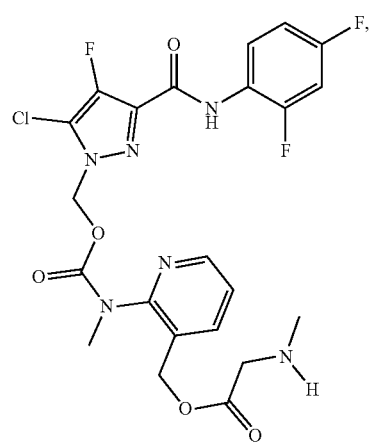

73
-continued
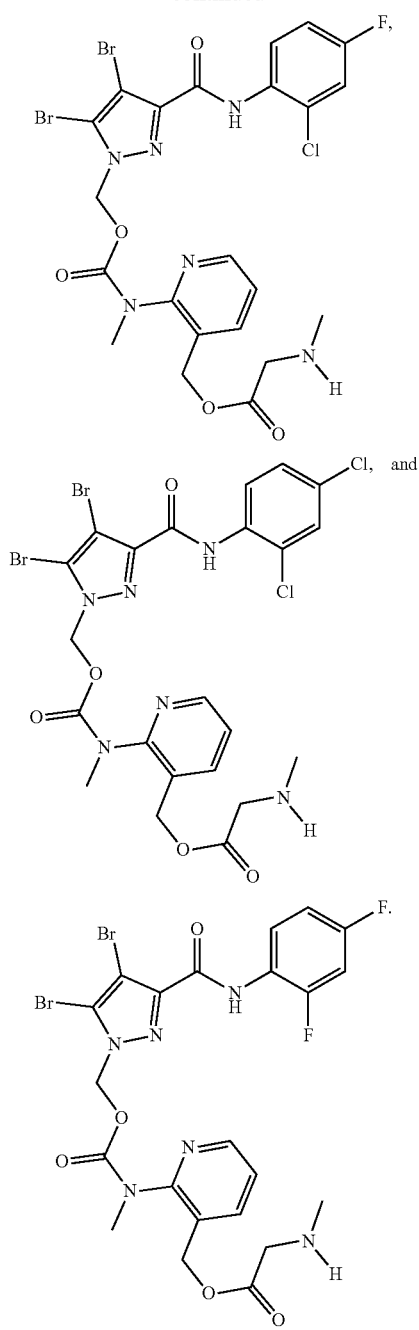
In some embodiments is a compound, or a pharmaceutically acceptable salt or solvate thereof, selected from:
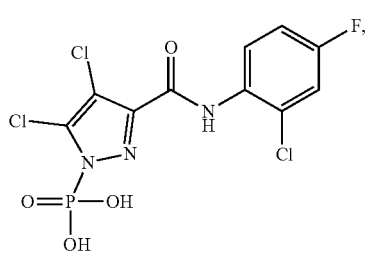
74
-continued
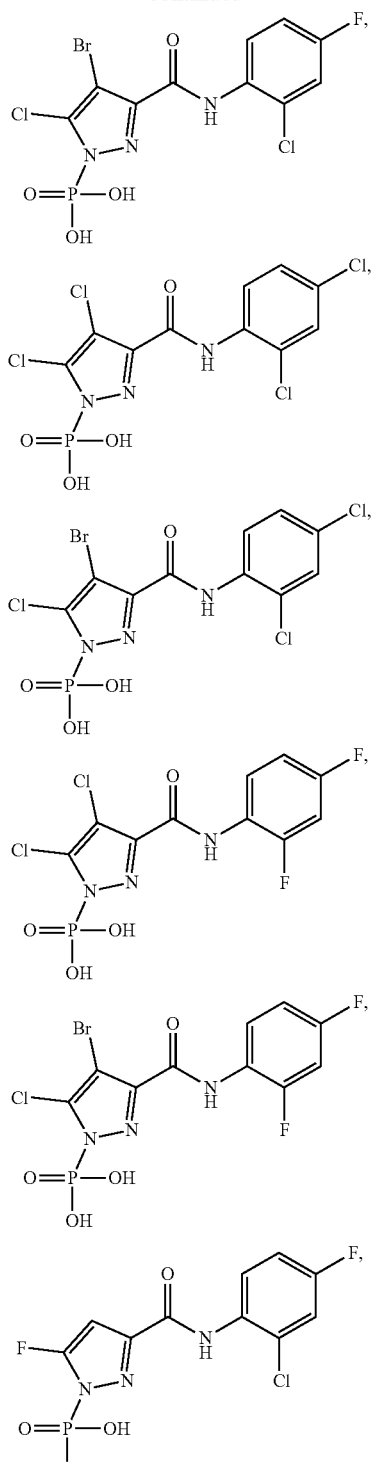
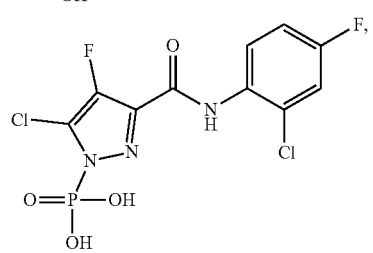

-continued
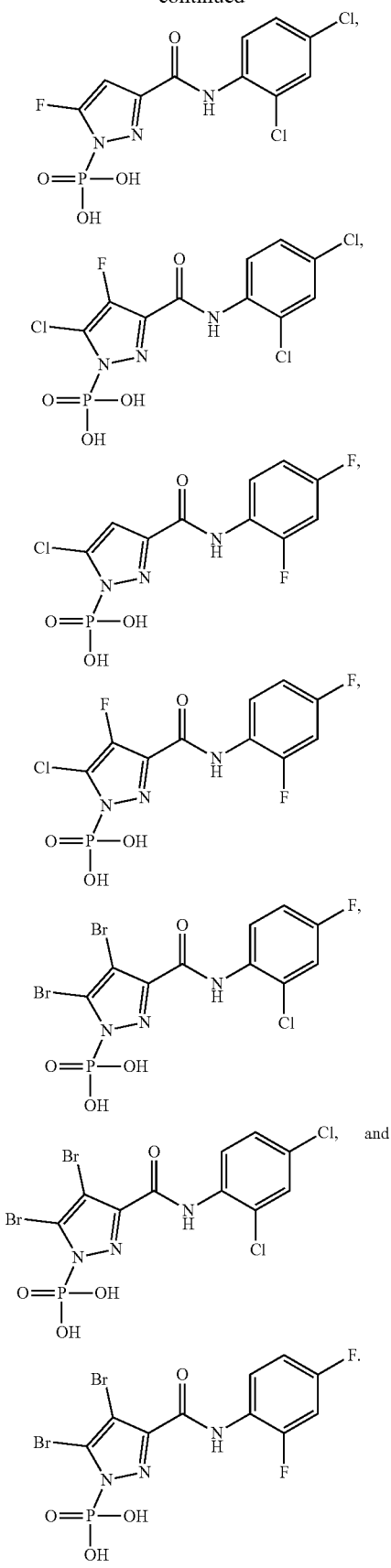
In some embodiments is a compound, or a pharmaceutically acceptable salt or solvate thereof, selected from:
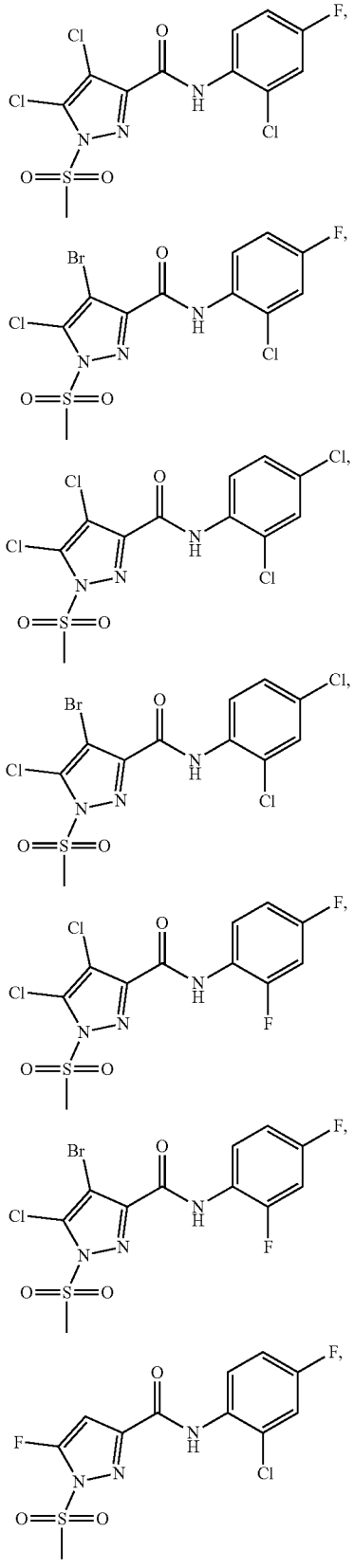

-continued
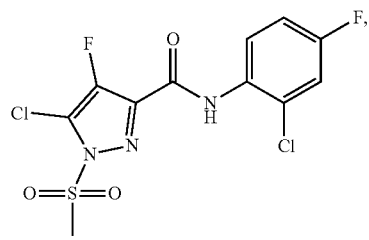
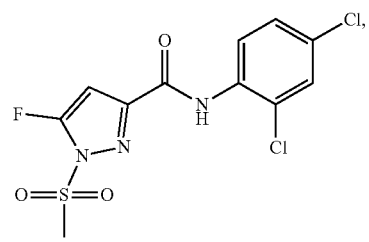
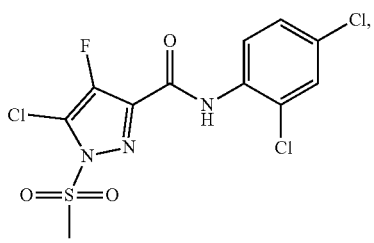
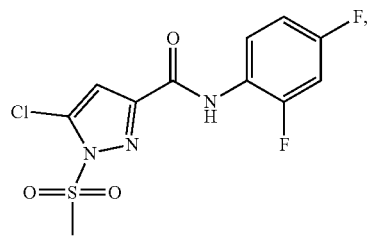
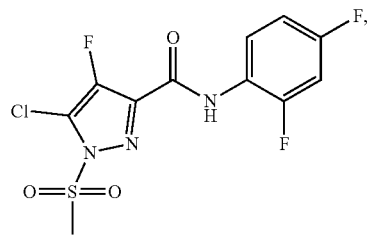
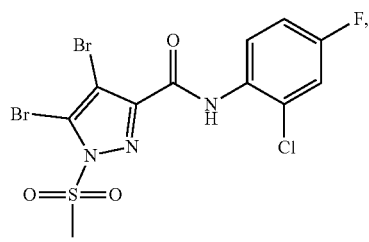
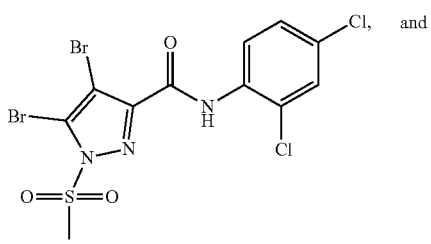
-continued
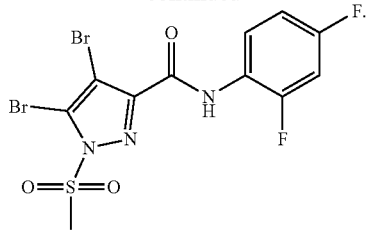
In some embodiments is a compound, or a pharmaceutically acceptable salt or solvate thereof, selected from:
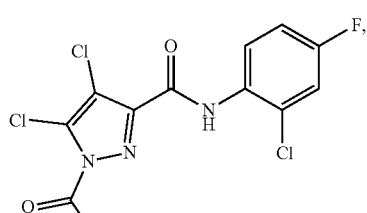
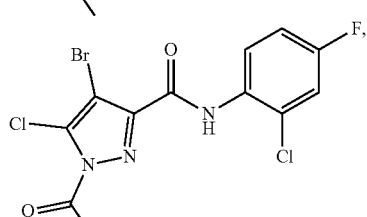
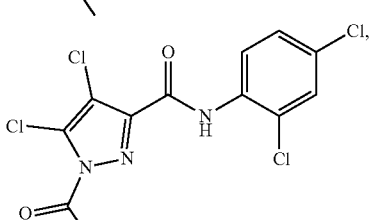
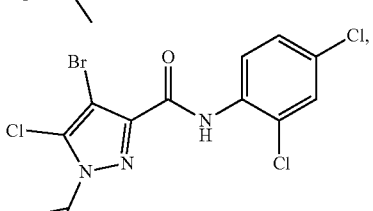
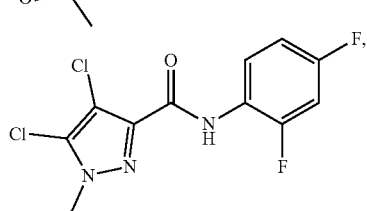
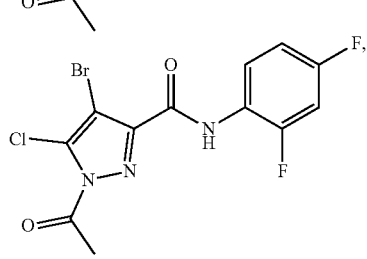

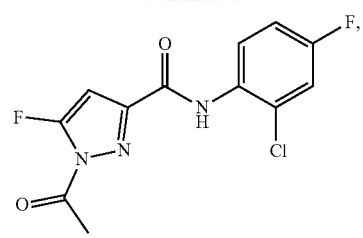
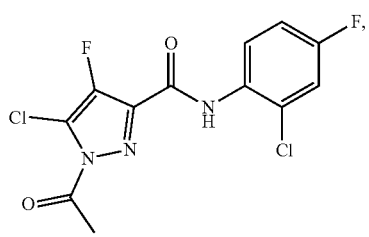
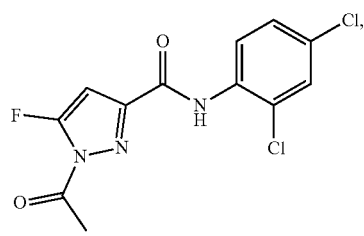
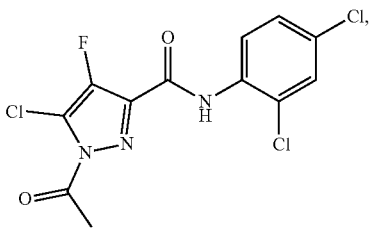
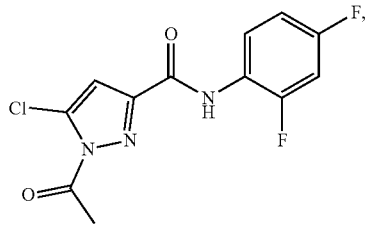
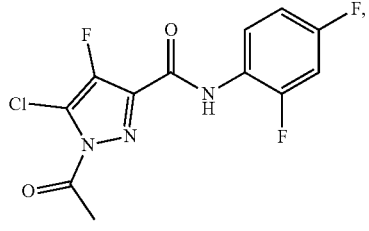
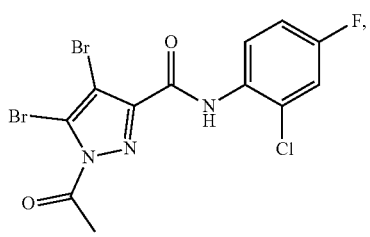
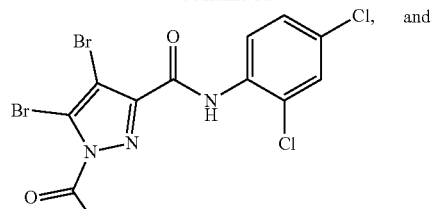
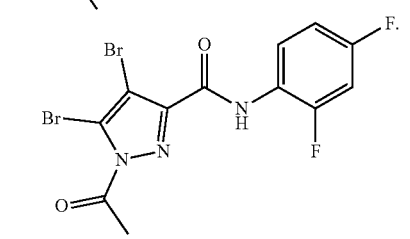
In some embodiments is a compound, or a pharmaceutically acceptable salt or solvate thereof, selected from:
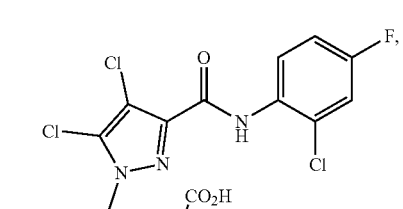
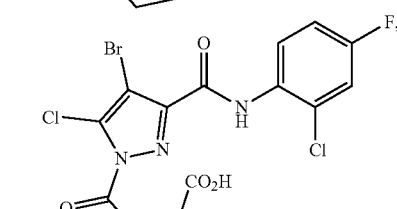
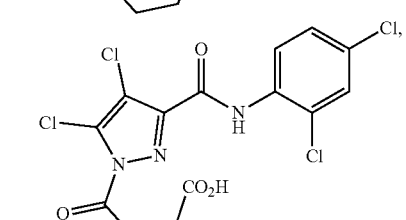
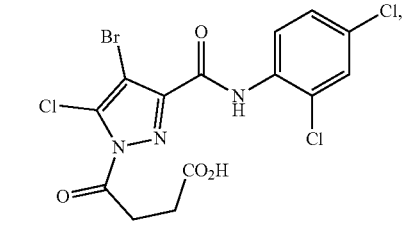
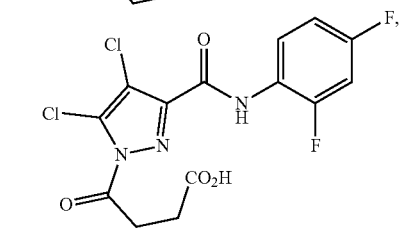

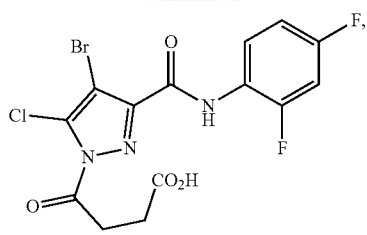
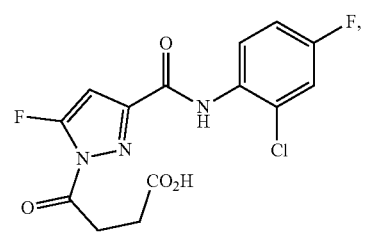
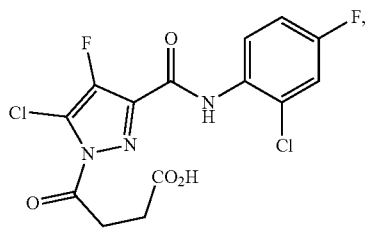
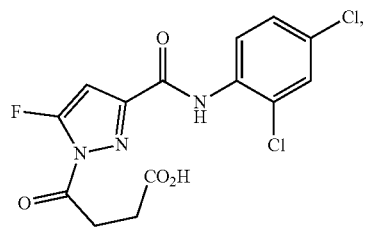
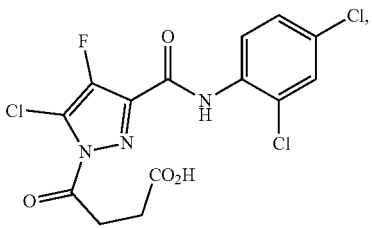
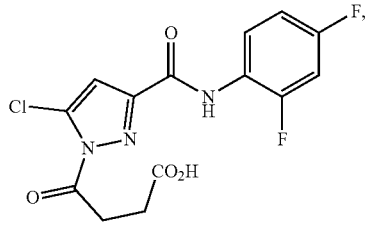
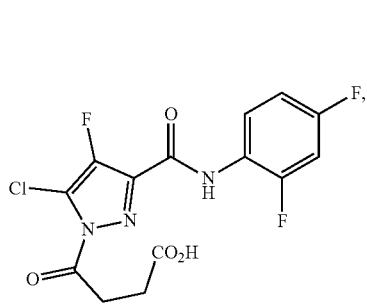
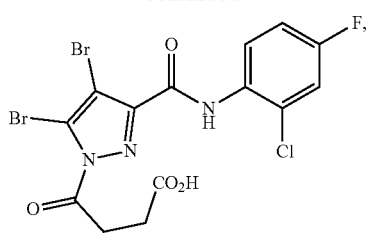
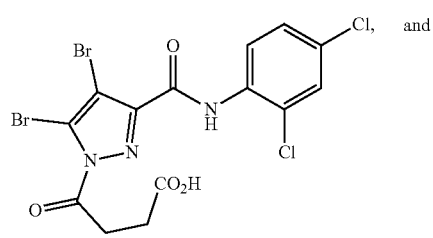
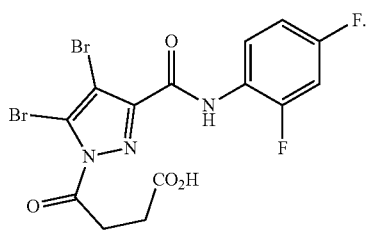
In some embodiments is a compound, or a pharmaceutically acceptable salt or solvate thereof, selected from:
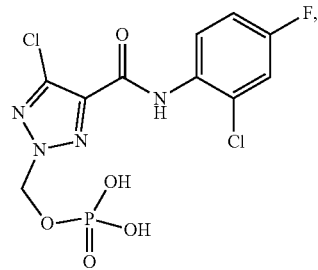
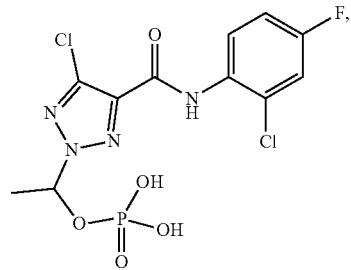
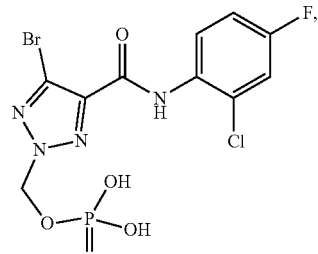

83
-continued
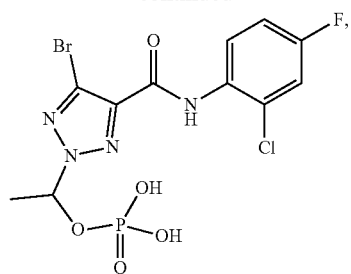
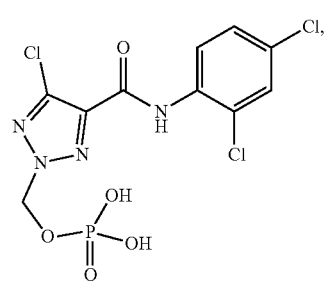
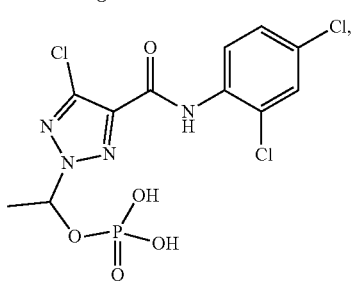
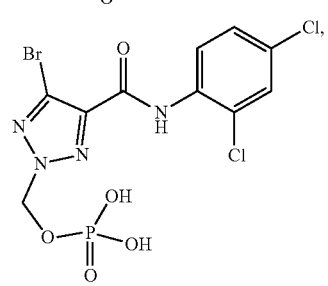
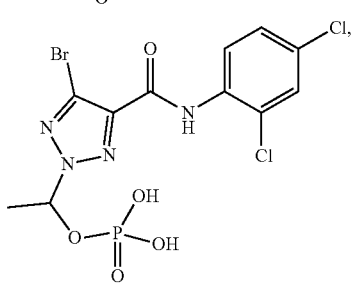
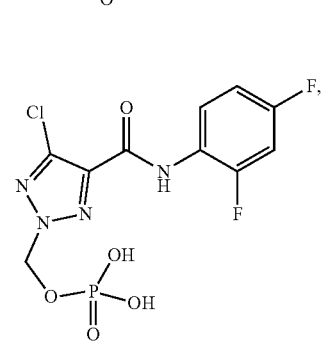
84
-continued
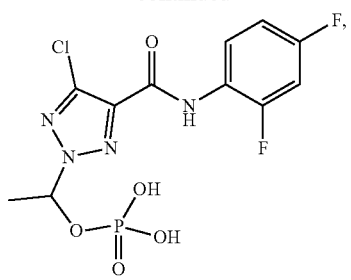
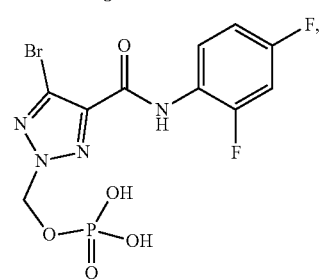
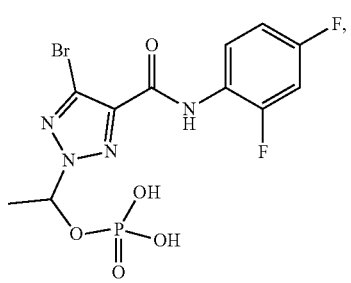
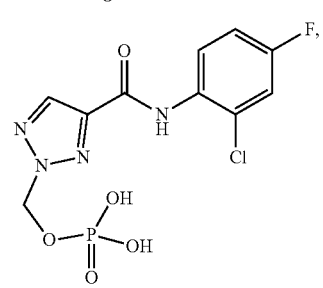
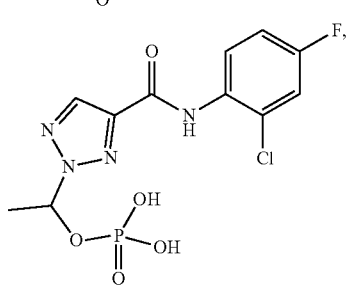
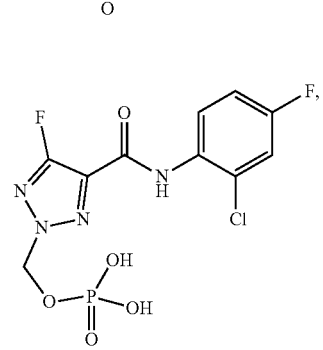

-continued
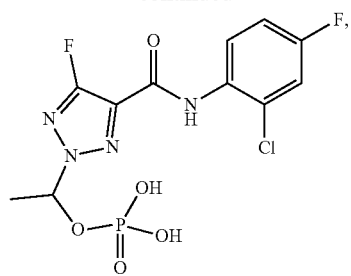
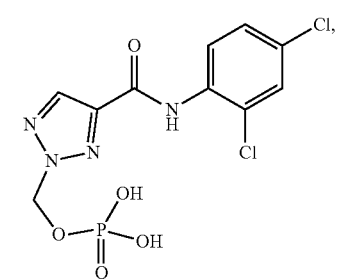
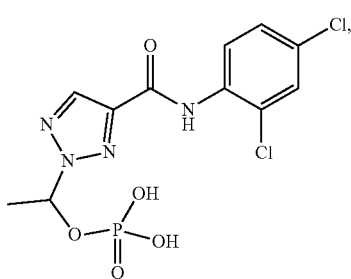
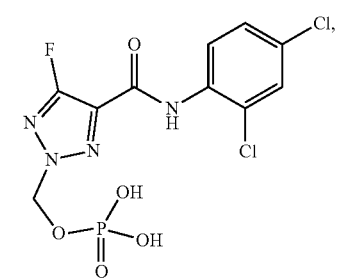
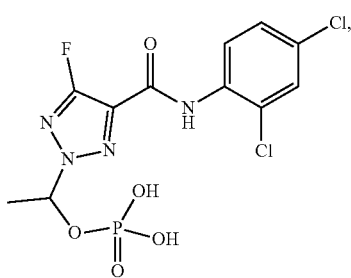
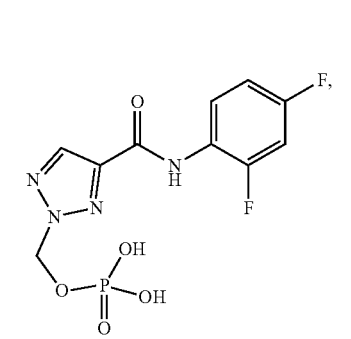
-continued
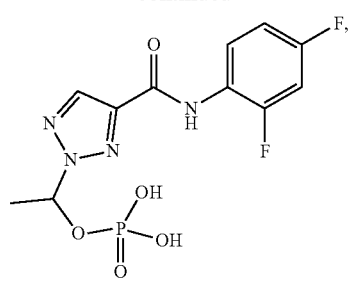
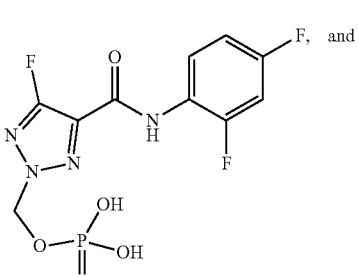
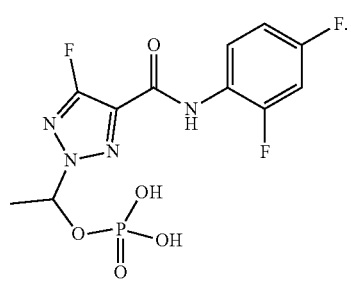
In some embodiments is a compound, or a pharmaceutically acceptable salt or solvate thereof, selected from:
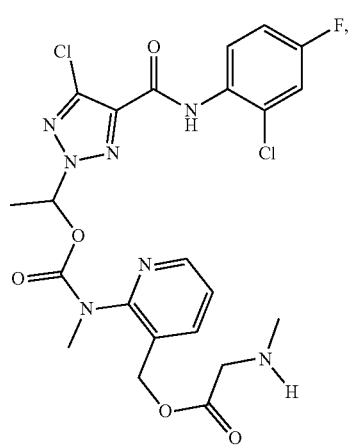

87
-continued
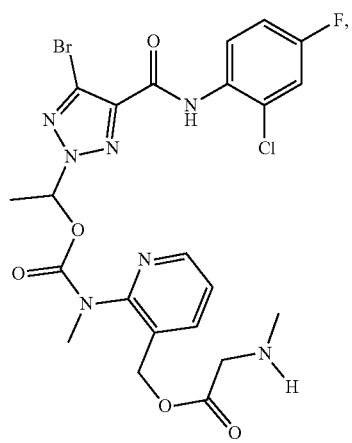
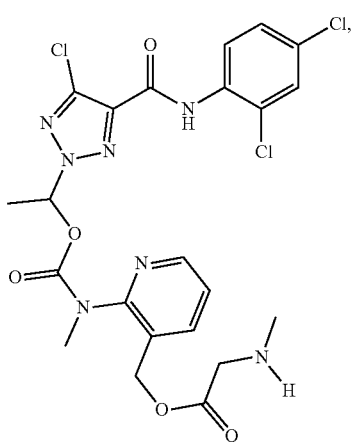
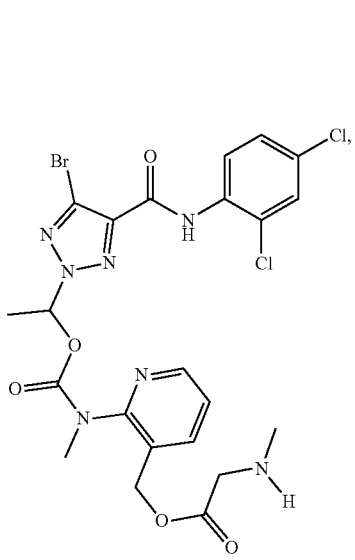
88
-continued
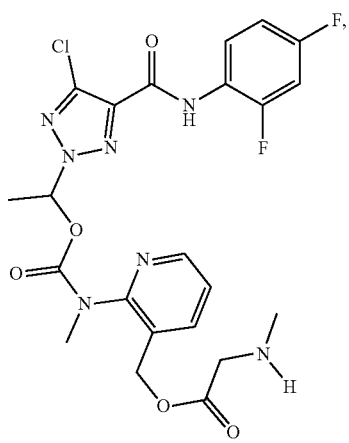
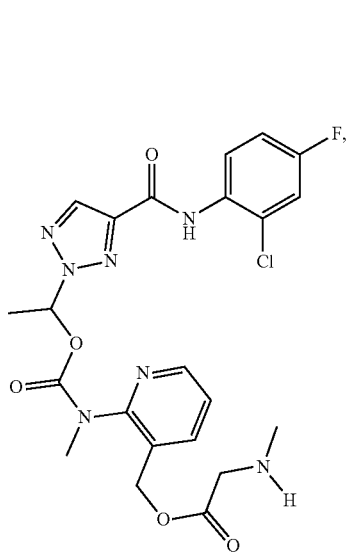
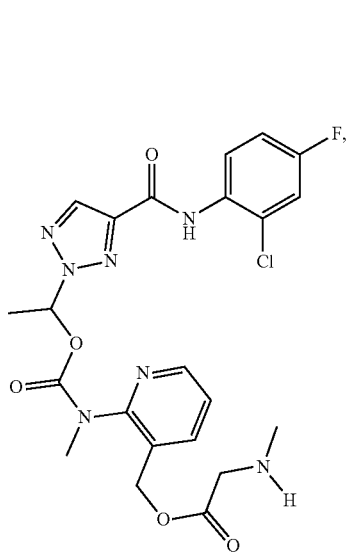

89
-continued
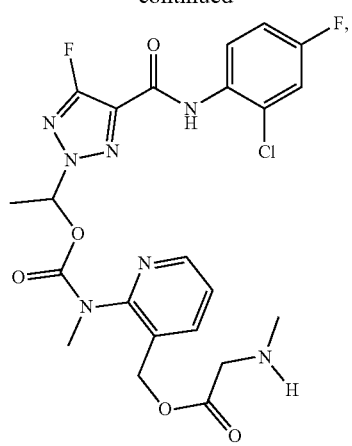
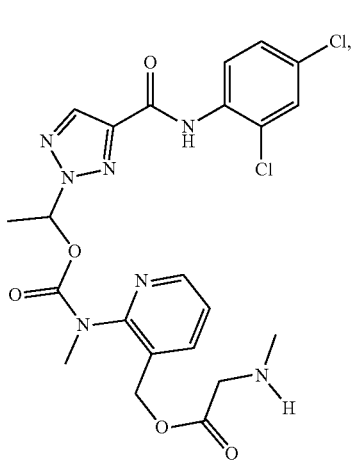
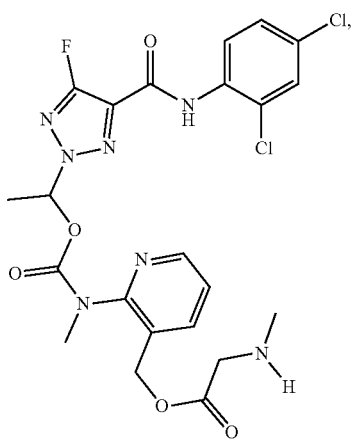
90
-continued
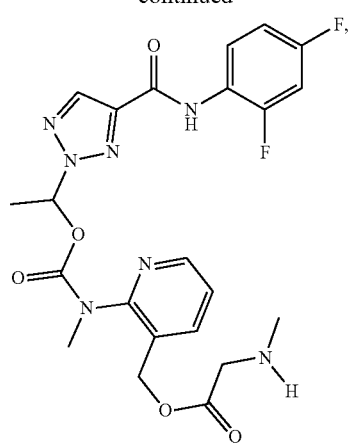
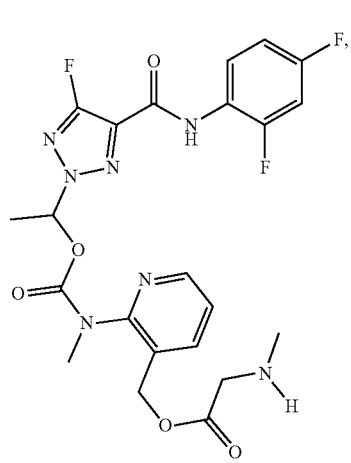
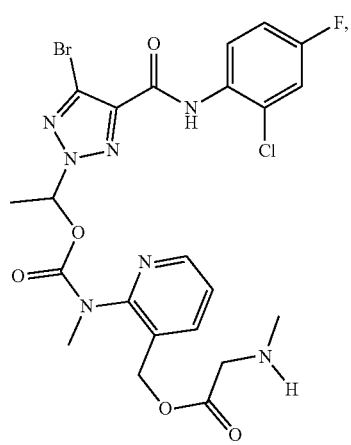

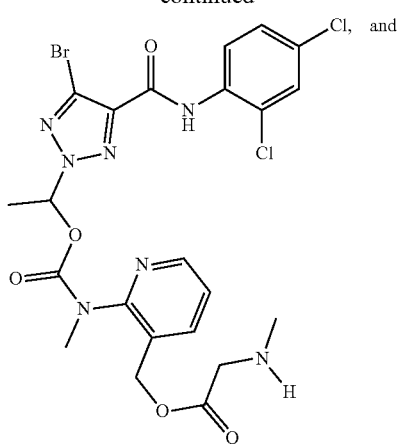
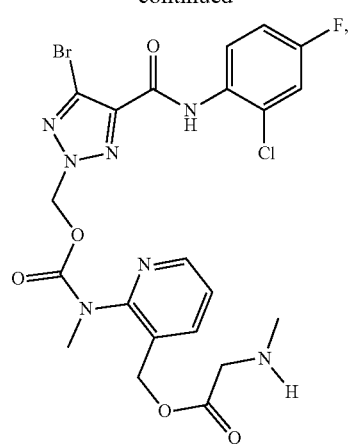
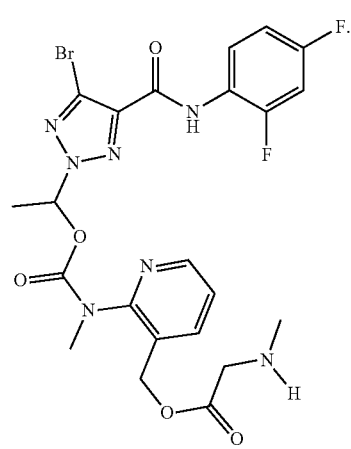
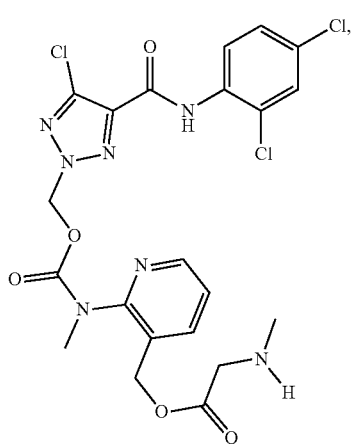
In some embodiments is a compound, or a pharmaceutically acceptable salt or solvate thereof, selected from:
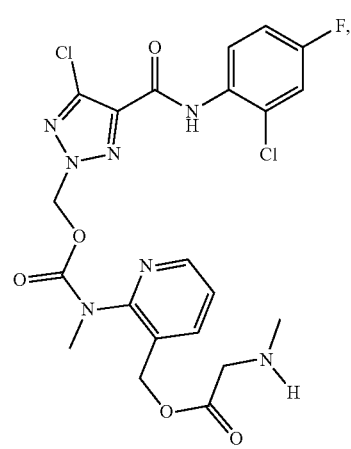
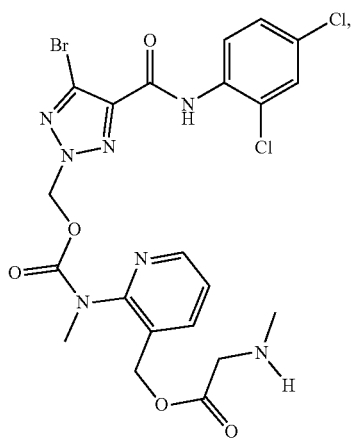

93
-continued
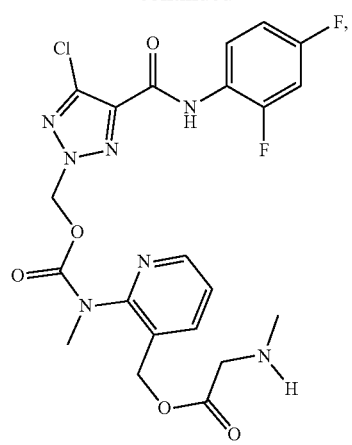
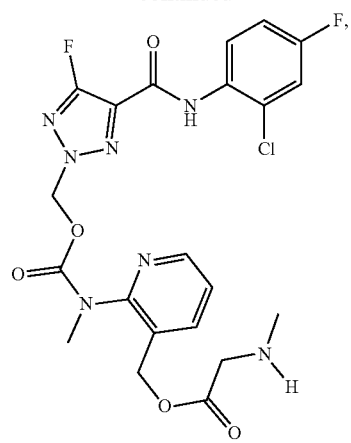
94
-continued
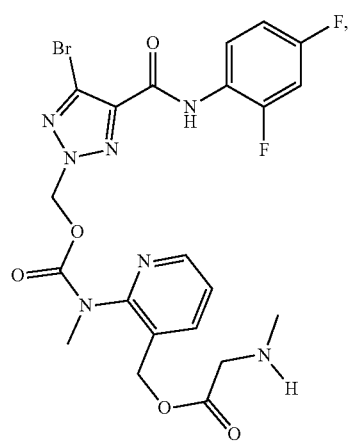
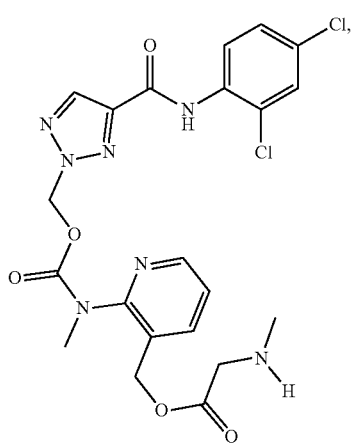
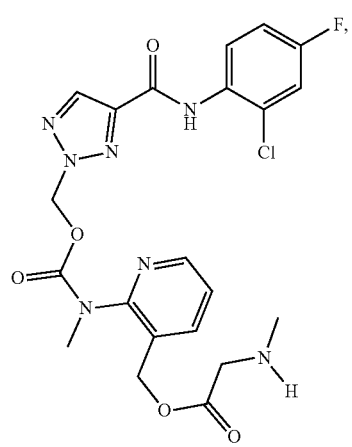
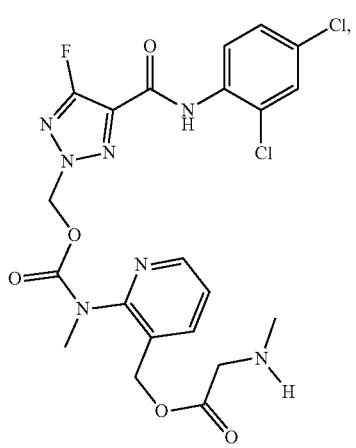

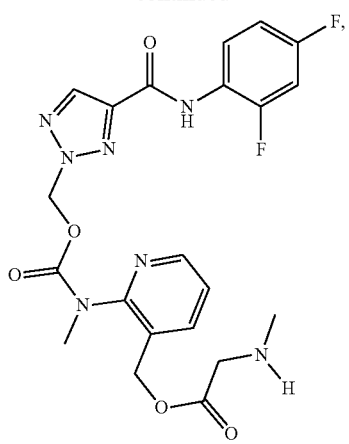
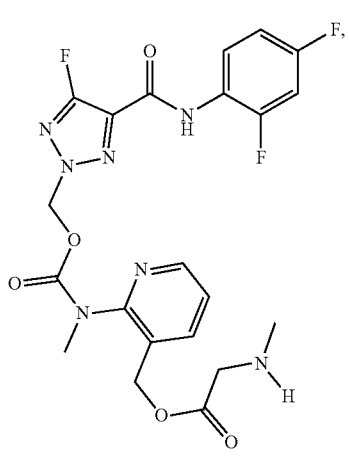
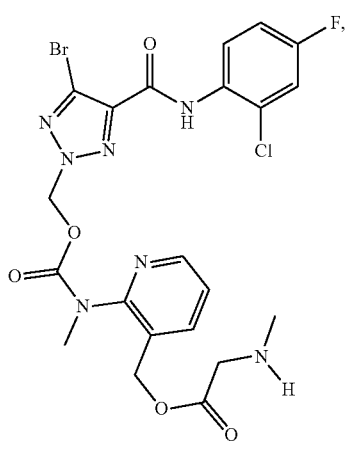
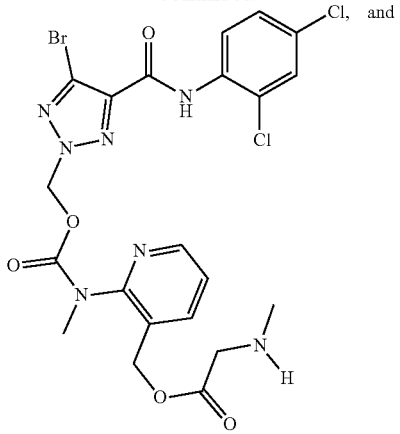
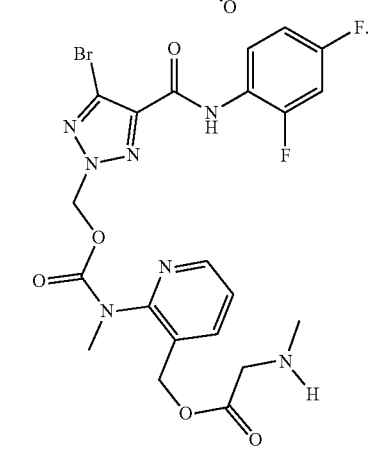
In some embodiments is a compound, or a pharmaceutically acceptable salt or solvate thereof, selected from:
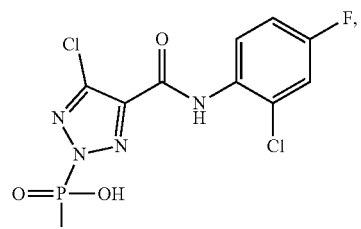
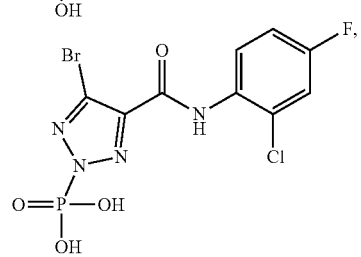
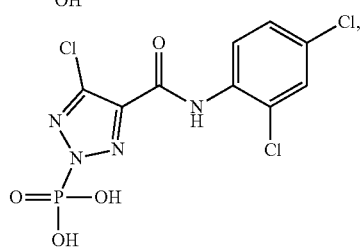

-continued
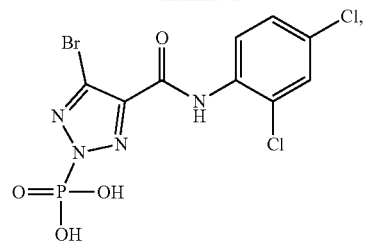
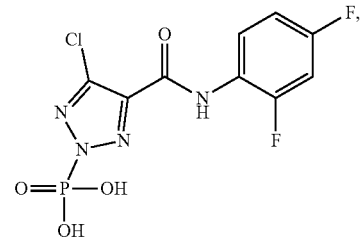
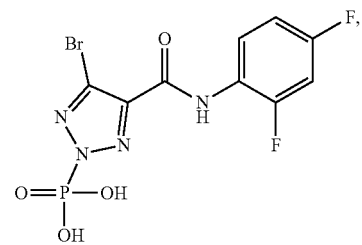
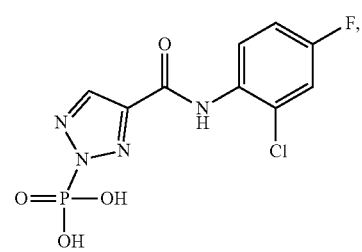
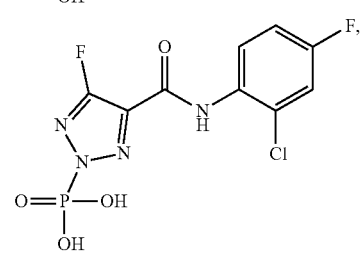
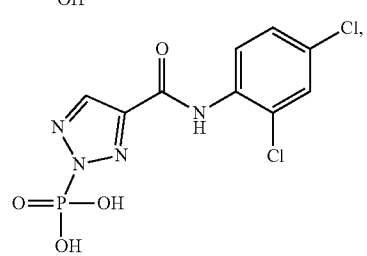
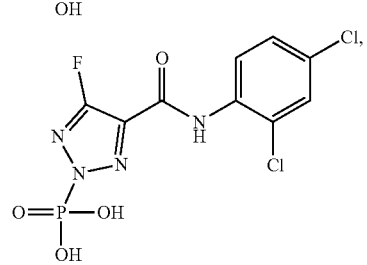
-continued
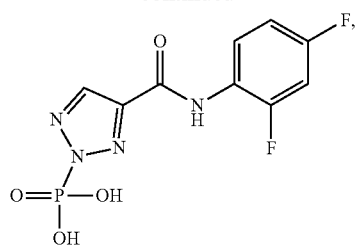
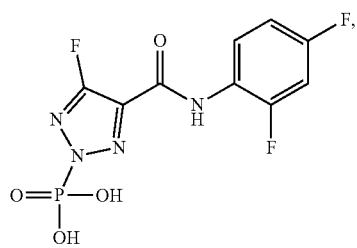
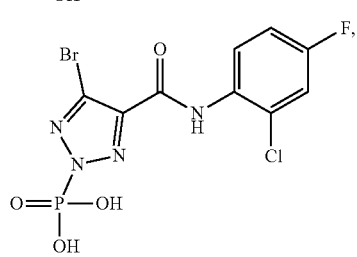
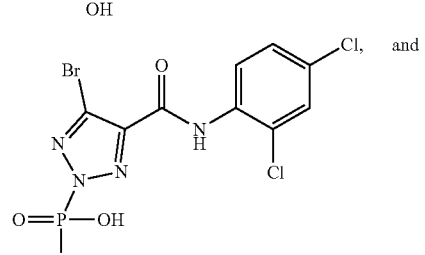
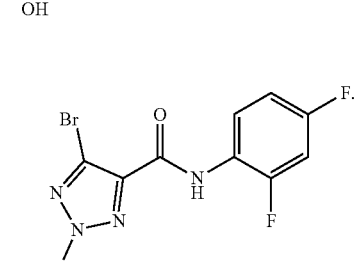
In some embodiments is a compound, or a pharmaceutically acceptable salt or solvate thereof, selected from:
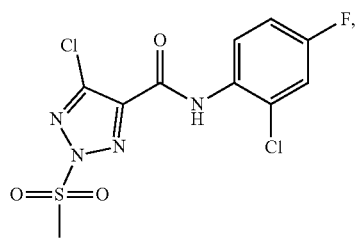

99
-continued
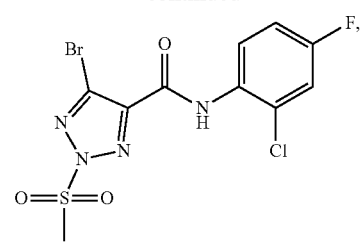
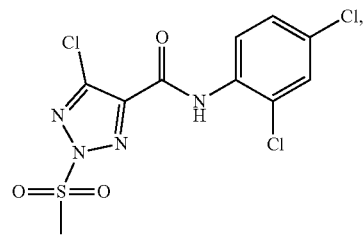
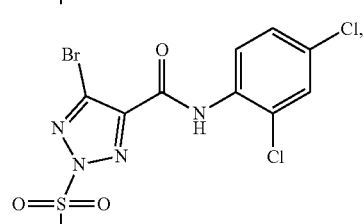
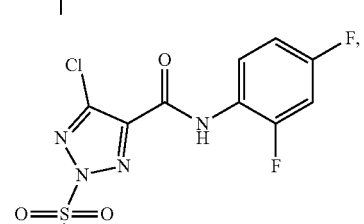
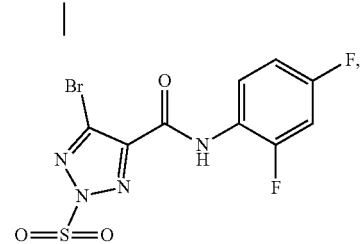
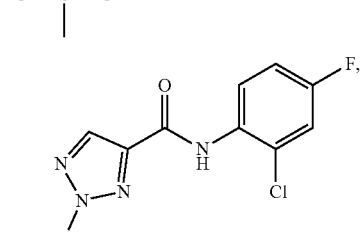
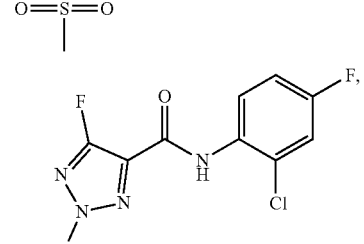
100
-continued
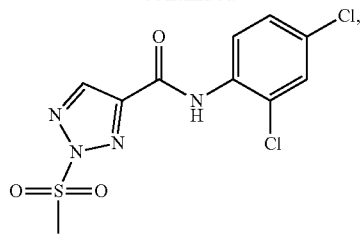
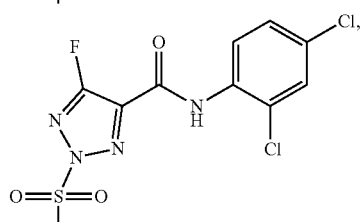
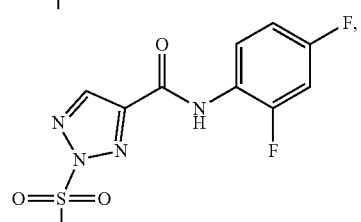
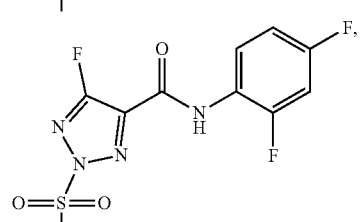
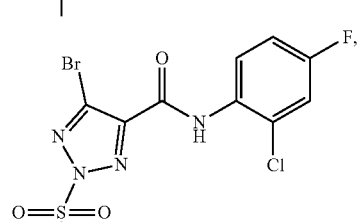
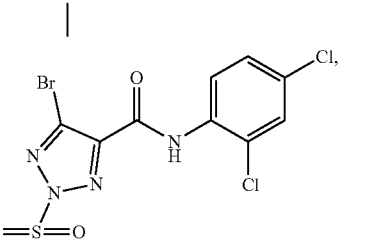
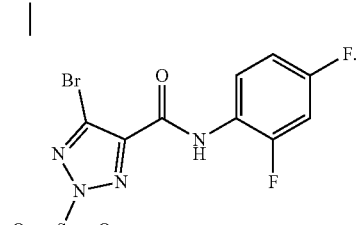
In some embodiments is a compound, or a pharmaceutically acceptable salt or solvate 101
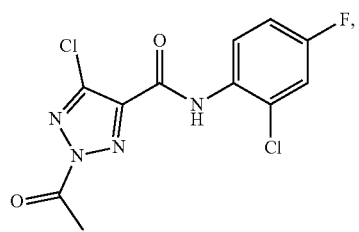
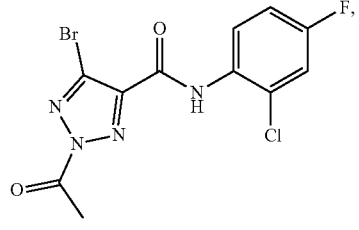
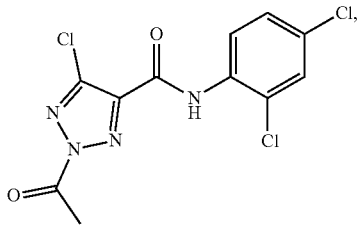
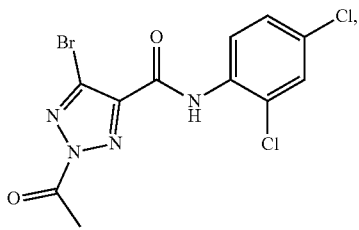
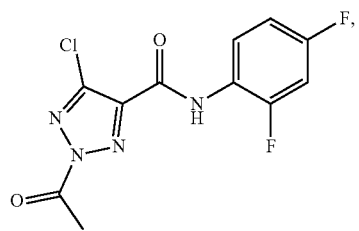
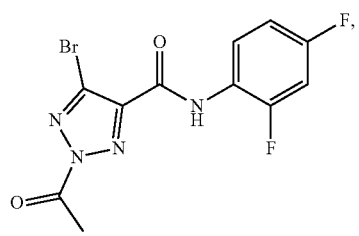
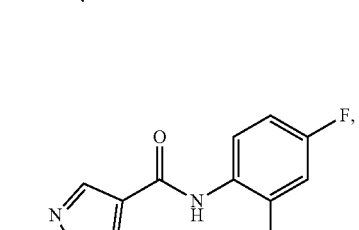
102
-continued
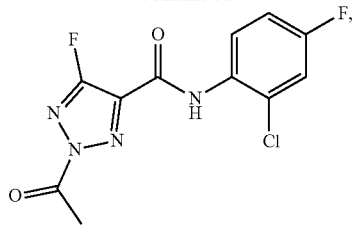
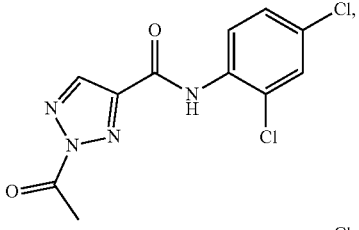
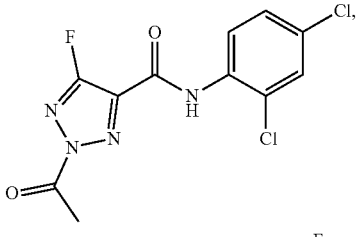
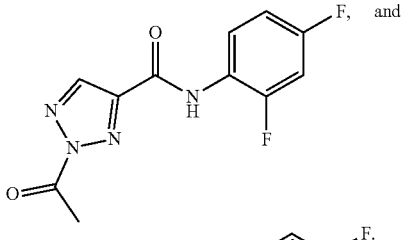
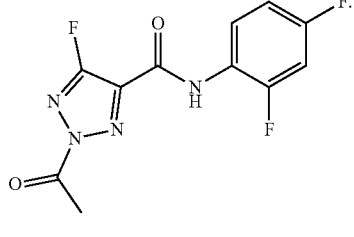
In some embodiments is a compound, or a pharmaceutically acceptable salt or solvate thereof, selected from:
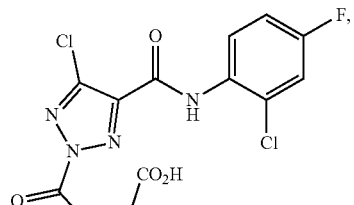
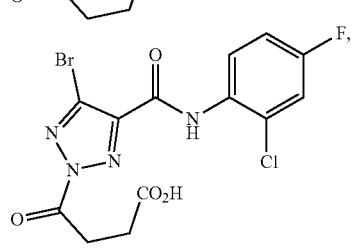

-continued

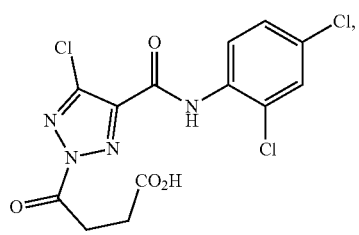
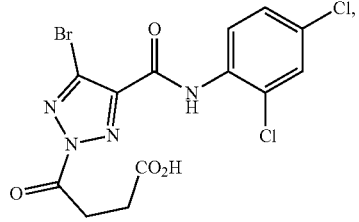
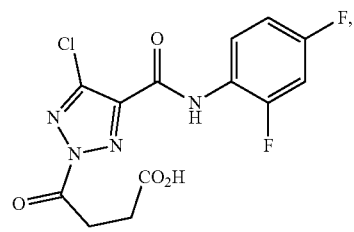
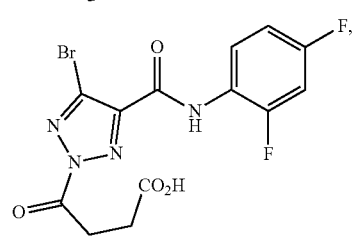
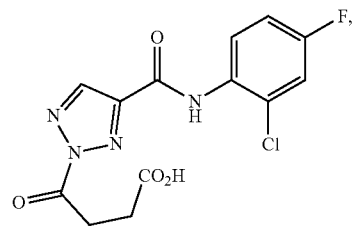
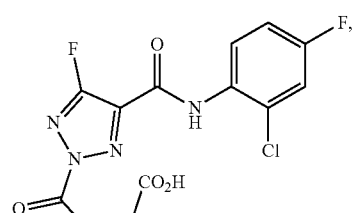
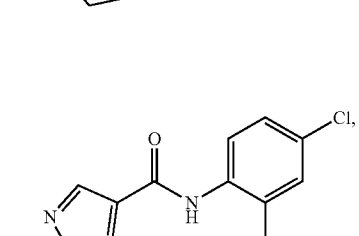

-continued

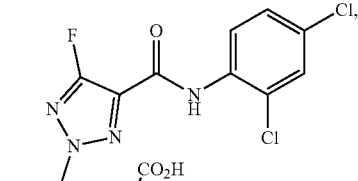
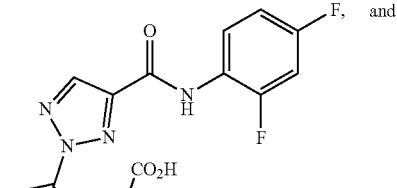
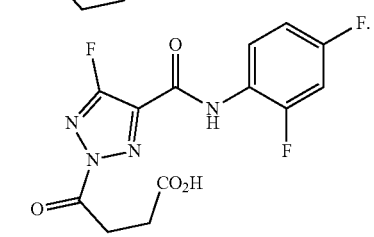

Preparation of the Compounds

The compounds used in the reactions described herein are made according to known organic synthesis techniques, starting from commercially available chemicals and/or from compounds described in the chemical literature. "Commercially available chemicals" are obtained from standard commercial sources including Acros Organics (Geel, Belgium), Aldrich Chemical (Milwaukee, Wis., including Sigma Chemical and Fluka), Apin Chemicals Ltd. (Milton Park, UK), Ark Pharm, Inc. (Libertyville, Ill.), Avocado Research (Lancashire, U.K.), BDH Inc. (Toronto, Canada), Bionet (Cornwall, U.K.), Chemservice Inc. (West Chester, Pa.), Combi-blocks (San Diego, Calif.), Crescent Chemical Co. (Hauppauge, N.Y.), eMolecules (San Diego, Calif.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Matrix Scientific, (Columbia, S.C.), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hanover, Germany), Ryan Scientific, Inc. (Mount Pleasant, S.C.), Spectrum Chemicals (Gardena, Calif.), Sundia Meditech, (Shanghai, China), TCI America (Portland, Oreg.), Trans World Chemicals, Inc. (Rockville, Md.), and WuXi (Shanghai, China).

Suitable reference books and treatises that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley- Interscience, New York, 1992. Additional suitable reference books and treatises that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants are also identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs are optionally prepared by custom chemical synthesis houses, where many of the standard chemical supply houses (e.g., those listed above) provide custom synthesis services. A reference for the preparation and selection of pharmaceutical salts of the compounds described herein is P. H. Stahl & C. G. Wermuth "Handbook of Pharmaceutical Salts", Verlag Helvetica Chimica Acta, Zurich, 2002.

In some embodiments, the compounds described herein are prepared by the general synthetic routes described below in Schemes 1-4.

Scheme 1

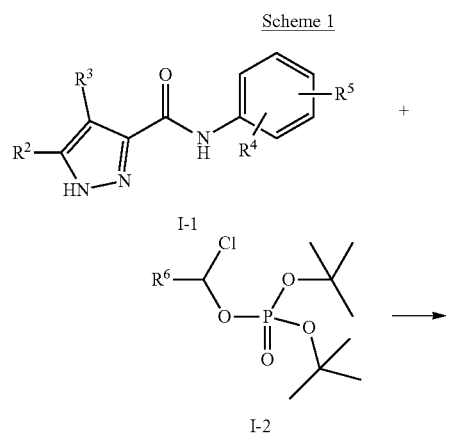

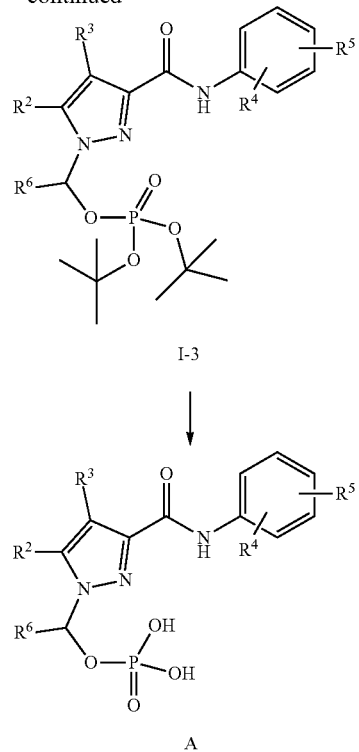

In Scheme 1, substituents $R^2$, $R^3$, $R^4$, $R^5$, and $R^6$ are as described herein.

In some embodiments, intermediate I-1 is reacted with a phosphonate I-2 with an appropriate base and solvent or solvent mixture at an appropriate time and at an appropriate temperature to provide intermediate I-3. In some embodiments, the base is an organic base such as triethylamine or diisopropylamine. In some embodiments, the base is cesium carbonate, sodium carbonate, or potassium carbonate. In some embodiments, the base is sodium hydride. In some embodiments, the base is sodium hydroxide. In some embodiments, the base is potassium hydroxide. In some embodiments the appropriate solvent is dichloromethane. In some embodiments, the appropriate time and appropriate temperature is about 2 to about 18 hours (overnight) hours at about room temperature.

In some embodiments, intermediate I-3 is hydrolyzed with an appropriate acid and solvent or solvent mixture at an appropriate time and at an appropriate temperature to provide compound A. In some embodiments, the acid is trifluoroacetic acid. In some embodiments, the acid is hydrochloric acid. In some embodiments the appropriate solvent is water/acetone. In some embodiments, the suitable temperature is about 0° C. to room temperature and the appropriate amount of time is about 18 hours (overnight).

Scheme 2

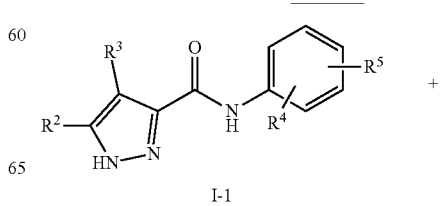

-continued

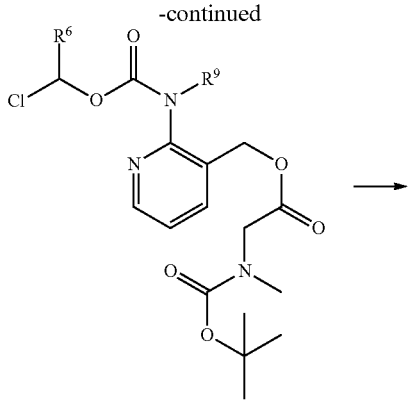

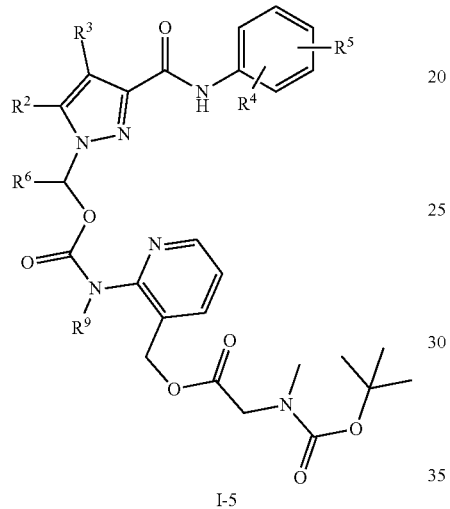

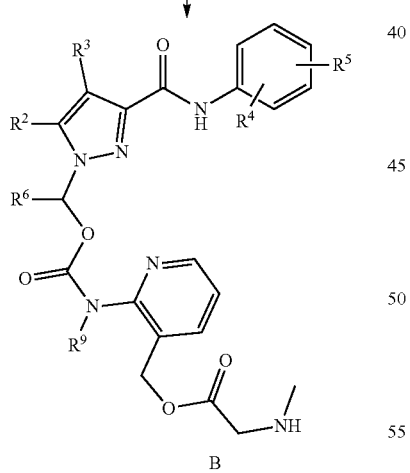

In some embodiments, the base is sodium hydroxide. In some embodiments, the base is potassium hydroxide. In some embodiments, the appropriate solvent is tetrahydrofuran. In some embodiments, the appropriate time and appropriate temperature is about 2 to about 18 hours (overnight) hours at about room temperature.

In some embodiments, intermediate I-5 is deprotected with an appropriate acid and solvent or solvent mixture at an appropriate time and at an appropriate temperature to provide compound B. In some embodiments, the acid is trifluoroacetic acid. In some embodiments, the acid is hydrochloric acid. In some embodiments, the appropriate solvent is ethyl acetate. In some embodiments, the suitable temperature is about 0° C. to room temperature and the appropriate amount of time is about 18 hours (overnight).

Scheme 3

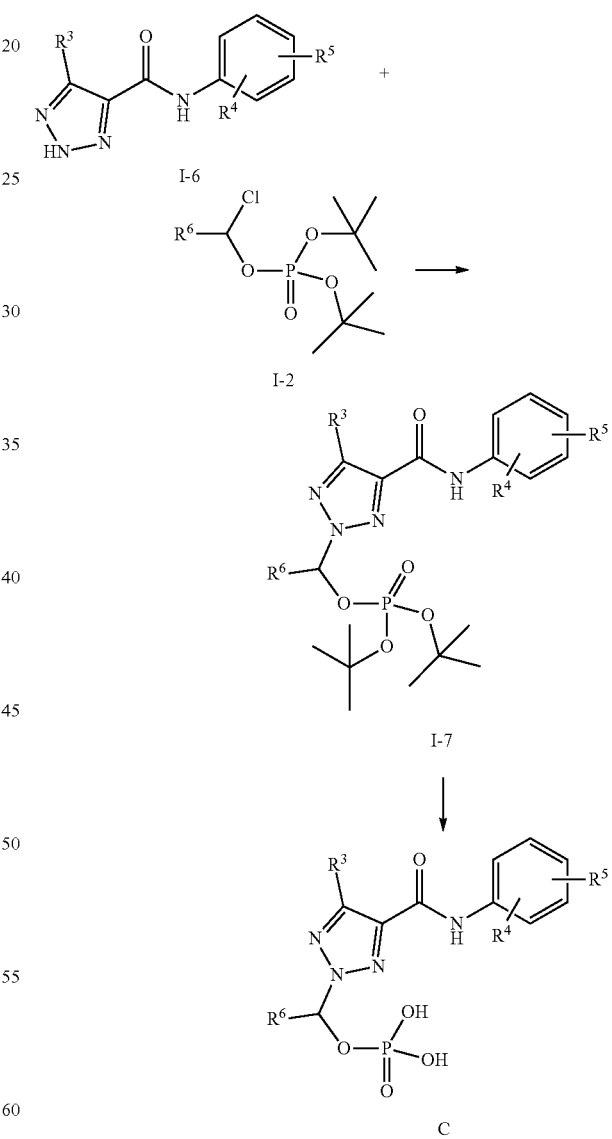

In Scheme 3, substituents $R^3$, $R^4$, $R^5$, and $R^6$ are as described herein.

In some embodiments, intermediate I-6 is reacted with a phosphonate I-2 with an appropriate base and solvent or solvent mixture at an appropriate time and at an appropriate In Scheme 2, substituents $R^2$, $R^3$, $R^4$, $R^5$, $R^6$, and $R^9$ are as described herein.

In some embodiments, intermediate I-1 is coupled with intermediate I-4 in the presence of an appropriate base and solvent or solvent mixture at an appropriate time and at an appropriate temperature to provide intermediate I-5. In some embodiments, the base is an organic base such as triethylamine or diisopropylamine. In some embodiments, the base is cesium carbonate, sodium carbonate, or potassium carbonate. In some embodiments, the base is sodium hydride.

temperature to provide intermediate I-7. In some embodiments, the base is an organic base such as triethylamine or diisopropylamine. In some embodiments, the base is cesium carbonate, sodium carbonate, or potassium carbonate. In some embodiments, the base is sodium hydride. In some embodiments, the base is sodium hydroxide. In some embodiments, the base is potassium hydroxide. In some embodiments the appropriate solvent is dichloromethane. In some embodiments, the appropriate time and appropriate temperature is about 2 to about 18 hours (overnight) hours at about room temperature.

In some embodiments, intermediate I-7 is hydrolyzed with an appropriate acid and solvent or solvent mixture at an appropriate time and at an appropriate temperature to provide compound C. In some embodiments, the acid is trifluoroacetic acid. In some embodiments, the acid is hydrochloric acid. In some embodiments the appropriate solvent is water/acetone. In some embodiments, the suitable temperature is about 0° C. to room temperature and the appropriate amount of time is about 18 hours (overnight).

Scheme 4

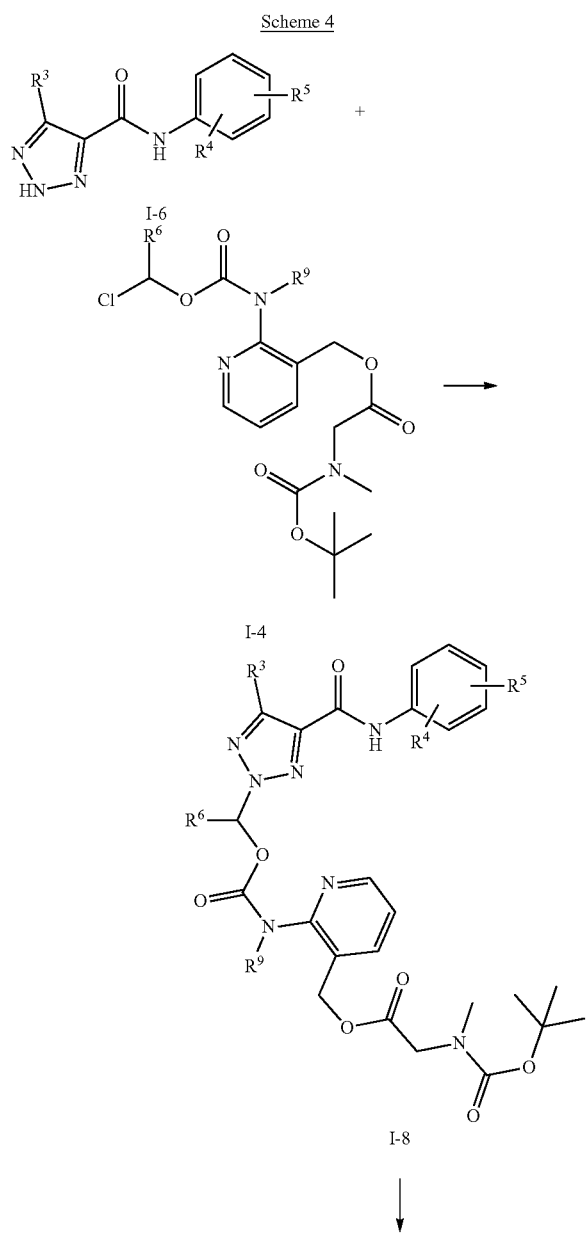

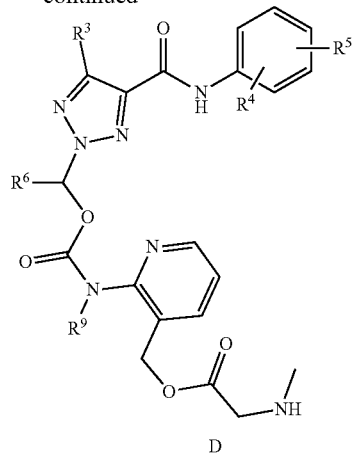

In Scheme 4, substituents $R^3$, $R^4$, $R^5$, $R^6$, and $R^9$ are as described herein.

In some embodiments, intermediate I-6 is coupled with intermediate I-4 in the presence of an appropriate base and solvent or solvent mixture at an appropriate time and at an appropriate temperature to provide intermediate I-8. In some embodiments, the base is an organic base such as triethylamine or diisopropylamine. In some embodiments, the base is cesium carbonate, sodium carbonate, or potassium carbonate. In some embodiments, the base is sodium hydride. In some embodiments, the base is sodium hydroxide. In some embodiments, the base is potassium hydroxide. In some embodiments, the appropriate solvent is tetrahydrofuran. In some embodiments, the appropriate time and appropriate temperature is about 2 to about 18 hours (overnight) hours at about room temperature.

In some embodiments, intermediate I-8 is deprotected with an appropriate acid and solvent or solvent mixture at an appropriate time and at an appropriate temperature to provide compound D. In some embodiments, the acid is trifluoroacetic acid. In some embodiments, the acid is hydrochloric acid. In some embodiments, the appropriate solvent is ethyl acetate. In some embodiments, the suitable temperature is about 0° C. to room temperature and the appropriate amount of time is about 18 hours (overnight).

Further Forms of Compounds Disclosed Herein

Isomers

Furthermore, in some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, compounds exist as tautomers. The compounds described herein include all possible tautomers within the formulas described herein. In some situations, the compounds described herein possess one or more chiral centers and each center exists in the R configuration or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion, are useful for the applications described herein. In some embodiments, the compounds described herein are prepared as optically pure enantiomers by chiral chromatographic resolution of the racemic mixture. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred (e.g., crystalline diastereomeric salts). In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that does not result in racemization.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that are incorporated into compounds described herein include isotopes of hydrogen, carbon, nitrogen, oxygen, phosphorous, sulfur, fluorine and chloride, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Compounds described herein, and the pharmaceutically acceptable salts, esters, solvate, hydrates, or derivatives thereof which contain the aforementioned isotopes and/or other isotopes of other atoms are within the scope of this invention. Certain isotopically-labeled compounds, for example those into which radioactive isotopes such as $^3$H and $^{14}$C are incorporated, are useful in drug and/or substrate tissue distribution assays. Tritiated, i.e., $^3$H and carbon-14, i.e., $^{14}$C, isotopes are particularly preferred for their ease of preparation and detectability. Further, substitution with heavy isotopes such as deuterium, i.e., $^2$H, produces certain therapeutic advantages resulting from greater metabolic stability, for example increased in vivo half-life or reduced dosage requirements. In some embodiments, the isotopically labeled compounds, pharmaceutically acceptable salt, ester, solvate, hydrate, or derivative thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds described herein, or by separately reacting a purified compound in its free form with a suitable acid or base, and isolating the salt thus formed.

Solvates

In some embodiments, the compounds described herein exist as solvates. In some embodiments, are methods of treating diseases by administering such solvates. Further described herein are methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein are conveniently prepared or formed during the processes described herein. By way of example only, hydrates of the compounds described herein are conveniently prepared by recrystallization from an aqueous/organic solvent mixture, using organic solvents including, but not limited to, dioxane, tetrahydrofuran, or methanol. In addition, the compounds provided herein exist in unsolvated as well as solvated forms. In general, the solvated forms are considered equivalent to the unsolvated forms for the purposes of the compounds and methods provided herein.

Pharmaceutical Compositions and Methods of Administration

In certain embodiments, the compound of Formula (I), (Ia), (Ib), (II), (IIa), (IIb), (III), (IIIa), or (IIIb) as described herein is administered as a pure chemical. In some embodiments, the compound of Formula (I), (Ia), (Ib), (II), (IIa), (IIb), (III), (IIIa), or (IIIb) described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in Remington: The Science and Practice of Pharmacy (Gennaro, 21st Ed. Mack Pub. Co., Easton, Pa. (2005)).

Accordingly, provided herein is a pharmaceutical composition comprising at least one compound of Formula (I), (Ia), (Ib), (II), (IIa), (IIb), (III), (IIIa), or (IIIb) described herein, or a pharmaceutically acceptable salt or solvate thereof, together with one or more pharmaceutically acceptable carriers. The carrier(s) (or excipient(s)) is acceptable or suitable if the carrier is compatible with the other ingredients of the composition and not deleterious to the recipient (i.e., the subject) of the composition.

One embodiment provides a pharmaceutical composition comprising a pharmaceutically acceptable excipient and a compound of Formula (I), or a pharmaceutically acceptable salt thereof.

One embodiment provides a pharmaceutical composition comprising a pharmaceutically acceptable excipient and a compound of Formula (Ia), or a pharmaceutically acceptable salt thereof.

One embodiment provides a pharmaceutical composition comprising a pharmaceutically acceptable excipient and a compound of Formula (Ib), or a pharmaceutically acceptable salt thereof.

One embodiment provides a pharmaceutical composition comprising a pharmaceutically acceptable excipient and a compound of Formula (II), or a pharmaceutically acceptable salt thereof.

One embodiment provides a pharmaceutical composition comprising a pharmaceutically acceptable excipient and a compound of Formula (IIa), or a pharmaceutically acceptable salt thereof.

One embodiment provides a pharmaceutical composition comprising a pharmaceutically acceptable excipient and a compound of Formula (IIb), or a pharmaceutically acceptable salt thereof.

One embodiment provides a pharmaceutical composition comprising a pharmaceutically acceptable excipient and a compound of Formula (III), or a pharmaceutically acceptable salt thereof.

One embodiment provides a pharmaceutical composition comprising a pharmaceutically acceptable excipient and a compound of Formula (IIIa), or a pharmaceutically acceptable salt thereof.

One embodiment provides a pharmaceutical composition comprising a pharmaceutically acceptable excipient and a compound of Formula (IIIb), or a pharmaceutically acceptable salt thereof.

Another embodiment provides a pharmaceutical composition consisting essentially of a pharmaceutically acceptable excipient and a compound of Formula (I), or a pharmaceutically acceptable salt thereof. Another embodiment provides a pharmaceutical composition consisting essentially of a pharmaceutically acceptable excipient and a compound of Formula (Ia), or a pharmaceutically acceptable salt thereof. Another embodiment provides a pharmaceutical composition consisting essentially of a pharmaceutically acceptable excipient and a compound of Formula (Ib), or a pharmaceutically acceptable salt thereof. Another embodiment provides a pharmaceutical composition consisting essentially of a pharmaceutically acceptable excipient and a compound of Formula (II), or a pharmaceutically acceptable salt thereof. Another embodiment provides a pharmaceutical composition consisting essentially of a pharmaceutically acceptable excipient and a compound of Formula (IIa), or a pharmaceutically acceptable salt thereof. Another embodiment provides a pharmaceutical composition consisting essentially of a pharmaceutically acceptable excipient and a compound of Formula (IIb), or a pharmaceutically acceptable salt thereof. Another embodiment provides a pharmaceutical composition consisting essentially of a pharmaceutically acceptable excipient and a compound of Formula (III), or a pharmaceutically acceptable salt thereof. Another embodiment provides a pharmaceutical composition consisting essentially of a pharmaceutically acceptable excipient and a compound of Formula (IIIa), or a pharmaceutically acceptable salt thereof. Another embodiment provides a pharmaceutical composition consisting essentially of a pharmaceutically acceptable excipient and a compound of Formula (IIIb), or a pharmaceutically acceptable salt thereof.

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that are used pharmaceutically. Proper formulation is dependent upon the route of administration chosen. A summary of pharmaceutical compositions described herein is found, for example, in Remington: The Science and Practice of Pharmacy, Nineteenth Ed. (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

In some embodiments, the compounds described herein are administered either alone or in combination with pharmaceutically acceptable carriers, excipients or diluents, in a pharmaceutical composition. Administration of the compounds and compositions described herein can be effected by any method that enables delivery of the compounds to the site of action. These methods include, though are not limited to, delivery via enteral routes (including oral, gastric or duodenal feeding tube, rectal suppository, and rectal enema), parenteral routes (injection or infusion, including intraarterial, intracardiac, intradermal, intraduodenal, intramedullary, intramuscular, intraosseous, intraperitoneal, intrathecal, intravascular, intravenous, intravitreal, epidural, and subcutaneous), inhalational, transdermal, transmucosal, sublingual, buccal, and topical (including epicutaneous, dermal, enema, eye drops, ear drops, intranasal, vaginal) administration, although the most suitable route may depend upon for example, the condition and disorder of the recipient. By way of example only, compounds described herein can be administered locally to the area in need of treatment, by local infusion during surgery, topical application such as creams or ointments, injection, catheter, or implant. The administration can also be by direct injection at the site of a diseased tissue or organ.

In some embodiments, pharmaceutical compositions suitable for oral administration are presented as discrete units such as capsules, cachets, or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. In some embodiments, the active ingredient is presented as a bolus, electuary, or paste.

Pharmaceutical compositions which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. In some embodiments, the tablets are coated or scored and are formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In some embodiments, stabilizers are added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or Dragee coatings for identification or to characterize different combinations of active compound doses.

In some embodiments, pharmaceutical compositions are formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The compositions may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Pharmaceutical compositions for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical compositions may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

Pharmaceutical compositions may be administered topically, that is by non-systemic administration. This includes the application of a compound of the present invention externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Pharmaceutical compositions suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient may comprise, for topical administration, from 0.001% to 10% w/w, for instance from 1% to 2% by weight of the formulation.

In some embodiments, pharmaceutical compositions are formulated for intranasal administration. Potential excipients for intranasal formulations include, for example, U.S. Pat. Nos. 4,476,116, 5,116,817 and 6,391,452. Formulations solutions in saline, employing benzyl alcohol or other suitable preservatives, fluorocarbons, and/or other solubilizing or dispersing agents. See, for example, Ansel, H. C. et al., Pharmaceutical Dosage Forms and Drug Delivery Systems, Sixth Ed. (1995). Preferably these compositions and formulations are prepared with suitable nontoxic pharmaceutically acceptable ingredients. The choice of suitable carriers is highly dependent upon the exact nature of the nasal dosage form desired, e.g., solutions, suspensions, ointments, or gels. Nasal dosage forms generally contain large amounts of water in addition to the active ingredient. Minor amounts of other ingredients such as pH adjusters, emulsifiers or dispersing agents, preservatives, surfactants, gelling agents, or buffering and other stabilizing and solubilizing agents may also be present. Preferably, the nasal dosage form should be isotonic with nasal secretions.

Pharmaceutical compositions for administration by inhalation are conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, pharmaceutical preparations may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

It should be understood that in addition to the ingredients particularly mentioned above, the compounds and compositions described herein may include other agents conventional in the art having regard to the type of formulation in question, for example those suitable for oral administration may include flavoring agents.

Generally, an agent, such as a compound of Formula (I), (Ia), (Ib), (II), (IIa), (IIb), (III), (IIIa), or (IIIb), is administered in an amount effective for amelioration of, or prevention of the development of symptoms of, the disease or disorder (i.e., a therapeutically effective amount). Thus, a therapeutically effective amount can be an amount that is capable of at least partially preventing or reversing a disease or disorder. The dose required to obtain an effective amount may vary depending on the agent, formulation, disease or disorder, and individual to whom the agent is administered.

Determination of effective amounts may also involve in vitro assays in which varying doses of agent are administered to cells in culture and the concentration of agent effective for ameliorating some or all symptoms is determined in order to calculate the concentration required in vivo. Effective amounts may also be based in in vivo animal studies.

An agent can be administered prior to, concurrently with, and subsequent to the appearance of symptoms of a disease or disorder. In some embodiments, an agent is administered to a subject with a family history of the disease or disorder, or who has a phenotype that may indicate a predisposition to a disease or disorder, or who has a genotype which predisposes the subject to the disease or disorder.

Oral doses typically range from about 1.0 mg to about 1000 mg, one to four times, or more, per day.

Methods

In one embodiment, the compounds described herein, or a pharmaceutically acceptable salt thereof, are used in the preparation of medicaments for the treatment of diseases or conditions in a mammal that would benefit from administration of an ALOX-15 inhibitor. Methods for treating any of the diseases or conditions described herein in a mammal in need of such treatment, involves administration of pharmaceutical compositions that include at least one compound described herein or a pharmaceutically acceptable salt, active metabolite, or pharmaceutically acceptable solvate thereof, in therapeutically effective amounts to said mammal.

In some embodiments disclosed herein, are methods of administering an ALOX-15 inhibitor in combination with an additional therapeutic agent.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation and/or dose ranging clinical trial.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in patients, effective amounts for this use will depend on the severity and course of the disease, disorder or condition, previous therapy, the patient's health status and response to the drugs, and the judgment of the treating physician. In one aspect, prophylactic treatments include administering to a mammal, who previously experienced at least one symptom of the disease being treated and is currently in remission, a pharmaceutical composition comprising a compound described herein, or a pharmaceutically acceptable salt thereof, in order to prevent a return of the symptoms of the disease or condition.

In some embodiments is a method of treating a disease in a patient that would benefit from treatment with an ALOX-15 inhibitor, comprising administering to the patient a therapeutically effective amount of a compound of Formula (I), (Ia), (Ib), (II), (IIa), (IIb), (III), (IIIa), or (IIIb), or a pharmaceutically acceptable salt or solvate thereof.

In some embodiments is a method of treating an eosinophilic airway disease in a mammal in need thereof, comprising administering to the patient a therapeutically effective amount of a compound of Formula (I), (Ia), (Ib), (II), (IIa), (IIb), (III), (IIIa), or (IIIb) described herein, or a pharmaceutically acceptable salt or solvate thereof. In some embodiments is a method of treating an eosinophilic airway disease in a mammal in need thereof, comprising administering to the patient a therapeutically effective amount of a compound of Formula (I), (Ia), (Ib), (II), (IIa), (IIb), (III), (IIIa), or (IIIb) described herein, or a pharmaceutically acceptable salt or solvate thereof, wherein the eosinophilic airway disease is asthma, chronic rhinosinusitis, nasal polyposis or allergic rhinitis. In some embodiments is a method of treating an eosinophilic airway disease in a mammal in need thereof, comprising administering to the patient a therapeutically effective amount of a compound of Formula (I), (Ia), (Ib), (II), (IIa), (IIb), (III), (IIIa), or (IIIb) described herein, or a pharmaceutically acceptable salt or solvate thereof, wherein the eosinophilic airway disease is asthma. In some embodiments is a method of treating an eosinophilic airway disease in a mammal in need thereof, comprising administering to the patient a therapeutically effective amount of a compound of Formula (I), (Ia), (Ib), (II), (IIa), (IIb), (III), (IIIa), or (IIIb) described herein, or a pharmaceutically acceptable salt or solvate thereof, wherein the eosinophilic airway disease is chronic rhinosinusitis. In some embodiments is a method of treating an eosinophilic airway disease in a mammal in need thereof, comprising administering to the patient a therapeutically effective amount of a compound of Formula (I), (Ia), (Ib), (II), (IIa), (IIb), (III), (IIIa), or (IIIb) described herein, or a pharmaceutically acceptable salt or solvate thereof, wherein the eosinophilic airway disease is nasal polyposis. In some embodiments is a method of treating an eosinophilic airway disease in a mammal in need thereof, comprising administering to the patient a therapeutically effective amount of a compound of Formula (I), (Ia), (Ib), (II), (IIa), (IIb), (III), (IIIa), or (IIIb) described herein, or a pharmaceutically acceptable salt or solvate thereof, wherein the eosinophilic airway disease is allergic rhinitis.

In some embodiments is a method of treating an eosinophilic disease of the gastro-intestinal tract in a mammal in need thereof, comprising administering to the patient a therapeutically effective amount of a compound of Formula (I), (Ia), (Ib), (II), (IIa), (IIb), (III), (IIIa), or (IIIb) described herein, or a pharmaceutically acceptable salt or solvate thereof. In some embodiments is a method of treating eosinophilic disease of the gastro-intestinal tract in a mammal in need thereof, comprising administering to the patient a therapeutically effective amount of a compound of Formula (I), (Ia), (Ib), (II), (IIa), (IIb), (III), (IIIa), or (IIIb) described herein, or a pharmaceutically acceptable salt or solvate thereof, wherein the eosinophilic disease of the gastro-intestinal tract is eosinophilic esophagitis or eosinophilic gastritis. In some embodiments is a method of treating an eosinophilic disease of the gastro-intestinal tract in a mammal in need thereof, comprising administering to the patient a therapeutically effective amount of a compound of Formula (I), (Ia), (Ib), (II), (IIa), (IIb), (III), (IIIa), or (IIIb) described herein, or a pharmaceutically acceptable salt or solvate thereof, wherein the eosinophilic disease of the gastro-intestinal tract is eosinophilic esophagitis. In some embodiments is a method of treating an eosinophilic disease of the gastro-intestinal tract in a mammal in need thereof, comprising administering to the patient a therapeutically effective amount of a compound of Formula (I), (Ia), (Ib), (II), (IIa), (IIb), (III), (IIIa), or (IIIb) described herein, or a pharmaceutically acceptable salt or solvate thereof, wherein the eosinophilic disease of the gastro-intestinal tract is eosinophilic gastritis.

Disclosed compounds are administered to patients (mammals) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors, with the appropriate dosage ultimately being at the discretion of the attendant physician. For treating clinical conditions and diseases noted above, a contemplated compound disclosed herein is administered orally, subcutaneously, topically, parenterally, by inhalation spray, or rectally in dosage unit formulations containing conventional non-toxic pharmaceutically acceptable carriers, adjuvants, and vehicles. Parenteral administration includes subcutaneous injections, intravenous or intramuscular injections or infusion techniques.

Also contemplated herein are combination therapies, for example, co-administering a disclosed compound and an additional active agent, as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually weeks, months, or years depending upon the combination selected). Combination therapy is intended to embrace administration of multiple therapeutic agents in a sequential manner, that is, wherein each therapeutic agent is administered at a different time, as well as administration of these therapeutic agents, or at least two of the therapeutic agents, in a substantially simultaneous manner.

Substantially simultaneous administration is accomplished, for example, by administering to the subject a single formulation or composition, (e.g., a tablet or capsule having a fixed ratio of each therapeutic agent or in multiple, single formulations (e.g., capsules) for each of the therapeutic agents. Sequential or substantially simultaneous administration of each therapeutic agent is effected by any appropriate route including, but not limited to, oral routes, intravenous routes, intramuscular routes, and direct absorption through mucous membrane tissues. The therapeutic agents are administered by the same route or by different routes. For example, a first therapeutic agent of the combination selected is administered by intravenous injection while the other therapeutic agents of the combination are administered orally. Alternatively, for example, all therapeutic agents are administered orally or all therapeutic agents are administered by intravenous injection.

Combination therapy also embraces the administration of the therapeutic agents as described above in further combination with other biologically active ingredients and non-drug therapies. Where the combination therapy further comprises a non-drug treatment, the non-drug treatment is conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The components of the combination are administered to a patient simultaneously or sequentially. It will be appreciated that the components are present in the same pharmaceutically acceptable carrier and, therefore, are administered simultaneously. Alternatively, the active ingredients are present in separate pharmaceutical carriers, such as conventional oral dosage forms, that are administered either simultaneously or sequentially.

Kits/Articles of Manufacture

For use in the therapeutic applications described herein, kits and articles of manufacture are also described herein. Such kits can include a carrier, package, or container that is compartmentalized to receive one or more containers such as vials, tubes, and the like, each of the container(s) including one of the separate elements to be used in a method described herein. Suitable containers include, for example, bottles, vials, syringes, and test tubes. The containers can be formed from a variety of materials such as glass or plastic.

The articles of manufacture provided herein contain packaging materials. Packaging materials for use in packaging pharmaceutical products include, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disease, disorder, or condition that would benefit by an ALOX-15 inhibitor.

For example, the container(s) can include one or more compounds described herein, optionally in a composition or in combination with another agent as disclosed herein. The container(s) optionally have a sterile access port (for example the container can be an intravenous solution bag or a vial having a stopper pierceable by a hypodermic injection needle). Such kits optionally comprising a compound with an identifying description or label or instructions relating to its use in the methods described herein.

A kit will typically include one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included.

A label can be on or associated with the container. A label can be on a container when letters, numbers or other characters forming the label are attached, molded or etched into the container itself, a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein.

In certain embodiments, the pharmaceutical compositions can be presented in a pack or dispenser device which can contain one or more unit dosage forms containing a compound provided herein. The pack can for example contain metal or plastic foil, such as a blister pack. The pack or dispenser device can be accompanied by instructions for administration. The pack or dispenser can also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, can be the labeling approved by the U.S. Food and Drug Administration for prescription drugs, or the approved product insert. Compositions containing a compound provided herein formulated in a compatible pharmaceutical carrier can also be prepared, placed in an appropriate container, and labeled for treatment of an indicated condition.

EXAMPLES

Example 1: Synthesis of 4,5-dichloro-N-(2-chloro-4-fluorophenyl)-1H-pyrazole-3-carboxamide (3)

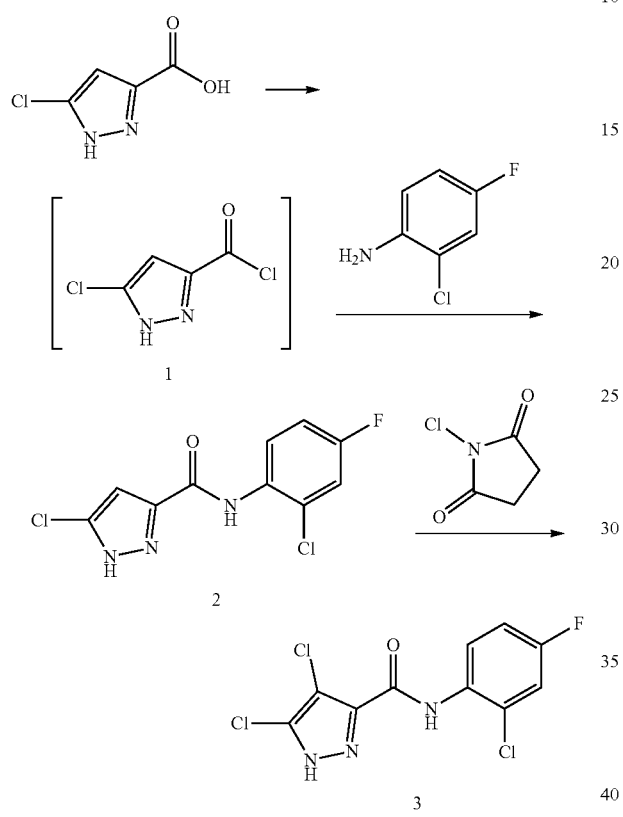

Example 2: Synthesis of (4,5-dichloro-3-((2-chloro-4-fluorophenyl)carbamoyl)-1H-pyrazol-1-yl)methyl dihydrogen phosphate (5)

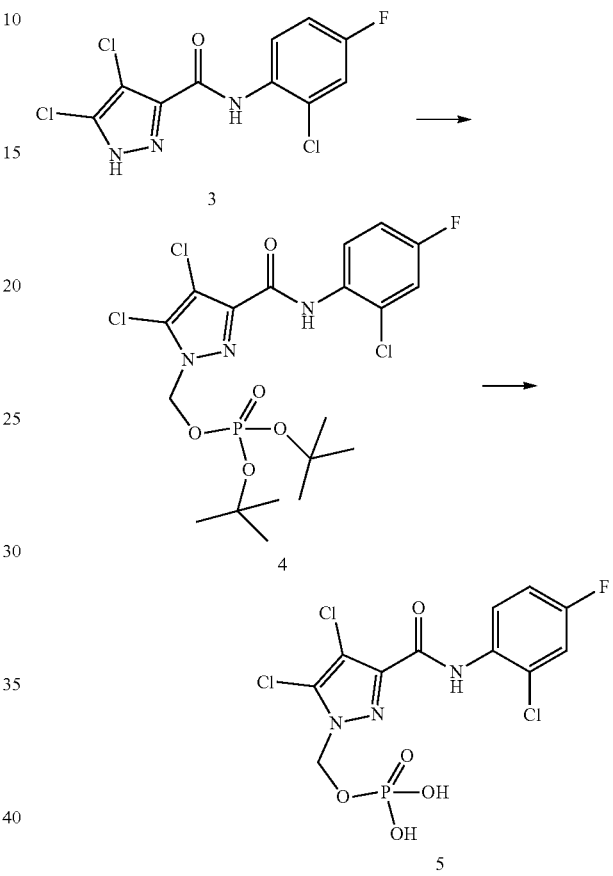

5-chloro-1H-pyrazole-3-carboxylic acid (5 g) in a 250 mL round-bottom flask was dissolved in thionyl chloride (50 mL) at 0° C. The reaction mixture was heated at 90° C. for 3 hours. The reaction mixture was cooled and the excess thionyl chloride was removed by rotary evaporation. The resulting acid chloride (compound 1) was dissolved in methylene chloride (100 mL). To this solution was added 2-chloro-4-fluoroaniline (7.45 g, 1.5 mole eq) in methylene chloride (100 mL) followed by triethyl amine (10.35 g, 3 mole eq). The reaction mixture was stirred at room temperature for 1 hour. The reaction was then quenched by addition of water (100 mL). The organic layer was collected and concentrated to produce a viscous oil, which was triturated with pentane. The triturated product (compound 2) (7.5 g) was dissolved in glacial acetic acid (150 mL) and N-chlorosuccinimide (5.5 g, 1.5 mole eq) was added. The reaction solution was heated at 90° C. for 3 hours. The reaction solution was cooled and quenched by the addition of saturated sodium bicarbonate solution (500 mL). The reaction mixture was extracted with ethyl acetate (3×150 mL) and the combined ethyl acetate fractions were dried with sodium sulfate and concentrated to produce an oil. The oil was triturated with pentane to afford 4,5-dichloro-N-(2-chloro-4-fluorophenyl)-1H-pyrazole-3-carboxamide (compound 3) (5.3 g). $^1$H NMR (DMSO-$d_6$, 400 MHz) δ 14.54 (s, 1H), 9.73 (s, 1H), 7.87 (dd, 1H, J=5.9, 8.5 Hz), 7.59 (dd, 1H, J=2.3, 8.3 Hz), 7.30 (ddd, 1H, J=2.3, 8.3, 8.5 Hz).

4,5-Dichloro-N-(2-chloro-4-fluorophenyl)-1H-pyrazole-3-carboxamide (3) (0.5 g) was dissolved in THF (5 mL). To this solution was added 1.6 g of cesium carbonate (3 mole eq) followed by di-tert-butyl(chloromethyl) phosphate (0.5 g, 1.5 mole eq). The mixture was heated to 80° C. for 20 hours. The reaction was then stopped by the addition of water (20 mL) and the mixture was extracted with ethyl acetate (3×10 mL). The combined organic layers were dried with sodium sulfate and concentrated. The residue was purified by silica gel column chromatography to afford di-tert-butyl ((4,5-dichloro-3-((2-chloro-4-fluorophenyl)carbamoyl)-1H-pyrazol-1-yl)methyl) phosphate (compound 4) (230 mg).

A solution of di-tert-butyl ((4,5-dichloro-3-((2-chloro-4-fluorophenyl)carbamoyl)-1H-pyrazol-1-yl)methyl) phosphate (compound 4) (230 mg) in dichloromethane (2.5 mL) and TFA (70 µL) was stirred at room temperature for 30 minutes. The solvent was removed by rotary evaporation and TFA was quenched by addition of saturated sodium bicarbonate. The mixture was extracted with ethyl acetate (3×10 mL). The combined organic layers were concentrated to produce oil which was triturated with pentane to afford (4,5-dichloro-3-((2-chloro-4-fluorophenyl)carbamoyl)-1H- pyrazol-1-yl)methyl dihydrogen phosphate (compound 5) (110 mg). $^1$H NMR (DMSO-d$_6$, 400 MHz) δ 9.98 (s, 1H), 7.75 (dd, 1H), 7.56 (dd, 1H), 7.27 (ddd, 1H), 5.87 (d, 2H).

Example 3: Phosphatase Treatment of Compound 5

To determine if there was effect of addition phosphatase to the phosphate, 30 units of alkaline phosphatase (EMD Millipore Phosphatase, Alkaline, Calf Intestine catalog number 524572) was added to compound 5 and the UV spectrum (210-600 nm) was measured before and after addition of phosphatase. The was a shift in the absorbance maximum from 250 to 260 nm. The ratio of 250/260 went from 0.924 to 1.067 after phosphatase treatment.

Phosphatase treatment was repeated with 0.1 unit of phosphatase (56 ug) and 0.6 mM compound 5 at a volume of 100 uL (100 mM Tris pH 8.8, 5 mM MgCl$_2$) and monitored as function of time. The half-life of the reaction was 2 minutes, meaning that the phosphatase cleaved the phosphate at a rate of 0.015 µmol/min. A unit is defined as the amount that can hydrolyze 1 µmol/min of p-nitrophenyl phosphate (PNP). Meaning that 0.1 unit of enzyme was hydrolyzing 0.015 units of phosphate: a ~6.6 fold decrease in activity relative to PNP.

Example 4: Recombinant Human ALOX15 Assay

Generation of Stock Solutions:
5 mM of compound 5 in 100 mM Tris-HCl buffer pH 8.6 and 1 mM MgCl$_2$ was treated by the addition of 0.1 unit of alkaline phosphatase (Alkaline, Calf Intestine EMD Millipore catalog number 524572). Within a minute of phosphatase addition, a white precipitate appeared. The enzymatic reaction was quenched and precipitate (presumably compound 3) was dissolved by the addition of 2 volume equivalents of DMSO to yield 1.66 mM solution. Three solutions were generated: compound 3, compound 5 with phosphatase treatment, and compound 5 without phosphatase treatment.

Lipoxygenase Enzyme Assay:
Lipoxygenase activity was measured in black 384-plates from Corning (#3711) in quadruplicate. To each well in a 384-well plate, the following were added: 15 µL of human lipoxygenase (Genway ALOX15 Active Human Recombinant Protein, GWB-6672E3) diluted in PBS at 3.18 µg/mL or PBS alone and 15 nL of 66% DMSO or compound dissolved in 66% DMSO. This mixture was incubated for 5 min before the addition of 1.5 µL 0.2 mM arachidonic acid. The plate was then incubated at room temperature for 10 min before the reaction was terminated with 2 volumes (30 µL) of 1:1 methanol:DMSO containing 0.125 mM diphenyl-1-pyrenylphosphine (DPPP). Fluorescence was measured after 30 min (excitation filter 330/30 nm, and emission filter 385/35 nm using a ClarioStar plate reader).

The relative activity of ALOX15 as a function of [compound 3] and [compound 5] was calculated by the following equation:

$$(I-I_{blank})/(I_{ALOX}-I_{blank})$$

Where I is the fluorescent intensity at each concentration, $I_{blank}$ is the intensity in the absence of ALOX15 and $I_{ALOX}$ is the intensity observed in the absence of inhibitor. A plot of the relative ALOX15 activity as a function of inhibitor concentration resulted in IC$_{50}$ values of 36 nM for compound 3 and 32 nM for phosphatase-treated compound 5. No inhibition was observed for compound 5 in the absence of treatment with phosphatase.

The absorbance change (from 250 to 260 nm) shown in Example 3 and the dependence of ALOX15 inhibition on phosphatase treatment shown in Example 4 above are consistent with a mechanism of compound 3 generation upon enzymatic hydrolysis of compound 5 followed by spontaneous hydrolysis of the methylene spacer.

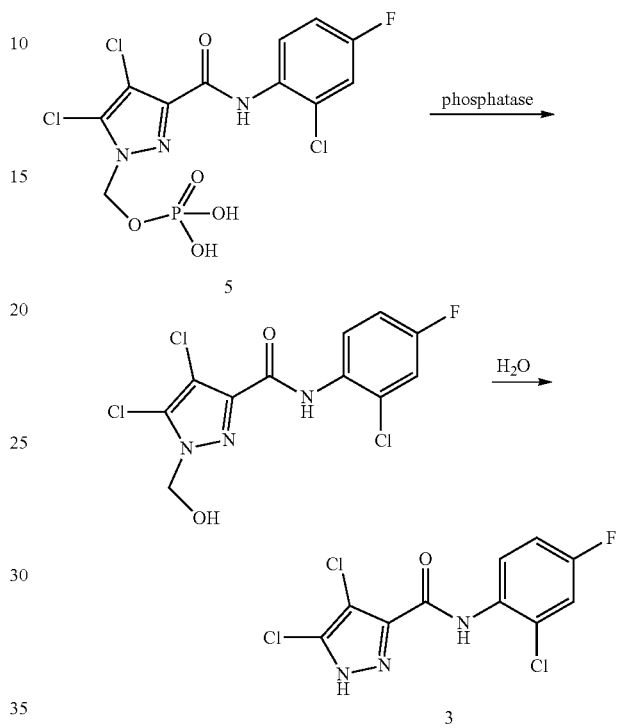

Example 5: Phosphatase Treatment of Compound 5 and Conversion to Compound 3

To monitor the product of phosphatase treatment, compound 5 at 1 M was incubated at 37° C. with alkaline phosphatase (Merck) at 10 or 0.1 mU/ml for 15 minutes. Levels of compound 3 were analyzed by LC-MS/MS.

As shown in FIG. 1, compound 3 molecular ion is generated upon exposure of compound 5 to sufficient quantities of alkaline phosphatase.

Example 6: Solubility Assessment of Compound 5 as Free Phosphoric Acid

Water was added slowly to 4.7 mg of compound 5 until 4.7 ml of water was added at which point the phosphate fully dissolved. The pH of the solution was estimated using litmus paper and estimated to be <3. Without a counterion, the molecular weight of the phosphate is 418 m. Therefore, at 1 mg/ml, the concentration is 2.4 mM.

For comparison, compound 3 is soluble to 0.4 µg/ml (Han et al FASEB J. 2017 31(2):491-504), which at a molecular weight of 308 is 1.3 µM. Therefore, the addition of the phosphoric acid group to compound 3 results in a ~1800 fold increase in water solubility.

The stock of phosphate was diluted to 0.1 mg/mL and the UV absorbance spectrum was measured from 210 to 600 nm. The maximum absorbance of 0.156 was at 250 nm.

From a pathlength of nanodrop (1 mm), the extinction coefficient at 250 nm is 6,520 M cm$^{-1}$.

Solubility of Compound 5 as Disodium Salt:

Compound 5 was suspended in water (at weight to give a final concentration of 10 mM) and then 2 eq NaHCO$_3$ was added. The cloudy suspension gives an immediate clear solution on shaking and a further 4-fold increase in solubility as a sodium salt (7,200 fold increase in water solubility above compound 3).

Example 7: Inhibition of 15-Lipoxygenase in Human Primary Eosinophils

Figure 2:
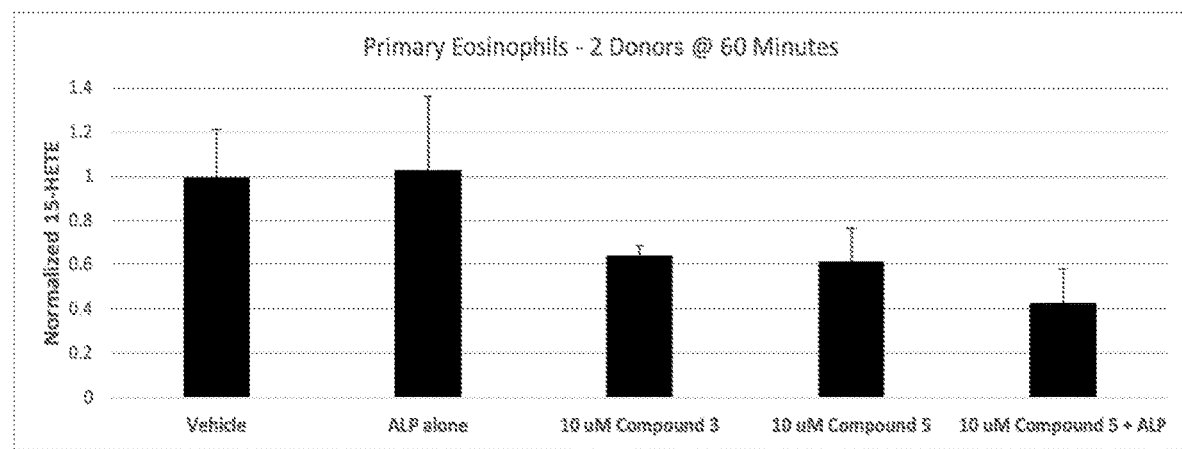
FIG. 2 depicts inhibition of 15-lipoxygenase in primary peripheral blood eosinophils for compound 3, compound 5, and compound 5 pre-treated with alkaline phosphatase.

In this experiment, inhibition of 15-lipoxygenase was performed in primary peripheral blood eosinophils, to evaluate the effect on arachidonic acid metabolite production. Primary peripheral blood eosinophils from 2 separate donors (StemExpress) were thawed from frozen and allowed to recover in growth media for 4 hours at 37° C. Cells were washed with Hank's Balanced Salt Solution, then aliquoted into 96 well round bottomed plate at 1*10$^5$ cells/well, 200 μL/well. Cells were treated with either 10 μM compound 3, 10 μM compound 5 or 10 μM compound 5+0.2 U alkaline phosphatase (ALP) pretreated for 15 minutes. Arachidonic acid was added to final concentration of 3 μM and experiment started. At 1 hour post-treatment the supernatant was collected and 15(S)-HETE was quantified by ELISA (Cayman Chemical) according to manufacturer's recommended protocol. Comparisons were made between the cells treated with the test compounds and cells treated with vehicle only. As shown in FIG. 2, treatment with compound 3 or compound 5 results in approximately 40% decrease in 15-HETE production compared to vehicle or ALP alone. Treatment with compound 5 that has been pretreated with ALP results in approximately 60% decrease in 15-HETE production compared to vehicle or ALP alone. The effect of compound 5 that has not been pretreated with ALP can be attributed to enzymatic hydrolysis of phosphate ester by endogenous phosphatases.

Example 8: Inhibition of 15-Lipoxygenase in Human Cells

In this experiment, inhibition of 15-lipoxygenase is performed in primary human nasal epithelial cells (pHNEC) and primary peripheral blood eosinophils, to evaluate the effect on arachidonic acid metabolite production.

Primary human nasal epithelial cells (pHNEC) and primary peripheral blood eosinophils induced for 24 hours with 20 ng/mL IL13 are treated with 10 μM of a test compound, or vehicle only (DMSO) for 5 minutes prior to the addition of 10 uM arachidonic acid. At 2 hours post-treatment the supernatant is collected and arachidonic acid metabolites of 15-lipoxygenase including prostaglandin E2, cysteinyl leukotrienes (LTC4, D4, and E4), and 15(S)-HETE are quantified by ELISA (Cayman Chemical) according to manufacturer's recommended protocol. Comparisons are made between the groups treated with the test compounds and cells treated with vehicle only.

Example 9: Inhibition of 15-Lipoxygenase in a Murine Model for Nasal Polyposis

In this experiment, a murine model of nasal polyposis is used to evaluate the effect of inhibition of 15-lipoxygenase. The murine model consists of inducing chronic rhinitis with ovalbumin (OVA) treatment, followed by a combination of ovalbumin and *Staphylococcus aureus* enterotoxin B (SEB) treatment leading to nasal polyp formation. This model has characteristics of the human disease.

2-week-old female BALB/c mice are obtained from Charles River Laboratories. The animals are kept in environmentally controlled rooms under specific pathogen-free conditions (temperature, 20-26° C.); humidity, 30-70%) with a 12-hour light-dark cycle for 2 weeks before use. Food and water are available ad libitum. All animals are used in accordance with animal care guidelines.

Nasal polyposis is induced in age-matched (4-week-old) mice divided into five groups. Group A (n=5) is a control group in which mice are treated with neither reagent nor surgery. For groups B-E (n=5 for each), mice are sensitized with an intraperitoneal injection of 25 ug of OVA plus 2 mg of aluminum hydroxide on days 0 and 7. From Day 14 to Day 20 mice are nasally challenged daily with 6% OVA. From Day 20, 6% OVA+*Staphylococcus aureus* enterotoxin B (10 ng) is instilled into the nasal cavity of mice three times per week for 8 weeks.

From week 4, animals in groups B-E receive 10 ul of 1 mg/mL of a test compound (groups B-D) or vehicle only (1 part DMSO, 9 parts PBS) (group E) three times a week for 4 weeks. Anesthesia during intranasal administration is achieved with intraperitoneal injection of 0.2 ml nembutal (5 mg/ml).

At the end of eight weeks of OVA+SEB and inhibitor treatment, mice are euthanized by cervical dislocation following injection of 0.3 ml nembutal. Nasal cavity samples are prepared using a large scalpel to remove the snout with a transverse cut behind the back molars. The external nares are flushed with PBS to wash out any blood within the nasal cavity. Histologic quantification of the number of nasal polyps and the amount of eosinophil infiltration is performed using hematoxylin and eosin (H&E) staining of the nasal cavity. The number of polyps and amount of eosinophilic infiltration is compared between all groups. Additionally, nasal mucosa is removed using a small curette after bisecting the nasal tissue sagitally along the nasal septum. Cell lysates are prepared using a RIPA buffer, and these lysates are used to measure arachidonic acid metabolites of 15-lipoxygenase including prostaglandin E2, cysteinyl leukotrienes (LTC4, D4, and E4), and 15(S)-HETE. The metabolites are quantified by ELISA (Cayman Chemical) according to manufacturer's recommended protocol. Comparisons are made between the control group, groups treated with the test compounds and the group treated with vehicle only.

Example 10: Inhibition of 15-Lipoxygenase in a Rabbit Model for Nasal Polyposis

In this experiment, a rabbit model of nasal polyposis is used to evaluate the effect of inhibition of 15-lipoxygenase. In the rabbit model eosinophilic nasal polyps are induced by eliciting an allergic reaction in animals with ovalbumin (OVA) and poly-L-arginine treatment. This model has characteristics of the human disease.

Male New Zealand white rabbits are obtained from Charles River Laboratories. The animals are kept in environmentally controlled rooms under specific pathogen-free conditions (temperature, 20-26° C.); humidity, 30-70%) with a 12-hour light-dark cycle for 2 weeks before use. Food and water are available ad libitum. All animals are used in accordance with animal care guidelines.

Maxillary sinusitis is induced in age-matched (13-week-old) rabbits divided into five groups. Group A (n=4) is a control group in which rabbits are treated with neither reagent nor surgery. For groups B-E (n=6 for each), rabbits are sensitized by subcutaneous injection with 1 mL of saline containing 2.5% OVA plus 0.4% alum on days 0 and 7. On day 14, under anesthesia with i.v. injection of 25 mg/kg of pentobarbital sodium (Nembutal, Dainippon Sumitomo Pharma, Osaka, Japan), nasal dorsa are incised to expose maxillary sinus cavities and both sides of the ostia were occluded with plugs of sterile cotton wool and butylcyanoacrylate tissue glue (Histoacryl; B. Braun, Melsungen AG, Germany) under a microscope. After 2 weeks of wound closure, OVA is administered into both sides of the maxillary sinuses (0.5 mL/sinus of 2.5% OVA in saline, three times a week for 2 weeks). Thereafter, the animals in groups B-D receive 5 mg/mL poly-L-arginine in saline three times a week for 4 weeks.

After induction of maxillary sinusitis with OVA and poly-L-arginine, the animals receive 100 ul of 1 mg/mL of a test compound (groups B-D) or vehicle only (1 part DMSO, 9 parts PBS) (group E) three times a week for 4 weeks. One week after the last administration into the maxillary sinus, the rabbits are sacrificed by i.v. injection of pentobarbital sodium and the anterior nasal region with the attached bone, excluding the ocular bulb, is dissected. The mucosal tissues for gene analysis are collected from the right side of the maxillary sinus and stored in RNAlater RNA stabilization reagent (Ambion, Austin, Tex.) at 4° C. until analysis. The left side of the maxillary sinus is used for histopathological analysis. Anesthesia for administration of the test compounds is achieved with intraperitoneal injection of 0.2 ml nembutal (5 mg/ml).

Antibodies to OVA are measured using enzyme-linked immunosorbent assay (ELISA). Blood samples are collected from the pinna vein on day 13 to measure OVA-specific IgG levels. ELISA is performed according to the protocol of a previous study. The titers of samples are calculated by comparison with internal standard serum, prepared from the rabbits immunized with 2.5% OVA plus 0.4% alum eight times. The value of this standard is arbitrarily calculated as 10,000 U/ml.

Histopathological analysis of nasal tissue is carried out on tissue fixed with 10% neutral buffered formalin solution for 1 week, decalcified in 0.5 mol/L of ethylenediaminetetraacetic acid at 37° C., embedded in paraffin, and cut into 2-µm-thick sections. After hematoxylin-eosin staining, histopathological analysis is performed by selecting a representative field of mucosa per sinus where the most prominent change is detected with 200× magnification. The number of eosinophils and the area of mucosa in each field are measured to calculate the density of eosinophils (cells/mm2). The width of the lamina propria (µm) is measured as an indirect indication of mucosal hypertrophy. The degree of polyp formation is graded semiquantitatively according to the following score: 0=little or no polyp formation detected; 1=slight (slight prominence of mucosa); 2=moderate (polyp of a size from one-quarter to one-half of the field); 3=severe (polyp of a size more than one-half of the field).

Example 11: Inhibition of 15-Lipoxygenase in Human Primary Eosinophils with Short-Term Exposure The main objective of this study was to determine the effect of short-term exposure of compound 3 and compound 5 on the levels of 15-HETE (a 15-lipoxygenase metabolite of arachidonic acid) in primary peripheral blood eosinophils.

Two independent experiments were performed in which primary peripheral blood eosinophils (StemExpress) were thawed from frozen and allowed to recover in growth media for 4 hours at 37° C. Cells were washed with Hank's Balanced Salt Solution, then aliquoted into 5 mL glass tubes 5*104 cells/tube, 300 µL/tube. Cells were treated with either 10 µM compound 3, 10 µM compound 5, or vehicle (DMSO) for 30 minutes. Arachidonic acid was added to final concentration of 3 µM and experiment started. At 5 minutes post-treatment, the entire reaction was quenched with an equal volume of extraction buffer (methanol, 60 mM ascorbic acid, 0.1% acetic acid) and 15-HETE quantified. Briefly, 15-HETE was quantified using LC-MS/MS (QTrap5500, Applied Biosystems). Q1/Q3 masses: 319.10/219.10 for 15-HETE. Deuterated 15-HETE (Cayman Chemical) was used as the internal standard. The Q1/Q3 masses are 327.10/184.10 Da for the 15-HETE deuterated standard. Oxidized fatty acids were extracted using liquid/liquid extraction with acetonitrile as a diluent. Reverse chromatography was performed using a Unison UK-C18 column (Imtakt, 50×3 mm i.d., 3 µm, PN: UK-032) using a water/acetonitrile gradient containing 0.05% ammonium hydroxide and 0.1% formic acid.

Figure 3:
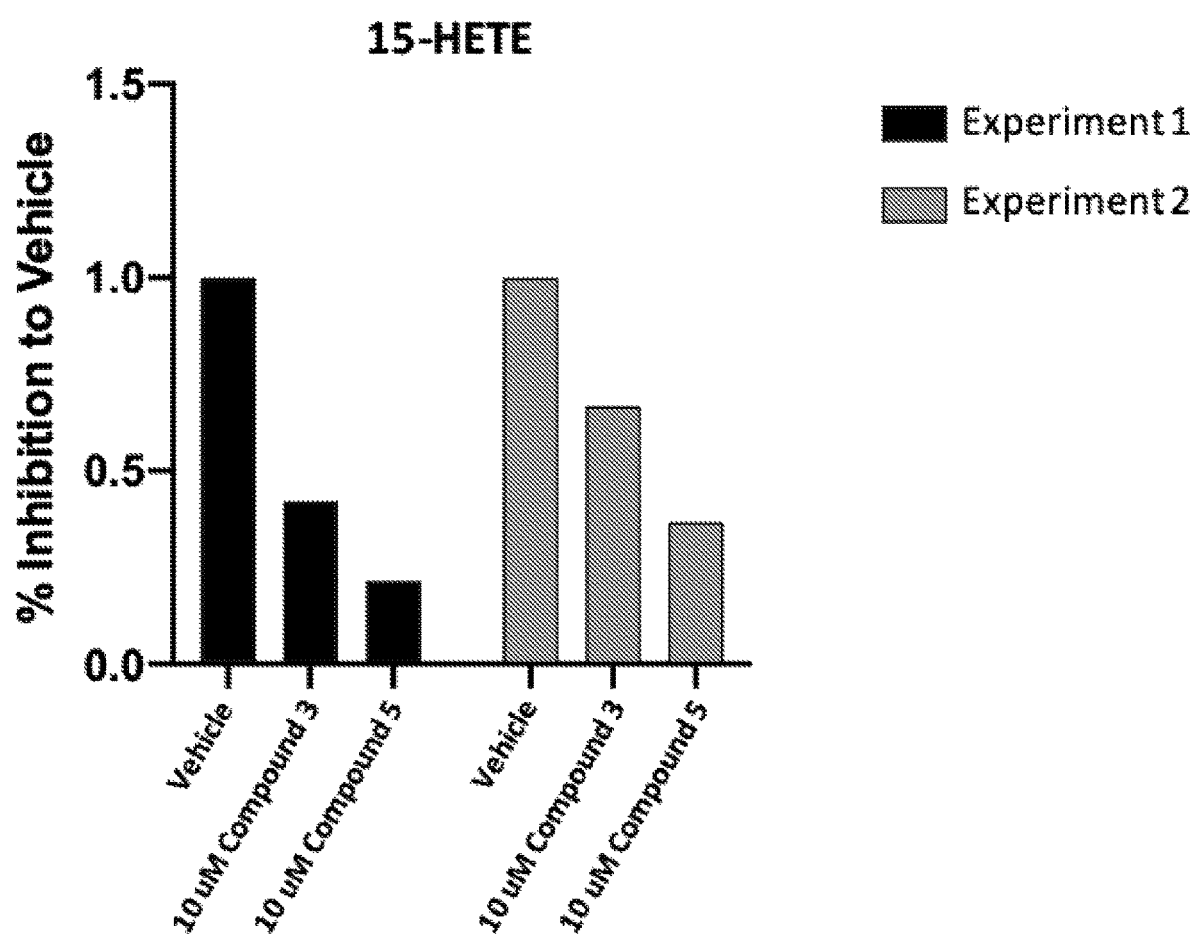
FIG. 3 depicts inhibition of 15-lipoxygenase in primary peripheral blood eosinophils for compound 3 and compound 5 in two independent experiments, as analyzed by LC-MS/MS of 15-HETE levels.

Comparisons were made between the cells treated with the test compounds and cells treated with vehicle only. As summarized in FIG. 3, Experiment 1 showed cells treated with compound 3 had 58% less 15-HETE relative to cells treated with vehicle only, while treatment of cells with compound 5 had approximately 79% less 15-HETE relative to cells treated with vehicle only. In Experiment 2, compound 3 treatment reduced 15-HETE by 33% relative to cells treated with vehicle only, while treatment of cells with compound 5 had 63% less 15-HETE relative to cells treated with vehicle only.

Example 12: Lowering of ALOX15 Metabolite Levels, and ALOX15 and POSTN mRNA Expression, after Administration of Compound 5 in an In Vitro Primary Human Nasal Epithelial Cell Model The main objective of this study was to determine the effect of continuous exposure of compound 5 on the levels of ALOX15 products (13-HODE and 15-HETE) and expression of ALOX15 and POSTN mRNA in a human nasal epithelial primary cell model over the course of three days.

Human nasal epithelial primary cells (HNEpC) (PromoCell GmbH, Heidelberg, Germany) were cultured according to the manufacturer in provided Primary Cell media in 24 well plates at a density of 25,000 cells per well. Cells were treated with 5 µM or 1 µM of compound 5 or vehicle only (water) in media containing 20 ng/mL IL-13 for 24 hours in a 37° C. cell culture incubator. The following day, media was replaced and fresh media containing 20 ng/mL IL-13 and compound 5 or vehicle was added to each well, then incubated again for 24 hours in a 37° C. cell culture incubator. The process was repeated once more for a 24-hour period.

To determine levels of arachidonic acid and linoleic acid metabolites after compound treatment, cell media was replaced with fresh Primary Cell media without IL-13. ALOX15 substrate (arachidonic acid or linoleic acid) was added to each well at a concentration of 1.5 µM and cells further incubated 37° C. for 1 hour. Media was collected from each well and quenched with an equal volume of LC/MS extraction buffer (methanol, 60 mM ascorbic acid, 0.1% acetic acid).

Figure 4:
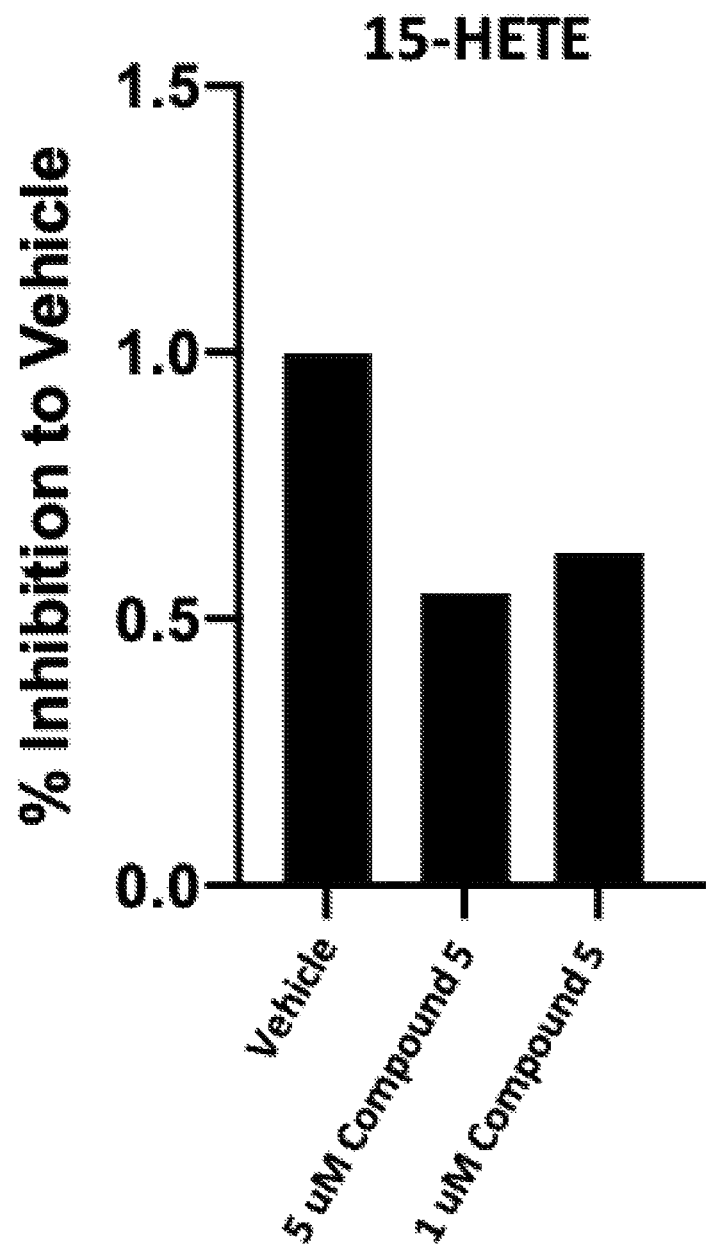
FIG. 4 depicts inhibition of 15-lipoxygenase in primary nasal epithelial cells for two concentrations of compound 5, as analyzed by LC-MS/MS of 15-HETE levels.
Figure 5:
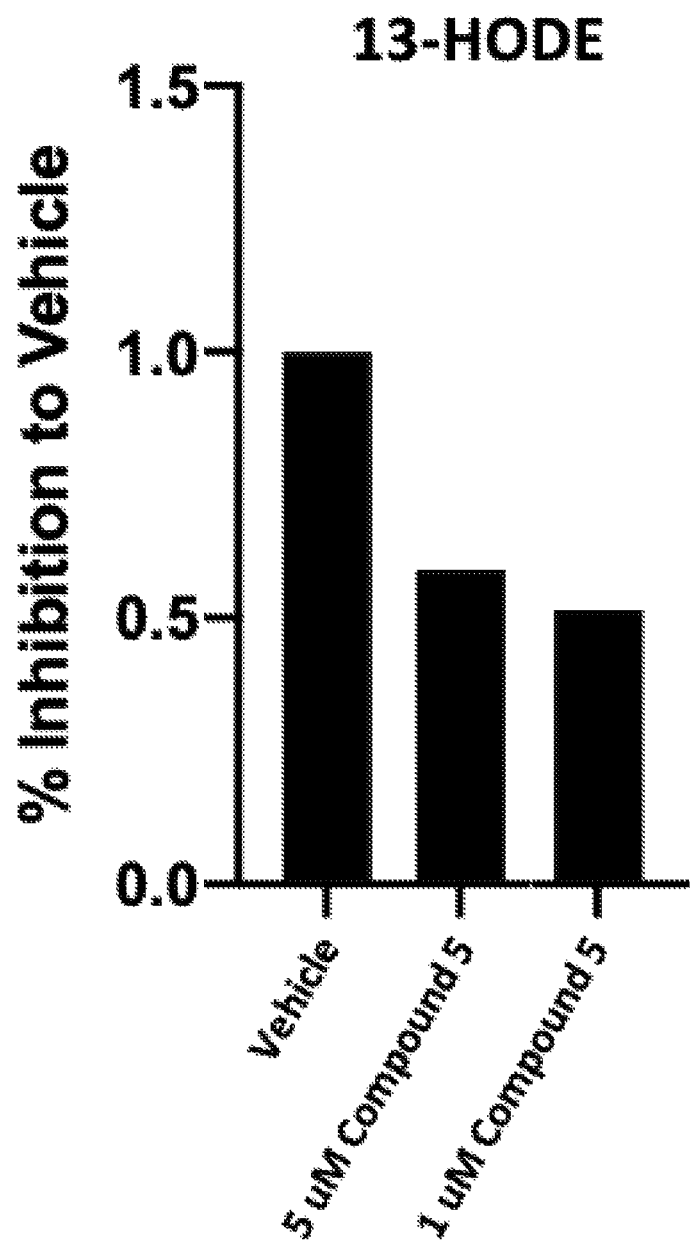
FIG. 5 depicts inhibition of 15-lipoxygenase in primary nasal epithelial cells for two concentrations of compound 5, as analyzed by LC-MS/MS of 13-HODE levels.

15-HETE and 13-HODE were quantified using LC-MS/MS (QTrap5500, Applied Biosystems). Q1/Q3 masses: 319.10/219.10 for 15-HETE and 295.10/195.10 Da for 13-HODE. Deuterated 15-HETE (Cayman Chemical) was used as the internal standard. The Q1/Q3 masses are 327.10/184.10 Da for the 15-HETE deuterated standard. Oxidized fatty acids were extracted using liquid/liquid extraction with acetonitrile as a diluent. Reverse chromatography was performed using a Unison UK-C18 column (Imtakt, 50×3 mm i.d., 3 μm, PN: UK-032) using a water/acetonitrile gradient containing 0.05% ammonium hydroxide and 0.1% formic acid. Cells treated with compound 5 produced less 15-HETE and 13-HODE than cells treated with vehicle alone as shown in FIG. 4 and FIG. 5, respectively.

Figure 6:
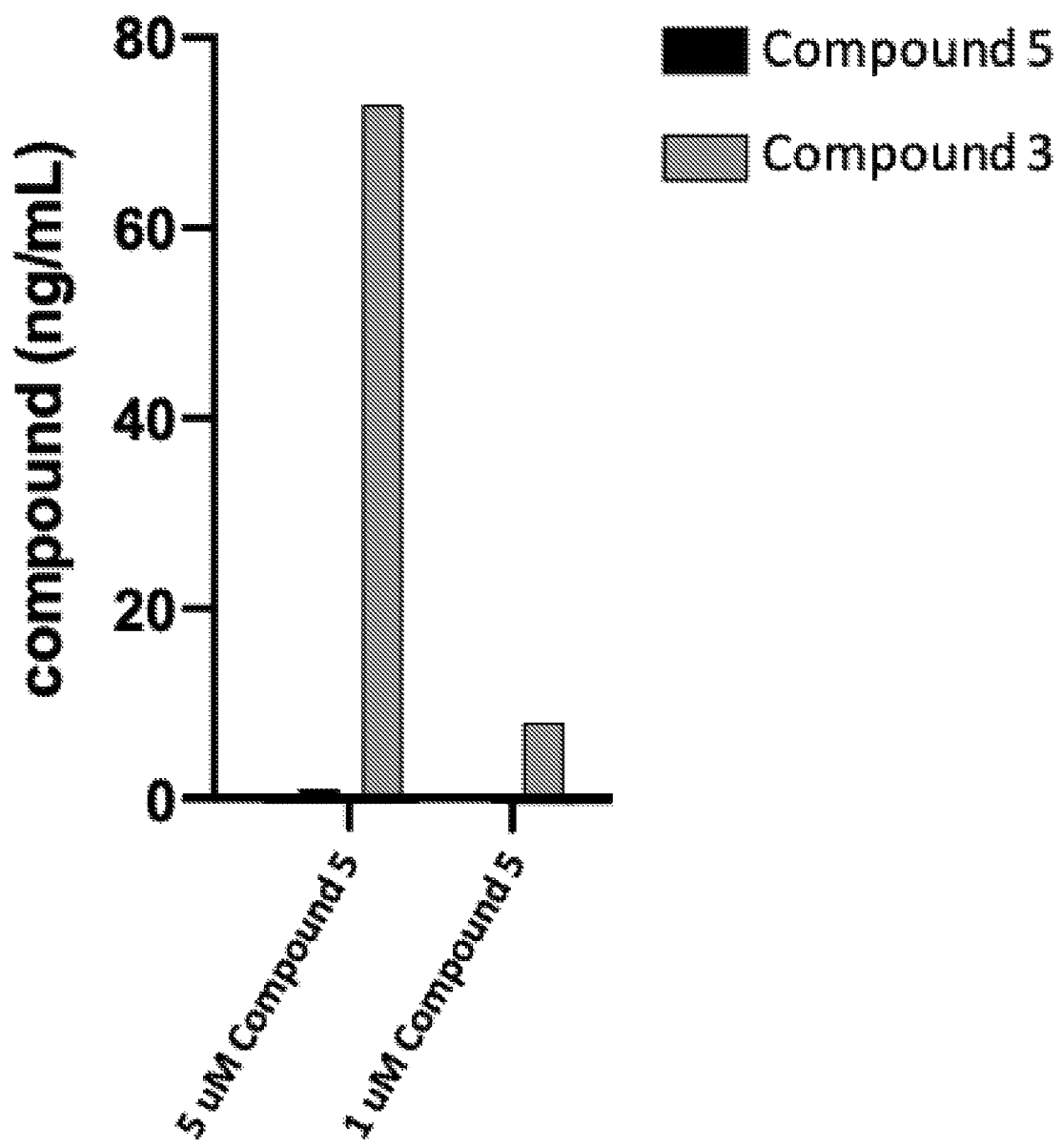
FIG. 6 depicts levels of compound 3 and compound 5 following treatment of primary nasal epithelial cells with two concentrations of compound 5, as analyzed by LC-MS/MS.

From the quenched media samples, compound 5 and compound 3 were also quantified. Compound 3 was quantified using LC-MS/MS (QTrap5500, Applied Biosystems). Q1/Q3 masses: 306.00/135.00 using a deschloro derivative of compound 3 (lacking chlorine at 4 position of pyrazole ring) as an internal standard. The Q1/Q3 masses are 272.00/101.00 Da for the internal standard. Compound 3 was extracted using liquid/liquid extraction with methanol as a diluent. Reverse chromatography was performed using a Unison C18 column (Imtakt, 50×2 mm i.d., 3 μm, PN: UK-022) using a water/acetonitrile gradient containing 0.05% ammonium hydroxide. Compound 5 was quantified using LC-MS/MS (QTrap5500, Applied Biosystems). Q1/Q3 masses: 418.00/79.00 Da. Fosphenytoin was used as an internal standard. The Q1/Q3 masses are 361.00/79.00 Da for the internal standard. Compound 5 was extracted using liquid/liquid extraction with acetonitrile as a diluent. Reverse chromatography was performed using a Unison C18 column (Imtakt, 50×2 mm i.d., 3 μm, PN: UK-022) using a water/acetonitrile gradient containing 0.05% ammonium hydroxide. As shown in FIG. 6 the majority of compound 5 was converted to compound 3.

Figure 7:
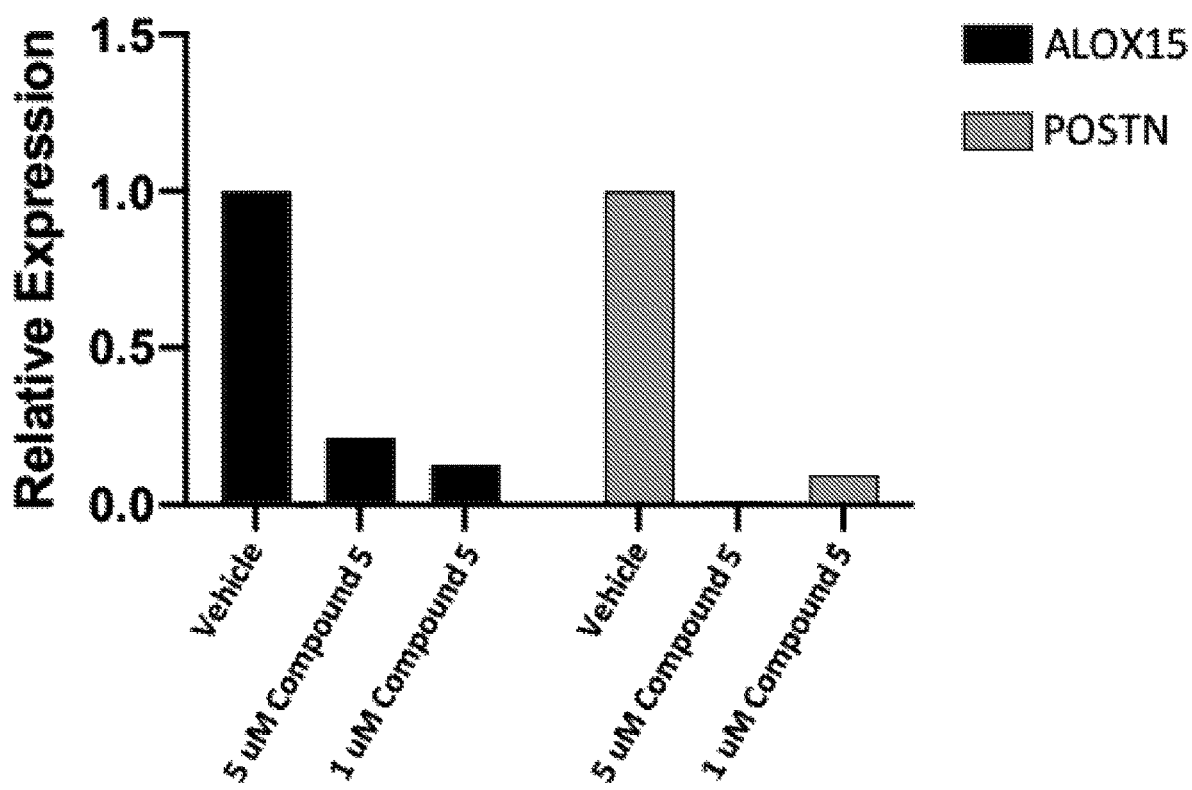
FIG. 7 depicts levels of ALOX15 and POSTN mRNA following treatment of primary nasal epithelial cells with two concentrations of compound 5, as analyzed by RT-qPCR.

ALOX15 and POSTN mRNA levels were measured by RT-qPCR. After removal of cell media, HNEpCs were removed from the wells by enzymatic treatment using 1×TrypLE (ThermoFisher). Cells were then washed twice with cold 1×PBS and cell RNA isolated and cDNA synthesized using TaqMan Fast Advanced Cells-to-Ct Kit (ThermoFisher). The level of ALOX15 mRNA from each sample was measured in triplicate by real-time qPCR on an Applied Biosystems 7500 Fast Real-Time PCR machine using the TaqMan Gene Expression Assay for human ALOX15 (ThermoFisher, assay #Hs00993765_g1). The level of PPIA mRNA was measured in biplex reactions using TaqMan Gene Expression Assay (ThermoFisher, assay #Hs99999904_m1) and used to determine relative ALOX15 mRNA levels in each well using the delta-delta Ct method. All data were normalized to relative ALOX15 mRNA levels in samples from cells treated with vehicle only. Relative POSTN mRNA levels were measured as above using TaqMan Gene Expression Assay specific for human POSTN mRNA (ThermoFisher, assay #Hs00170815_m1). The results are shown in FIG. 7. Relative levels of ALOX15 and POSTN mRNA in cells treated with compound 5 were lower than the levels from cells treated with vehicle.

Example 13: Lowering of 15-HETE Levels, and ALOX15 and POSTN mRNA Expression, after Nasal Administration of Compound 5 in a Rabbit Model of Inflammation The main objective of this study was to determine the effect of repeat nasal administration of compound 5 on the level of 15-HETE and expression of ALOX15 and POSTN mRNA in the nasal tissues of rabbits after intranasal administration of IL4 and IL13 over the course of one day. POSTN is a known biomarker for the Th2 cytokine inflammation that is characteristic of eosinophilic nasal polyps.

Six (6) female NZW rabbits were employed in this study. Rabbits were obtained from Covance (Denver Pa.). Rabbits were between approximately 10 and 12 months of age at the time of study start. At time point 0, all animals received 50 μL of solution containing rabbit IL4 (RND Systems/Biotechne) and human IL13 (PreproTech) at a concentration of 0.25 mg/mL each in 0.5×PBS containing 12.5 mg/mL BSA per nostril. This was administered intranasally via a venous catheter attached to a micropipette. The animal was positioned in a supine manner and the venous catheter inserted into the nostril. The volume was introduced into the nasal cavity and the same procedure was repeated with the other nostril.

At the 2, 4, and 6 hour time points, animals in Group 1 (n=3) received 0.2 mL of vehicle (0.9% saline) per nostril and the animals in Group 2 (n=3) received 0.2 mL of compound 5 (10 mM) in vehicle per nostril. The dosing of vehicle and compound 5 proceed as follows: The animal was positioned in a supine manner in a restraint bag and a mucosal atomization device (MAD) attached to the pre-filled tuberculin syringe was inserted into the nostril and introduced into the nasal cavity. The same procedure was repeated with the other nostril.

At the 8 hour time point, all the nostrils of all animals were lavaged with 1 mL of 0.9% saline per nostril and the resulting fluid collected. Intranasal lavages were performed as follows: The animals were held sternally in a restraint bag with the head over the edge of the table and the rear of the animal elevated higher than the head. A flexible venous catheter was inserted in the nostril until resistance was felt. The 1 mL of saline was introduced through the catheter into the nasal cavity. The nasal lavage returned from the nostril was collected via a funnel into a conical tube and the approximate volume recorded. This procedure was repeated for the other nostril. The lavage was stored at approximately −70° C. until analysis. Following (<10 minutes) the 8 hour time point lavage, blood was collected from all animals, processed to serum, and frozen at approximately −70° C. until analysis.

Animals were then euthanized and nasal mucosa was collected. A total of 4 areas within the nasal cavities were sampled for mucosal tissue from each animal. They were: left rostral area; left caudal area; right rostral area; and right caudal area. The skin was removed from the skull and the skull initially separated into a rostral section and a caudal section along a transverse plane. The left and the right nasal cavities were exposed using scissors or a scalpel blade. A scalpel or microspatula was used to scrape mucosal tissue from the left and right nasal passages. Tissues from the left and right nasal cavities were collected separately. The resulting tissue from each nostril was minced together then divided in two. Once piece was placed in 600 μL RNAlater and stored at approximately 4° C. overnight before being moved for longer term storage at approximately −20° C. until analysis. The other piece was flash frozen in liquid nitrogen and stored at approximately −70° C. until analysis.

Figure 8:
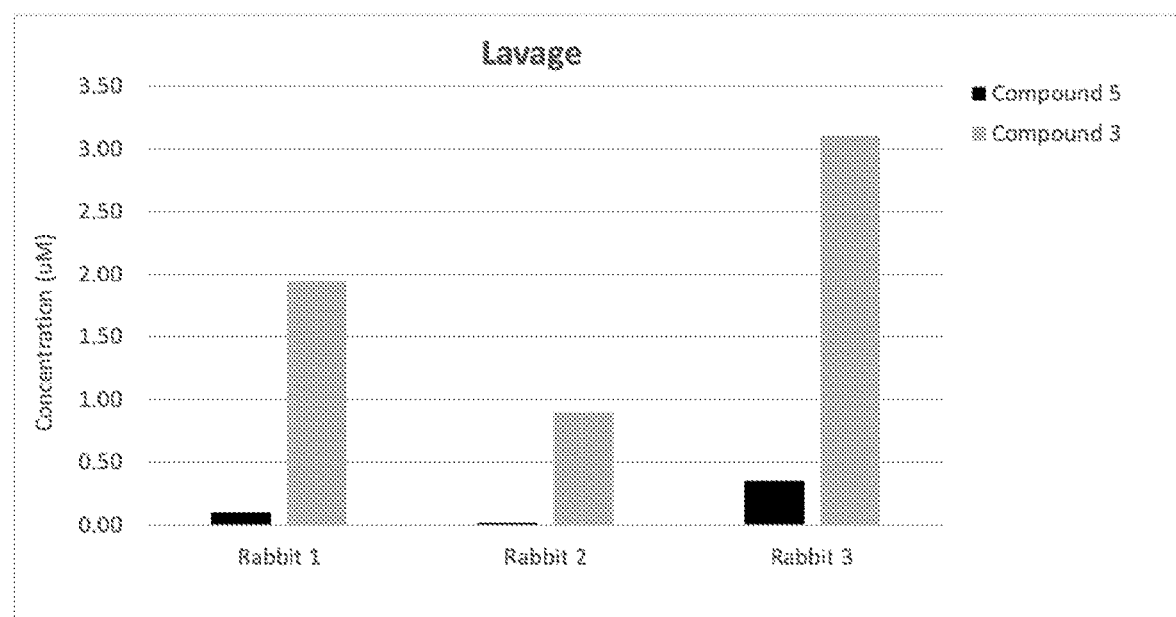
FIG. 8 depicts levels of compound 3 and compound 5 in rabbit nasal lavage following treatment with compound 5, as analyzed by LC-MS/MS.

Nasal lavage and serum samples were analyzed for the levels of compound 3 and compound 5. Frozen tissue samples were weighed (20-120 mg) and placed into 2 mL CK14 homogenizing tubes (Bertin) and 500 μL of methanol containing 1 mM butylated hydroxy toluene (BHT) and 1 mM tris(2-carboxyethyl)phosphine (TCEP) was added. The tubes were placed in a Precellys 24 tissue homogenizer (Bertin) and run at 6000 rpm six times for 20 seconds with a 10 second pause between cycles. The tubes containing the homogenized tissue were then placed in a microfuge and centrifuged for 5' at 14,000 rpm to pellet any insoluble material. Compound 3 was quantified using LC-MS/MS (QTrap5500, Applied Biosystems). Q1/Q3 Masses: 306.00/135.00 using a deschloro derivative of compound 3 (lacking chlorine at 4 position of pyrazole ring) as an internal standard. The Q1/Q3 Masses are 272.00/101.00 Da for the internal standard. Compound 3 was extracted using liquid/liquid extraction with methanol as a diluent. Reverse chromatography was performed using a Unison C18 column (Imtakt, 50×2 mm i.d., 3 mm, PN: UK-022) using a water/acetonitrile gradient containing 0.05% ammonium hydroxide. Compound 5 was quantified using LC-MS/MS (QTrap5500, Applied Biosystems). Q1/Q3 Masses: 418.00/79.00 Da. Fosphenytoin was used as an internal standard. The Q1/Q3 Masses are 361.00/79.00 Da for the internal standard. Compound 5 was extracted using liquid/liquid extraction with acetonitrile as a diluent. Reverse chromatography was performed using a Unison C18 column (Imtakt, 50×2 mm i.d., 3 mm, PN: UK-022) using a water/acetonitrile gradient containing 0.05% ammonium hydroxide. The results are shown in FIG. 8. Compound 5 was detected in the lavage samples from Group 2 animals (rabbit 1, rabbit 2, rabbit 3) and ranged in average concentration from 0.016 uM-0.35 uM. Compound 3 was also detected in all the lavage samples from Group 2 animals and ranged in average concentration from 0.89 uM-3.1 uM. As shown in FIG. 8, the majority of compound 5 was converted to compound 3. There was no quantifiable compound 5 or compound 3 in the any of the serum samples.

Figure 9:
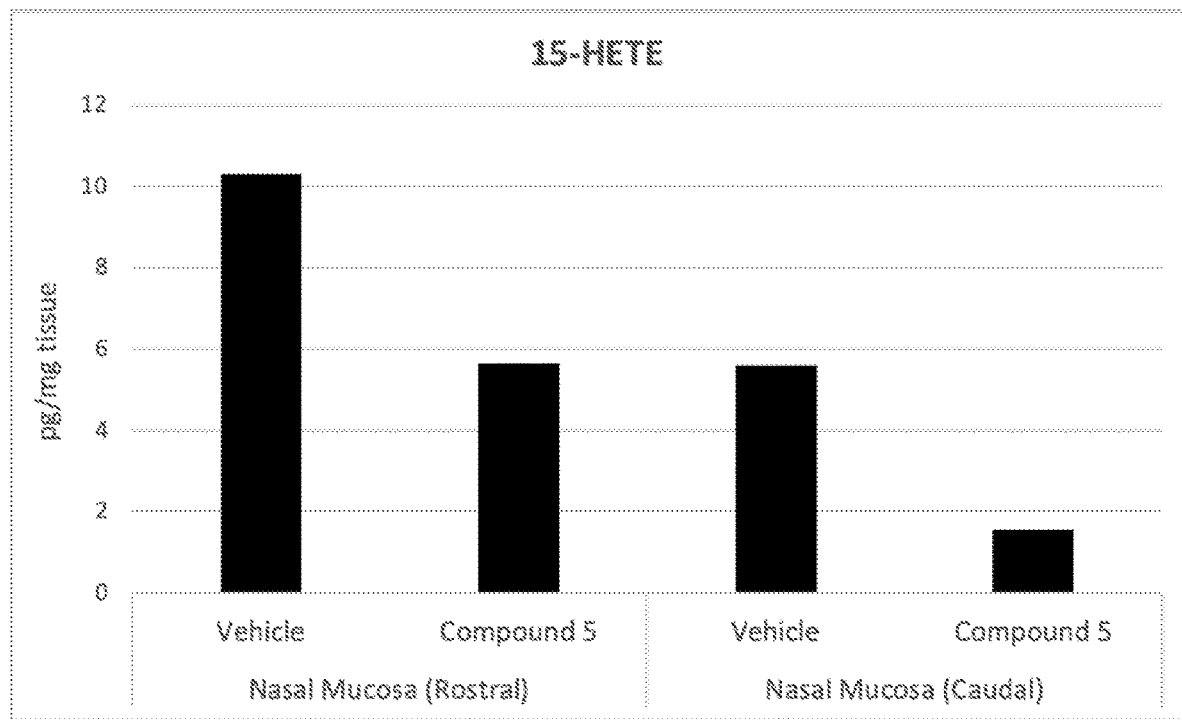
FIG. 9 depicts inhibition of 15-lipoxygenase in rostral and caudal rabbit nasal mucosa following treatment with compound 5, as analyzed by LC-MS/MS of 15-HETE levels.

The nasal mucosal tissue samples were analyzed for 15-HETE and total 15-HETE, including esterified 15-HETE. The amount of 15-HETE in the tissue supernatant was quantified using LC-MS/MS (QTrap5500, Applied Biosystems). The Q1/Q3 Masses for 15-HETE were 319.10/219.10. Deuterated 15-HETE (Cayman Chemical) was used as the internal standards. The Q1/Q3 Masses were 327.10/184.10 Da for the 15-HETE deuterated standard. Oxidized fatty acids were extracted using liquid/liquid extraction with acetonitrile as a diluent. Reverse chromatography was performed using a Unison UK-C18 column (Imtakt, 50×3 mm i.d., 3 mm, PN: UK-032) using a water/acetonitrile gradient containing 0.05% ammonium hydroxide and 0.1% formic acid. The results are shown in FIG. 9. Mean 15-HETE levels in the nasal mucosa from the rostral and caudal regions from rabbits treated with compound 5 were lower than those in the same regions from rabbits treated with vehicle.

Figure 10:
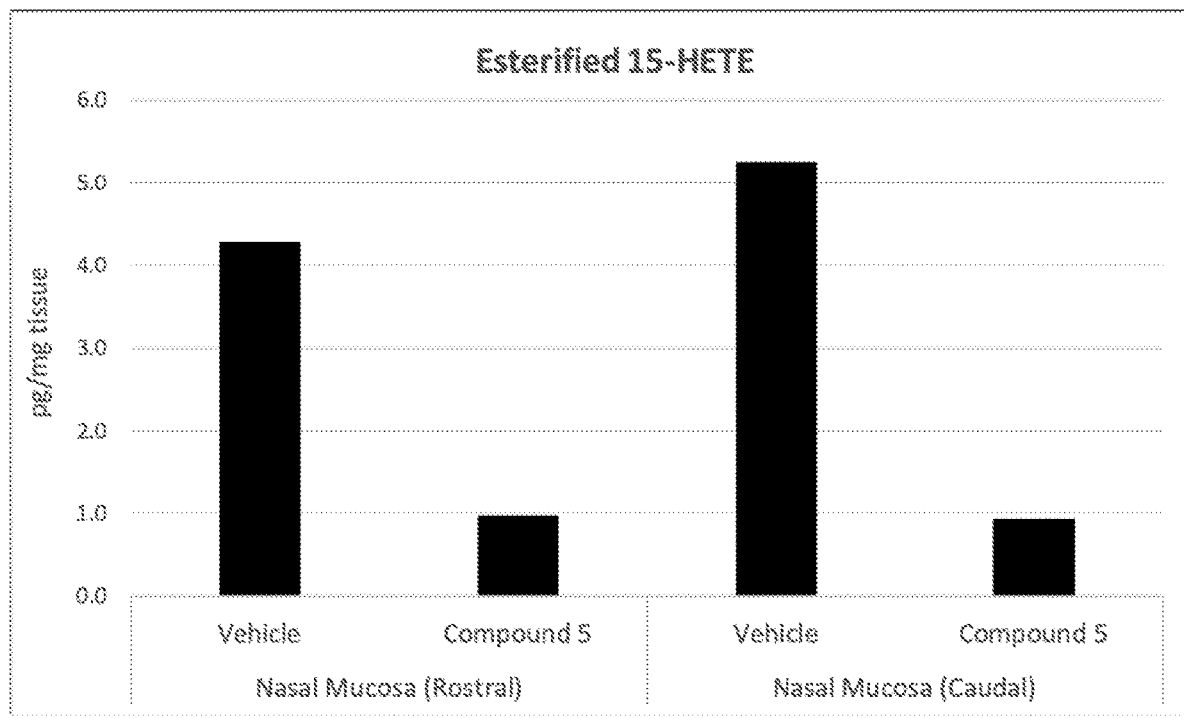
FIG. 10 depicts inhibition of 15-lipoxygenase in rostral and caudal rabbit nasal mucosa following treatment with compound 5, as analyzed by LC-MS/MS of esterified 15-HETE levels.

In order to extract total 15-HETE including esterified 15-HETE, 100 uL of the tissue supernatant used to measure 15-HETE levels was subjected to hydrolysis conditions by addition of 100 uL of 100 mM sodium hydroxide (NaOH) in water. The samples were then incubated at room temperature for 3 hours followed by addition of 100 uL of 200 mM ascorbic acid in water. The samples treated with NaOH were then assayed for 15-HETE using the methods for LC-MS/MS as described above. The amount of esterified 15-HETE was calculated by subtracting the amount of 15-HETE in untreated supernatant from the amount of 15-HETE from the supernatants treated with NaOH. The results are shown in FIG. 10. Mean esterified 15-HETE levels in the nasal mucosa from the rostral and caudal regions from rabbits treated with compound 5 were lower than those in the same regions from rabbits treated with vehicle.

Figure 11:
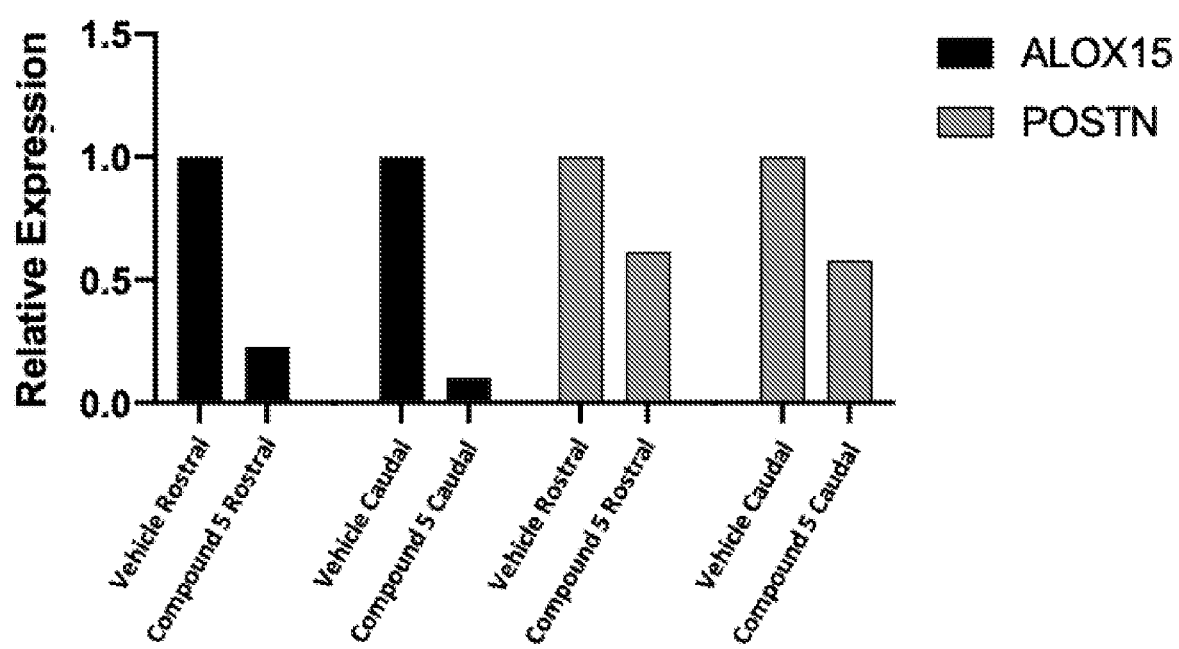
FIG. 11 depicts levels of ALOX15 and POSTN mRNA in rostral and caudal rabbit nasal mucosa following treatment with compound 5, as analyzed by RT-qPCR.

Relative ALOX15 and POSTN mRNA levels in nasal mucosa were measured by RT-qPCR. Nasal mucosal tissues were recovered from RNAlater and added to 2 mL CK14 homogenizing tubes (Bertin) containing 400 uL homogenization solution (Maxwell RSC simplyRNA Tissue Kit, Promega). The tubes were placed in a Precellys 24 tissue homogenizer (Bertin) and run at 5500 rpm two times for 10 seconds with a 10 second pause between cycles. The tubes containing the homogenized mucosal tissue were then placed in a microfuge and centrifuged for 5' at 14,000 rpm to pellet any insoluble material. The supernatant (200 uL) was placed in a fresh tube and total RNA recovered using the Maxwell RSC simplyRNA Tissue Kit (Promega) according to the manufacturer's instructions. The RNA (approximately 150 ng per sample) was reverse transcribed using the Maxima First Strand cDNA Synthesis Kit for RT-qPCR (ThermoFisher) according to the manufacturer's instructions. The level of ALOX15 or POSTN mRNA from each sample was measured in triplicate by real-time qPCR on an Applied Biosystems 7500 Fast Real-Time PCR machine using the TaqMan Gene Expression Assay for rabbit ALOX15 (ThermoFisher, assay #Oc03823548_s1). The level of GAPDH mRNA was measured in biplex reactions using TaqMan Gene Expression Assay (ThermoFisher, assay #Oc03823402_g1) and used to determine relative ALOX15 mRNA levels in each well using the delta-delta Ct method. All data were normalized to relative ALOX15 mRNA levels in samples from rabbits treated with vehicle only. Relative POSTN mRNA levels were measured as above using TaqMan Gene Expression Assay specific for rabbit POSTN mRNA (ThermoFisher, assay #Oc06804808_s1). The results are shown in FIG. 11. Relative levels of ALOX15 and POSTN mRNA in the nasal mucosa from both the rostral and caudal regions from rabbits treated with compound 5 were lower than the levels from the same regions from rabbits treated with vehicle. These results are consistent with the in vitro results shown in Example 8, where compound 5 inhibited ALOX15 and POSTN mRNA in primary human nasal epithelial cells.

What is claimed is:
1. A compound having the structure of Formula (I):

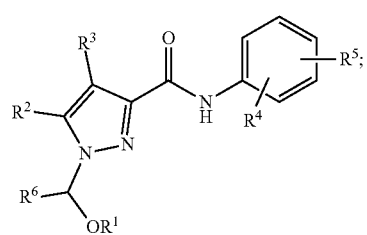

Formula (I)

wherein:
$R^1$ is —P(O)(OH)
$R^2$ is halogen;
$R^3$, $R^4$, and $R^5$ are each independently selected from H, halogen, and $C_{1-6}$alkyl optionally substituted with one, two, or three $R^{13}$;
$R^6$ is selected from H and $C_{1-6}$ alkyl; and
each $R_{13}$ is independently selected from halogen;
or a pharmaceutically acceptable salt or solvate thereof.
2. The compound of claim 1, or a pharmaceutically acceptable salt or solvate thereof, having the structure of Formula (Ia):

Formula (Ia)

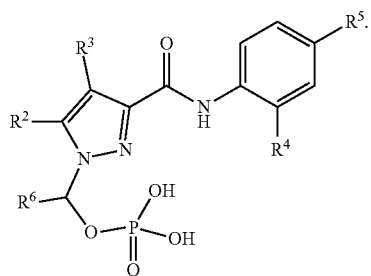

3. The compound of claim 2, or a pharmaceutically acceptable salt or solvate thereof, wherein $R^3$, $R^4$, and $R^5$ are each independently selected from H, halogen, and unsubstituted $C_{1-6}$alkyl.

4. The compound claim 3, or a pharmaceutically acceptable salt or solvate thereof, wherein $R^3$, $R^4$, and $R^5$ are each independently selected from H and halogen.

5. The compound of claim 3, or a pharmaceutically acceptable salt or solvate thereof, wherein $R^3$, $R^4$, and $R^5$ are each independently halogen.

6. The compound of claim 5, or a pharmaceutically acceptable salt or solvate thereof, wherein $R^6$ is H.

7. The compound of claim 5, or a pharmaceutically acceptable salt or solvate thereof, wherein $R^6$ is $C_{1-6}$alkyl.

8. The compound of claim 1 having the structure:

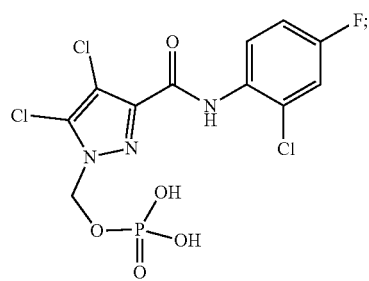 [SMILES: O=C(Nc1ccc(F)cc1Cl)c1nn(COP(=O)(O)O)c(Cl)c1Cl]

or a pharmaceutically acceptable salt or solvate thereof.

9. The compound of claim 1 selected from:

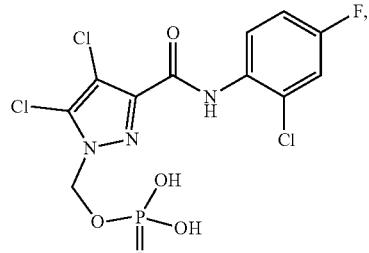

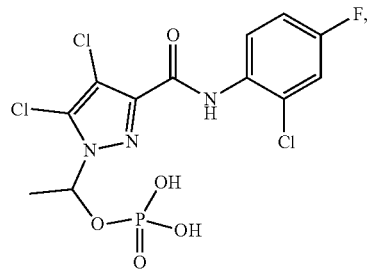

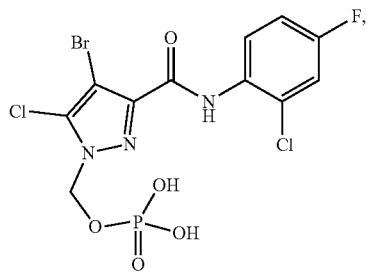

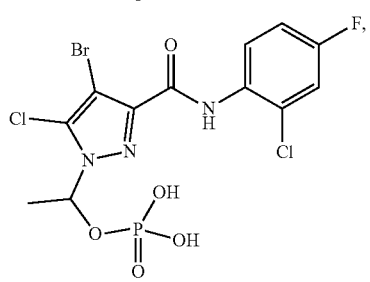

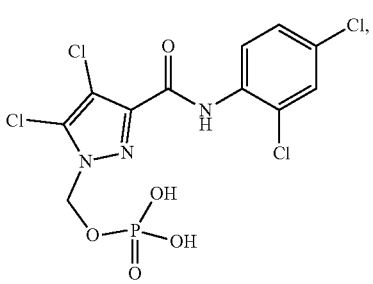

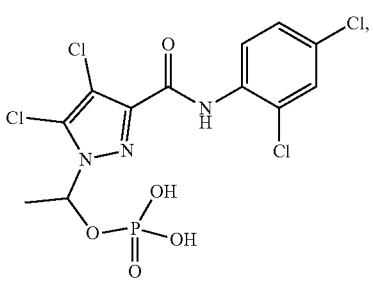

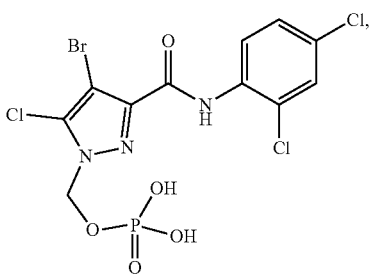

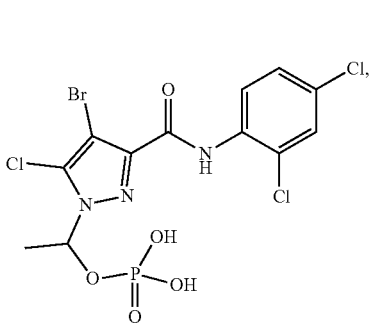

-continued
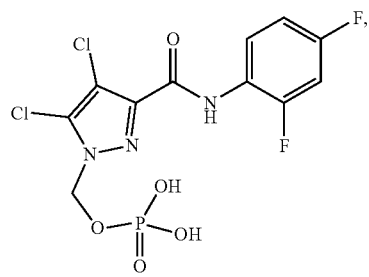
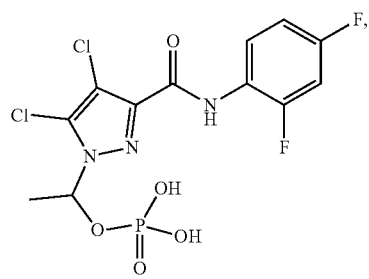
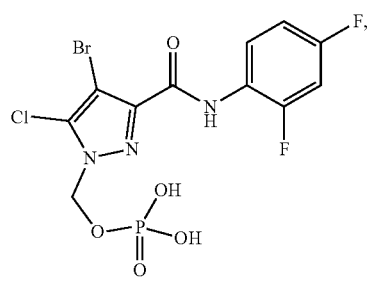
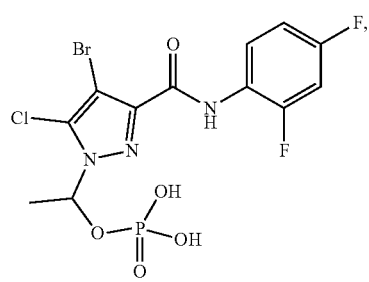
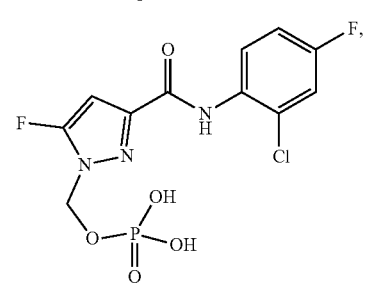
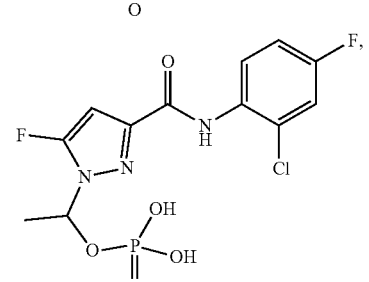
-continued
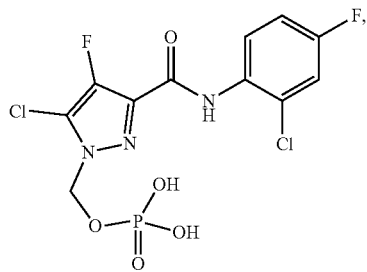
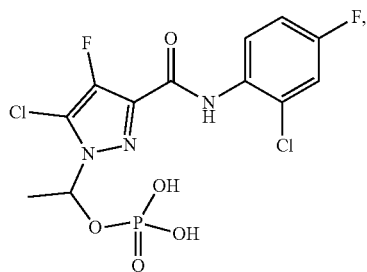
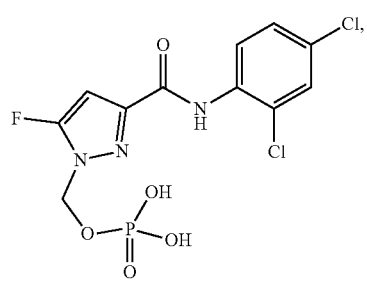
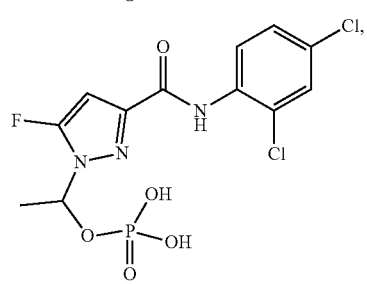
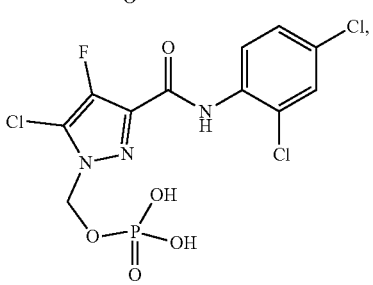
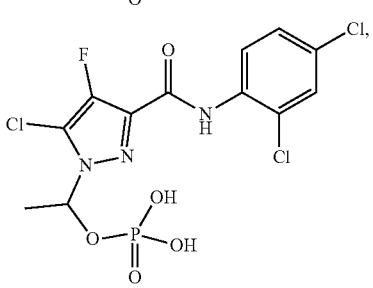

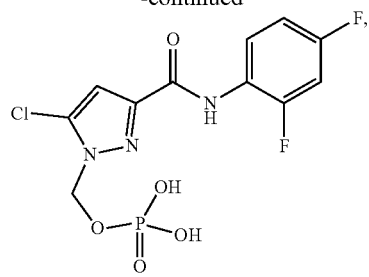
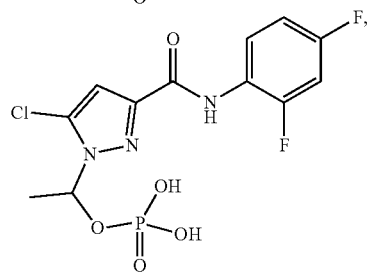
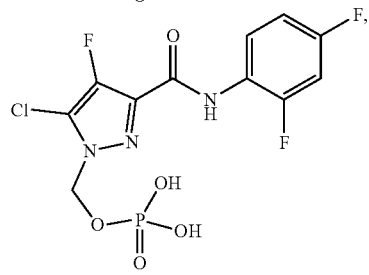
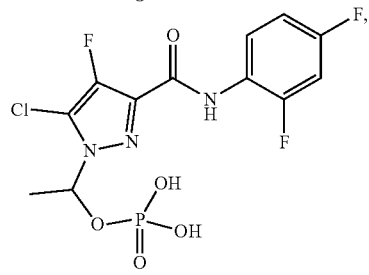
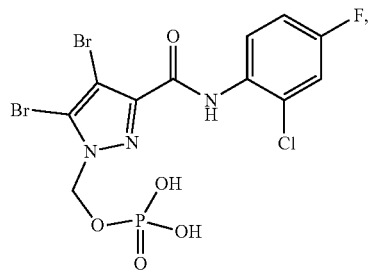
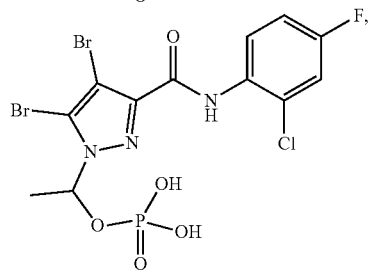
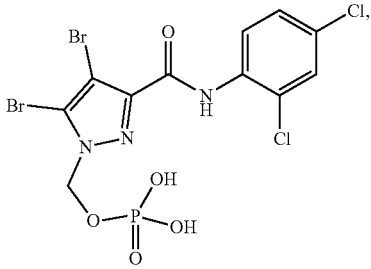
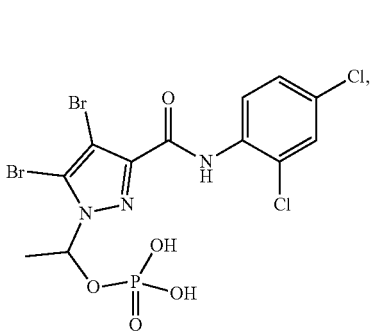
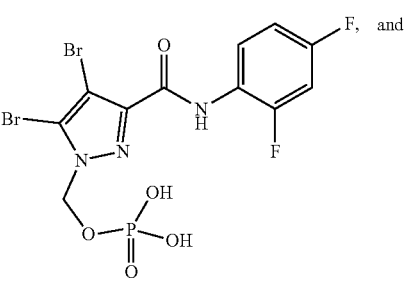
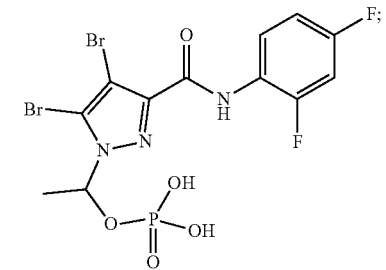
or a pharmaceutically acceptable salt or solvate thereof.
* * * * *

UNITED STATES PATENT AND TRADEMARK OFFICE
CERTIFICATE OF CORRECTION

PATENT NO. : 11,116,778 B2
APPLICATION NO. : 16/961242
DATED : September 14, 2021
INVENTOR(S) : Omri Gottesman et al.

It is certified that error appears in the above-identified patent and that said Letters Patent is hereby corrected as shown below:

In the Claims

1) Claim 1: Column 132, Line 57 should read as follows:
-$P(O)(OH)_2$

2) Claim 1: Column 132, Line 63 should read as follows:
$R^{13}$

Signed and Sealed this
Twenty-fourth Day of October, 2023

Katherine Kelly Vidal
*Director of the United States Patent and Trademark Office*